United States Patent
Guo et al.

(10) Patent No.: US 7,847,158 B2
(45) Date of Patent: Dec. 7, 2010

(54) MAIZE ERECTA GENES FOR IMPROVING PLANT GROWTH, TRANSPIRATION, EFFICIENCY AND DROUGHT TOLERANCE IN CROP PLANTS

(75) Inventors: Mei Guo, West Des Moines, IA (US); Mary Rupe, Altoona, IA (US); Carl Simmons, Des Moines, IA (US); Shoba Sivasankar, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 473 days.

(21) Appl. No.: 11/859,803

(22) Filed: Sep. 24, 2007

(65) Prior Publication Data

US 2008/0078004 A1    Mar. 27, 2008

Related U.S. Application Data

(60) Provisional application No. 60/847,304, filed on Sep. 25, 2006.

(51) Int. Cl.
| | |
|---|---|
| *C12N 15/29* | (2006.01) |
| *C12N 15/82* | (2006.01) |
| *C12N 5/04* | (2006.01) |
| *A01H 5/00* | (2006.01) |
| *A01H 5/10* | (2006.01) |

(52) U.S. Cl. .................... 800/290; 800/298; 800/320.1; 800/278; 536/23.1; 536/23.6; 435/320.1; 435/410

(58) Field of Classification Search ........................ None
See application file for complete search history.

(56) References Cited

U.S. PATENT DOCUMENTS

2005/0223428 A1    10/2005    Torii et al.

FOREIGN PATENT DOCUMENTS

| WO | 2004005555 A1 | 1/2004 |
| WO | 2007126850 A2 | 11/2007 |

OTHER PUBLICATIONS

Bowie et al, Science 247:1306-1310, 1990.*
McConnell et al, Nature 411 (6838):709-713, 2001.*
Wang et al (2007, Journal of Plant Physiology 164(5):655-664).*
XP-002474277; EMBL Database Accession No. Q69SP5; Sep. 13, 2004.
Torii, K., et al.; "The *Arabidopsis* ERECTA Gene Encodes a Putative Receptor Protein Kinase with Extracellular Leucine-Rich Repeats"; The Plant Cell (Apr. 1996) 8:735-746; American Society of Plant Physiologists; Rockville, MD, US.
Mizukami, Y., et al.; "Plant organ size control: Aintegumenta regulates growth and cell numbers during organogenesis"; PNAS (Jan. 18, 2000) 97(2):942-947; National Academy of Sciences; Washington, DC US.
Eyuboglu, B., et al.; "Molecular characterization of the Strubbelig-Receptor Family of genes encoding putative leucine-rich repeat receptor-like kinases in *Arabidopsis thaliana*"; BMC Plant Biology (2007) 7:16; BioMed Central Ltd; London, UK.
Hu, Y., et al.; "The *Arabidopsis* Argos-Like gene regulates cell expansion during organ growth"; The Plant Journal (2006) 47:1-9; Blackwell Publishing Ltd; Oxford, UK.
Hu, Y., et al.; "The *Arabidopsis* Auxin-Inducible Gene ARGOS Controls Lateral Organ Size"; The Plant Cell (Sep. 2003) 15:1951-1961; American Society of Plant Physiologists; Rockville, MD, US.
Shpak, E., et al.; "Synergistic interaction of three ERECTA-family receptor-like kinases controls *Arabidopsis* organ growth and flower development by promoting cell proliferation"; Development (2004) 131(7):1491-1501; The Company of Biologists; Cambridge, UK.
Hattan, J., et al.; "Molecular Characterization of the Cytoplasmic Interacting Protein of the Receptor Kinase IRK Expressed in the Inflorescence and Root Apices of *Arabidopsis*"; Biosci Biotechnol Biochem (2004) 68(12):2598-2606; Japanese Society for Bioscience, Biotechnology and Agrochemistry; Tokyo, JP.
Bemis, S., et al.; "Autonomy of cell proliferation and developmental programs during *Arabidopsis* aboveground organ morphogenesis"; Developmental Biology (2007), doi.10.1016/j.ydbio.2006.12.049; Elsevier; Amsterdam, Netherlands.

\* cited by examiner

*Primary Examiner*—Stuart F. Baum

(57) ABSTRACT

The present invention provides polynucleotides and related polypeptides of the ZmERECTA gene family. The invention provides nucleic acid sequences for the Zm ERECTA genes. ZmERECTA is responsible for controlling plant growth, organ size and yield in crop plants.

12 Claims, 9 Drawing Sheets

```
                          1                                                  50
SEQ ID NO: 2     (1)  ---------MALFRDIVLLGFLFCLSLVATVTSEEGATLLEIKKSFKDVN
SEQ ID NO: 4     (1)  ------MKEKMQRMVLSLAMVGFMVFGVASAMNNEGKALMAIKGSFSNLV
SEQ ID NO: 6     (1)  MPVRSSVAMTTTAARALAALVLVTAAAAAAAVADDGAALVEIKKSFRNVG
SEQ ID NO: 8     (1)  ----------------------------------ETLLEIKKSFRDGG
SEQ ID NO:10     (1)  ----MTPAPAAASYRALVALLLV-----AVAVADDGSTLLEIKKSFRNVD
SEQ ID NO:12     (1)  MAAARAPWLWWWVVVVVGVAVAEAASGGGGGDGEGKALMGVKAGFGNAA
SEQ ID NO:14     (1)  MPVRSSVAMTTTAARALVALLLV-----AVAVADDGATLVEIKKSFRNVG
SEQ ID NO:16     (1)  ------MAARAAAAVVLLIAAVVSVSAGGGEGDGDGQTLMAVKAGFGNAA
SEQ ID NO:18     (1)  --------------------------------------------------
SEQ ID NO:20     (1)  --------------------------------------------------
SEQ ID NO:22     (1)  --------------------------------------------------
SEQ ID NO:24     (1)  --------------------------------------------------
SEQ ID NO:26     (1)  --------------------------------------------------
SEQ ID NO:40     (1)                            AXXXXXXDGXXLLXIKXXFXXXX
                          51                                                 100
SEQ ID NO: 2    (42)  NVLYDWT-TS-PSSDYCVWRGVSCENVTFNVVALNLSDLNLDGEISPAIG
SEQ ID NO: 4    (45)  NMLLDWDDVHN--SDLCSWRGVFCDNVSYSVVSLNLSSLNLGGEISPAIG
SEQ ID NO: 6    (51)  NVLYDWA-----GDDYCSWRGVLCDNVTFAVAALNLSGLNLEGEISPAVG
SEQ ID NO: 8    (15)  NALYDWSGDG-ASPGYCSWRGVLCDNVTFAVAALNLSGLNLEGEISAAIG
SEQ ID NO:10    (42)  NVLYDWA-----GGDYCSWRGVLCDNVTFAVAALNLSGLNLGGEISPAVG
SEQ ID NO:12    (51)  NALVDWDGGA----DHCAWRGVTCDNASFAVLALNLSNLNLGGEISPAIG
SEQ ID NO:14    (46)  NVLYDWA-----GDDYCSWRGVLCDNVTFAVAALNLSGLNLEGEISPAVG
SEQ ID NO:16    (45)  NALADWDGGR----DHCAWRGVACDAASFAVVGLNLSNLNLGGEISPAIG
SEQ ID NO:18     (1)  --------------------------------------------------
SEQ ID NO:20     (1)  --------------------------------------------------
SEQ ID NO:22     (1)  --------------------------------------------------
SEQ ID NO:24     (1)  --------------------------------------------------
SEQ ID NO:26     (1)  --------------------------------------------------
SEQ ID NO:40    (23)  NXLXDWXXXXXXXXXDYCSWRGVXCDNXTFAVXALNLSXLNLXGEISPAIG
                         101                                                 150
SEQ ID NO: 2    (90)  DLKSLLSIDLRGNRLSGQIPDEIGDCSSLQNLDLSFNELSGDIPFSISKL
SEQ ID NO: 4    (93)  DLRNLQSIDLQGNKLAGQIPDEIGNCASLVYLDLSENLLYGDIPFSISKL
SEQ ID NO: 6    (96)  SLKSLVSIDLKSNGLSGQIPDEIGDCSSLRTLDFSFNNLDGDIPFSISKL
SEQ ID NO: 8    (64)  SLQRLVSIDLKSNGLSGQIPDEIGDCSLLETLDLSSNNLEGDIPFSMSKL
SEQ ID NO:10    (87)  RLKGIVSIDLKSNGLSGQIPDEIGDCSSLKTLDLSFNSLDGDIPFSVSKL
SEQ ID NO:12    (97)  ELKNLQFVDLKGNKLTGQIPDEIGDCISLKYLDLSGNLLYGDIPFSISKL
SEQ ID NO:14    (91)  SLKSLVSIDLKSNGLSGQIPDEIGDCSSLRTLDFSFNNLDGDIPFSISKL
SEQ ID NO:16    (91)  QLKSLQFVDLKLNKLTGQIPDEIGDCVSLKYLDLSGNLLYGDIPFSISKL
SEQ ID NO:18     (1)  --------------------------------------------------
SEQ ID NO:20     (1)  --------------------------------------------------
SEQ ID NO:22     (1)  --------------------------------------------------
SEQ ID NO:24     (1)  --------------------------------------------------
SEQ ID NO:26     (1)  --------------------------------------------------
SEQ ID NO:40    (73)  XLKXLXXIDLKXNXLSGQIPDEIGDCXSLXXLDXSXNXLXGDIPFSISKL
                         151                                                 200
SEQ ID NO: 2   (140)  KQLEQLILKNNQLIGPIPSTLSQIPNLKILDLAQNKLSGEIPRLIYWNEV
SEQ ID NO: 4   (143)  KQLETLNLKNNQLTGPVPATLTQIPNLKRLDLAGNHLTGEISRLLYWNEV
SEQ ID NO: 6   (146)  KHLENLILKNNRLIGAIPSTLSQLPNLKILDLAQNKLTGEIPRLIYWNEV
SEQ ID NO: 8   (114)  KHLENLILKNNKLVGIPSTLSQLPNLKILDLAQNKLSGEIPNLIYWNEV
SEQ ID NO:10   (137)  KHIESLILKNNQLIGVIPSTLSQLPNLKILDLAQNKLSGEIPRLIYWNEV
SEQ ID NO:12   (147)  KQLEELILKNNQLTGPIPSTLSQIPNLKTLDLAQNQLTGDIPRLIYWNEV
SEQ ID NO:14   (141)  KHLENLILKNNQLIGAIPSTLSQLPNLKILDLAQNKLTGEIPRLIYWNEV
SEQ ID NO:16   (141)  KQLEDLILKNNQLTGPIPSTLSQIPNLKTLDLAQNKLTGDIPRLIYWNEV
SEQ ID NO:18     (1)  --------------------------------------------------
SEQ ID NO:20     (1)  --------------------------------------------------
SEQ ID NO:22     (1)  --------------------------------------------------
SEQ ID NO:24     (1)  --------------------------------------------------
SEQ ID NO:26     (1)  --------------------------------------------------
SEQ ID NO:40   (123)  KXLEXLILKNNXLXGXIPSTLSQIPNLKXLDLAQNXLTGEIPRLIYWNEV
```

FIGURE 2a

```
                  201                                                250
SEQ ID NO: 2   (190) LQYLGLRGNNLVGNISPDLCQLTGLWYFDVRNNSLTGSIPETIGNCTAFQ
SEQ ID NO: 4   (193) LQYLGLRGNMLTGTLSSDMCQLTGLWYFDVRGNNLTGTIPESIGNCTSFQ
SEQ ID NO: 6   (196) LQYLGLRGNHLEGSLSPDMCQLTGLWYFDVKNNSLTGAIPDTIGNCTSFQ
SEQ ID NO: 8   (164) LQYLGLRSNSLEGSLSPDMCQLTGLWYFDVKNNSLTGAIPETIGNCTSFQ
SEQ ID NO:10   (187) LQYLGLRGNNLEGSISPDLCQLTGLWYFDVKNNSLTGPIPETIGNCTSFQ
SEQ ID NO:12   (197) LQYLGLRGNSLTGTLSPDMCQLTGLWYFDVRGNNLTGTIPESIGNCTSFE
SEQ ID NO:14   (191) LQYL---------------------DVKNNSLTGVIPDTIGNCTSFQ
SEQ ID NO:16   (191) LQYLGLRGNSLTGTLSPDMCQLTGLWYFDVRGNNLTGTIPEGIGNCTSFE
SEQ ID NO:18     (1) --------------------------------------------------
SEQ ID NO:20     (1) --------------------------------------------------
SEQ ID NO:22     (1) --------------------------------------------------
SEQ ID NO:24     (1) --------------------------------------------------
SEQ ID NO:26     (1) --------------------------------------------------
SEQ ID NO:40   (173) LQYLGLRXNXLXGXLSXDMCQLTGLWYFDVKXNXLTGXIPETIGNCTSFX
                  251                                                300
SEQ ID NO: 2   (240) VLDLSYNQLTGEIPFDIGFLQVATLSLQGNQLSGKIPSVIGLMQALAVLD
SEQ ID NO: 4   (243) ILDISYNQITGEIPYNIGFLQVATLSLQGNRLTGRIPEVIGLMQALAVLD
SEQ ID NO: 6   (246) VLDLSYNRFTGPIPFNIGFLQVATLSLQGNKFTGPIPSVIGLMQALAVLD
SEQ ID NO: 8   (214) VLDLSNNHLTGEIPFNIGFLQVATLSLQGNKFSGPIPSVIGLMQALAVLD
SEQ ID NO:10   (237) VLDLSYNKLSGSIPFNIGFLQVATLSLQGNMFTGPIPSVIGLMQALAVLD
SEQ ID NO:12   (247) ILDISYNQISGEIPYNIGFLQVATLSLQGNRLTGKIPDVIGLMQALAVLD
SEQ ID NO:14   (217) VLDLSYNRFTGPIPFNIGFLQVATLSLQGNKFGPIPSVIGLMQALAVLD
SEQ ID NO:16   (241) ILDISYNQISGEIPYNIGYLQVATLDLS----------------------
SEQ ID NO:18     (1) --------------------------------------------------
SEQ ID NO:20     (1) --------------------------------------------------
SEQ ID NO:22     (1) --------------------------------------------------
SEQ ID NO:24     (1) --------------------------------------------------
SEQ ID NO:26     (1) --------------------------------------------------
SEQ ID NO:40   (223) VLDLSYNXXTGXIPFNIGFLQVATLSLQGNXXTGXIPXVIGLMQALAVLD
                  301                                                350
SEQ ID NO: 2   (290) LSGNLLSGSIPPILGNLTFTEKLYLHSNKLTGSIPPELGNMSKLHYLELN
SEQ ID NO: 4   (293) LSDNELVGPIPPILGNLSFTGKLYLHGNMLTGPIPSELGNMSRLSYLQLN
SEQ ID NO: 6   (296) LSYNQLSGPIPSILGNLTYTEKLYMQGNRLTGSIPPELGNMSTLHYLELN
SEQ ID NO: 8   (264) LSFNELSGPIPSILGNLTYTEKLYLQGNRLTGLIPPELGNMSTLHYLELN
SEQ ID NO:10   (287) LSYNQLSGPIPSILGNLTYTEKLYMQGNKLTGPIPPELGNMSTLHYLELN
SEQ ID NO:12   (297) LSENELVGPIPSILGNLSYTGKLYLHGNKLTGVIPPELGNMSKLSYLQLN
SEQ ID NO:14   (267) LSYNQLSGPIPSILGNLTYTEKLYTQGNKLTGSIPPELGNMSTLHYLELN
SEQ ID NO:16   (269) --ENELVGPIPPILGNLSYTGKLYLHGNKLTGHIPPELGNMSKLSYLQLN
SEQ ID NO:18     (1) --------------------------------------------------
SEQ ID NO:20     (1) --------------------------------------------------
SEQ ID NO:22     (1) --------------------------------------------------
SEQ ID NO:24     (1) --------------------------------------------------
SEQ ID NO:26     (1) --------------------------------------------------
SEQ ID NO:40   (273) LSXNXLXGPIPXILGNLTYTXKLYLXGNKLTGXIPPELGNMSXLXYLXLN
                  351                                                400
SEQ ID NO: 2   (340) DNHLTGHIPPELGKLTDLFDLNVANNDLEGPIPDHISSCTNLNSLNVHGN
SEQ ID NO: 4   (343) DNKLVGTIPPELGKLEQLFELNLANNRLVGPIPSNISSCAALNQFNVHGN
SEQ ID NO: 6   (346) DNQLTGSIPPELGRLTGLFDLNPANNHLEGPIPDNLSSCVNLNSFNAYGN
SEQ ID NO: 8   (314) DNLLTGFIPPDLGKLTELFELNLANNNLIGPIPENLSSCANLISFNAYGN
SEQ ID NO:10   (337) DNQLSGFIPPEFGKLTGLFDLNLANNNFEGPIPDNISSCVNLNSFNAYGN
SEQ ID NO:12   (347) DNELVGTIPAELGKLEELFELNLANNNLQGPIPANLSSCTALNKFNVYGN
SEQ ID NO:14   (317) DNQLTGSIPPELGRLTGLFDLNLANNHLEGPIPDNLSSCVNLNSFNAYGN
SEQ ID NO:16   (317) DNELVGTIPAELGKLTELFELNLANNNLEGHIPANISSCSALNKFNVYGN
SEQ ID NO:18     (1) --------------------------------------------------
SEQ ID NO:20     (1) --------------------------------------------------
SEQ ID NO:22     (1) --------------------------------------------------
SEQ ID NO:24     (1) --------------------------------------------------
SEQ ID NO:26     (1) --------------------------------------------------
SEQ ID NO:40   (323) DNXLXGXIPXELGKLXXLFDLNLANNXLXGPIPXNISSCXXLNXFNXYGN
```

FIGURE 2b

```
                401                                              450
SEQ ID NO: 2   (390) KFSGTIPRAFQKLESMTYLNLSSNNIKGPIPVELSRIGNLDTLDLSNNKI
SEQ ID NO: 4   (393) LLSGSIPLAFRNLGSLTYLNLSSNNFKGKIPVELGHIINLDKLDLSGNNF
SEQ ID NO: 6   (396) KLNGTIPRSLRKLESMTYLNLSSNFISGSIPIELSRINNLDTLGLSCNMM
SEQ ID NO: 8   (364) KLNGTIPRSFHKLESLTYLNLSSNHLSGALPIEVARMRNLDTLDLSCNMI
SEQ ID NO:10   (387) RLNGTIPPSLHKLESMTYLNLSSNFLSGSIPIELSRINNLDTLDLSCNMI
SEQ ID NO:12   (397) KLNGSIPAGFQKLESLTYLNLSSNNFKGNIPSELGHIINLDTLDLSYNEF
SEQ ID NO:14   (367) KLNGTIPRSLRKLESMTYLNLSSNFISGSIPIELSRINNLDTLDLSCNMM
SEQ ID NO:16   (367) RLNGSIPAGFQELESLTYLNLSSNNFKGQIPSELGHIVNLDTLDLSYNEF
SEQ ID NO:18    (1) --------------------------------------------------
SEQ ID NO:20    (1) --------------------------------------------------
SEQ ID NO:22    (1) --------------------------------------------------
SEQ ID NO:24    (1) --------------------------------------------------
SEQ ID NO:26    (1) --------------------------------------------------
SEQ ID NO:40   (373) KLXGTIPXXXXXLESLTYLNLSSNXXXGXIPXELXXIXNLDTLDLSXNXX
                451                                              500
SEQ ID NO: 2   (440) NGIIPSSLGDLEHLLKMNLSRNHITGVVPGDFGNLRSIMEIDLSNNDISG
SEQ ID NO: 4   (443) SGSIPLTLGDLEHLLILNLSRNHLSGQLPAEFGNLRSIQMIDVSFNLLSG
SEQ ID NO: 6   (446) TGPIPSSIGNLEHLLRLNLSKNDLVGFIPAEFGNLGSVMEIDLSYNHLGG
SEQ ID NO: 8   (414) TGSIPSAIGKLEHLLRLNLSKNNVAGHIPAEFGNLRSIMEIDLSYNHLSG
SEQ ID NO:10   (437) TGPIPSTIGSLEHLLRLNLSNNGLVGFIPAEIGNLRSIMEIDMSNNHLGG
SEQ ID NO:12   (447) SGPVPATIGDLEHLLELNLSKNHLDGPVPAEFGNLRSVQVIDMSNNLSG
SEQ ID NO:14   (417) TGPIPSSIGSLEHLLRLNLSKNGLVGFIPAEFGNLRSVMEIDLSYNHLGG
SEQ ID NO:16   (417) SGPVPPTIGDLEHLLELNLSKNHLTGSVPAEFGNLRSVQVIDISSNNLTG
SEQ ID NO:18    (1) --------------------------------------------------
SEQ ID NO:20    (1) --------------------------------------------------
SEQ ID NO:22    (1) --------------------------------------------------
SEQ ID NO:24    (1) --------------------------------------------------
SEQ ID NO:26    (1) --------------------------------------------------
SEQ ID NO:40   (423) TGXIPXTIGXLEHLLXLNLSKNXLXGXIPAEFGNLRSIXXIDLSXNXLXG
                501                                              550
SEQ ID NO: 2   (490) PIPEELNQLQNIILLRLENNNLTGNV-GSLANCLSLTVLNVSHNNLVGDI
SEQ ID NO: 4   (493) VIPTELGQLQNLNSLILNNNKLHGKIPDQLTNCFTLVNLNVSFNNLSGIV
SEQ ID NO: 6   (496) LIPQELGMLQNLMLLKLENNNITGDV-SSLMNCFSLNILNVSYNNLAGAV
SEQ ID NO: 8   (464) LIPQEVGMLQNLILLKLESNNITGDV-SSLIYCLSLNILNVSYNHLYGTV
SEQ ID NO:10   (487) LIPQELGMLQNLMLLNLKNNNITGDV-SSLMNCFSLNILNVSYNNLAGVV
SEQ ID NO:12   (497) SLPEELGQLQNLDSLILNNNNLVGEIPAQLANCFSLNNLAFQEFVIQQFI
SEQ ID NO:14   (467) LIPQELEMLQNLMLLNVS------------------------YNNLAGVV
SEQ ID NO:16   (467) YLPEELGQLQNLDSLILNNNNLVGEIPAQLANCFSLIT------------
SEQ ID NO:18    (1) --------------------------------------------------
SEQ ID NO:20    (1) ---------------------------LSLSLLNVSYNKLFGVI
SEQ ID NO:22    (1) --------------------------------------------------
SEQ ID NO:24    (1) --------------------------------------------------
SEQ ID NO:26    (1) --------------------------------------------------
SEQ ID NO:40   (473) XIPXELXXLQNLXXLXLXXNXLXGXVXXXLXXCXSLXXLXXXNXLXGXVX
                551                                              600
SEQ ID NO: 2   (539) PKNNNFSRFSPDSFIGNPGLCGSWLNSPCHDSRRTVRVS---------I
SEQ ID NO: 4   (543) PPMKNFSRFAPASFVGNPYLCGNWVGSICGPLPK------------S--
SEQ ID NO: 6   (545) PTDNNFTRFSHDSFLGNPGLCGYWLGSSCRSTGHRDKPP---------I
SEQ ID NO: 8   (513) PTDNNFSRFSPDSFLGNPGLCGYWLHSASCTQLSNAEQMKRSSS---AKA
SEQ ID NO:10   (536) PTDNNFSRFSPDSFLGNPGLCGYWLGSSCRSSGHQQKPL---------I
SEQ ID NO:12   (547) WTCPDGKELLEIPNGKHLLISDCNQYINHKCSFLGNPLLHVYCQDSSCGH
SEQ ID NO:14   (493) PADNNFTRFSPDSFLGNPGLCGYWLGSSCRSTGHHEKPP---------I
SEQ ID NO:16   (505) --------------------------------------------------
SEQ ID NO:18    (1) --------------------------------------------------
SEQ ID NO:20   (18) PTSNNFTRFPPDSFIGNPGLCGNWLNLPCHGARPSERVT----------L
SEQ ID NO:22    (1) --------------------------------------------------
SEQ ID NO:24    (1) --------------------------------------------------
SEQ ID NO:26    (1) --------------------------------------------------
SEQ ID NO:40   (523) PXXXNFSRFXXXSFLGNPXLCGXWLXXXXXXXXXXXXXXXXXXXXXXXXX
```

FIGURE 2c

```
                       601                                                650
SEQ ID NO: 2    (579)  SRAAILGIAIGGLVILLMVLIAACRPHNPPPFLDGSLDKPVTYS------
SEQ ID NO: 4    (578)  -----RVFSRGALICIVLGVITLLCMIFLAVYKSMQQKKILQGSSKQAEG
SEQ ID NO: 6    (585)  SKAAITGVAVGGLVILLMILVAVCRPHHPPAFKDATVSKPVSNG------
SEQ ID NO: 8    (560)  SMFAAIGVGAVLLVIMLVILVVICWPHNSPVLKDVSVNKPDNLASASNNI
SEQ ID NO:10    (576)  SKAAILGIAVGGLVILLMILVAVCRPHSPPVFKDVSVSKPVSNV------
SEQ ID NO:12    (597)  SHGQRVNISKTAIACTILGFIILLCVLLLAIYKTNQPQPLVKGSDKPVQG
SEQ ID NO:14    (533)  SKAAITGVAVGGLVILLMILVAVCRPHRPPAFKDVTVSKPVRNA------
SEQ ID NO:16    (505)  --------------------------------------------------
SEQ ID NO:18    (1)    --------------------------------------------------
SEQ ID NO:20    (58)   SKAAILGITLGALVILLMVLVAACRPHSPSPFPDGSFDKPINFS------
SEQ ID NO:22    (1)    --------------------------------------------------
SEQ ID NO:24    (1)    --------------------------------------------------
SEQ ID NO:26    (1)    --------------------------------------------------
SEQ ID NO:40    (573)  SXXXXIXIXXXGLVXLLMXLVXXXXXXXXXXFXXXXXXXKXVXXXXXXXX
                       651                                                700
SEQ ID NO: 2    (623)  TPKLVILHMNMALHVYEDIMRMTENLSEKYIIGHGASSTVYKCVLKNCKP
SEQ ID NO: 4    (623)  LTKLVILHMDMAIHTFDDIMRVTENLNEKFIIGYGASSTVYKCALKSSRP
SEQ ID NO: 6    (629)  PPKLMILHMNMALHVEDDIMRMTENLSEKYIIGYGASSTVYKCVLKNCKP
SEQ ID NO: 8    (610)  HPKLVILHMNMALYVYDDIMRMTENLSEKYIIGYGASSTVYRCDLKNCKP
SEQ ID NO:10    (620)  PPKLVILHMNLSLLVYEDIMTMTENLSEKYIIGYGASSTVYKCVSKNRKP
SEQ ID NO:12    (647)  PPKLVVLQMDMAIHTYEDIMRLTENLSEKYIIGYGASSTVYKCELKSGKA
SEQ ID NO:14    (577)  PPKLVILHMNMALHVYDDIMRMTENLSEKYIIGYGASSTVYKCVLKNCKP
SEQ ID NO:16    (505)  --------------------------------------------------
SEQ ID NO:18    (1)    ------LQMDMATHTYEDIMRLTENLSEKYIIGYGASSTVYKCDLKGGKA
SEQ ID NO:20    (102)  PPKLVILHMNMALHVYEDIMRMTENLSEKYIIGYGASSTVYKCVLKNCKP
SEQ ID NO:22    (1)    --------------------------------------------------
SEQ ID NO:24    (1)    --------------------------------------------------
SEQ ID NO:26    (1)    ---------------------------------STVYKCVLKNCKP
SEQ ID NO:40    (623)  XPKLVILHMXMALHXYEDIMRMTENLSEKYIIGYGASSTVYKCXLKNXKP
                       701                                                750
SEQ ID NO: 2    (673)  VAIKRLYSHNPQSMKQFETELEMISSIKHRNLVSLQAYSLSHLGSLLFYD
SEQ ID NO: 4    (673)  IAIKRLYNQYPHNLREFETELETIGSIRHRNIVSLHGYALSPTGNLLFYD
SEQ ID NO: 6    (679)  VAIKKLYAHYPQSLKEFETELETVGSIKHRNLVSLQGYSLSPVGNLLFYD
SEQ ID NO: 8    (660)  IAIKKLYAHYPQSLKEFETELETVGSIKHRNLVSLQGYSLSPSGNLLFYD
SEQ ID NO:10    (670)  VAVKKLYAHYPQSFKEFETELETVGSIKHRNLVSLQGYSLSPVGNLLFYD
SEQ ID NO:12    (697)  IAVKRLYSQYNHSLREFETELETIGSIRHRNLVSLHGFSLSPHGNLLFYD
SEQ ID NO:14    (627)  VAIKKLYAHYPQSLKEFETELETVGSIKHRNLVSLQGYSLSPVGNLLFYD
SEQ ID NO:16    (505)  --------------------------------------------------
SEQ ID NO:18    (45)   IAVKRLYSQYNHSLREFETELETIGSIRHRNLVSLHGFSLSPHGNLLFYD
SEQ ID NO:20    (152)  VAIKRIYSHYPQCIKEFETELETVGSIKHRNLVSLQGYSLSPYGHLLFYD
SEQ ID NO:22    (1)    --------------------------------------------------
SEQ ID NO:24    (1)    --------------------------------------------------
SEQ ID NO:26    (14)   VAIKKLYSHYPQYLKEFETELETVGSVKHRNLVSLQGYSLSTYGNLLFYD
SEQ ID NO:40    (673)  VAIKKLYSHYPQSLKEFETELETVGSIKHRNLVSLQGYSLSPXGNLLFYD
                       751                                                800
SEQ ID NO: 2    (723)  YLENGSLWDLLHGP-TKKKTLDWDTRLKIAYGAAQGLAYLHHDCSPRIIH
SEQ ID NO: 4    (723)  YMENGSLWDLLHGS-LKKVKLDWETRLKIAVGAAQGLAYLHHDCTPRIIH
SEQ ID NO: 6    (729)  YMESGSLWDVLHEGSSKENKLDWVTRLRIALGAAQGLAYLHHDCSPRIIH
SEQ ID NO: 8    (710)  YMENGSLWDILHAS-SKKKKLDWEARLKIALGAAQGLAYLHHECSPRIIH
SEQ ID NO:10    (720)  YMENGSLWDVLHEGPTKKKKLDWETRLRIALGAAQGLAYLHHDCSPRIIH
SEQ ID NO:12    (747)  YMENGSLWDLLHGP-SKKVKLNWDTRLRIAVGAAQGLAYLHHDCNPRIIH
SEQ ID NO:14    (677)  YMECGSLWDVLHEGSSKKKKLDWETRLRIALGAAQGLAYLHHDCSPRIIH
SEQ ID NO:16    (505)  --------------------------------------------------
SEQ ID NO:18    (95)   YMENGSLWDLLHGP-SKKVKLDWDTRLKIAVGAAQGLAYLHHDCNPRIIH
SEQ ID NO:20    (202)  YMENGSLWDLLHGP-TKKKKLDWELRLKIALGAAQGLAYLHHDCCPRIIH
SEQ ID NO:22    (1)    --------------------------------------------------
SEQ ID NO:24    (1)    --ENGSLWDLLHGP-TKKKKLDWDLRLKIALGSAQGLAYLHHDCSPLIIH
SEQ ID NO:26    (64)   YMENGSLWDLLHGP-TKKKKLDWDLRLKIAL-------------------
SEQ ID NO:40    (723)  YMENGSLWDLLHGXXSKKKKLDWDTRLKIALGAAQGLAYLHHDCSPRIIH
```

FIGURE 2d

```
                801                                              850
SEQ ID NO: 2   (772) RDVKSSNILLDKDLEARLTDFGIAKSLCVSKSHTSTYVMGTIGYIDPEYA
SEQ ID NO: 4   (772) RDIKSSNILLDENFEAHLSDFGIAKSIPASKTHASTYVLGTIGYIDPEYA
SEQ ID NO: 6   (779) RDVKSKNILLDKDYEAHLTDFGIAKSLCVSKTHTSTYVMGTIGYIDPEYA
SEQ ID NO: 8   (759) RDVKSKNILLDKDYEAHLADFGIAKSLCVSKTHTSTYVMGTIGYIDPEYA
SEQ ID NO:10   (770) RDVKSKNILLDKDYEAHLTDFGIAKSLCVSKTHTSTYVMGTIGYIDPEYA
SEQ ID NO:12   (796) RDVKSSNILLDENFEAHLSDFGIAKCVPSAKSHASTYVLGTIGYIDPEYA
SEQ ID NO:14   (727) RDVKSKNILLDKDYEAHLTDFGIAKSLCVSKTHTSTYVMGTIGYIDPEYA
SEQ ID NO:16   (505) -------------------------------------------------
SEQ ID NO:18   (144) RDVKSSNILLDENFEAHLSDFGIAKCVPAAKSHASTYVLGTIGYIDPEYA
SEQ ID NO:20   (251) RDVKSSNILLDADFEPHLTDFGIAKSLCPSKSHTSTYIMGTIGYIDPEYA
SEQ ID NO:22     (1) ----------------------------------------------EYA
SEQ ID NO:24    (48) RDVKSSNILLDKDFEPHLADFGIAKSLCPSKTHTSTYIMGTIGYIDPEYA
SEQ ID NO:26    (94) -------------------------------------------------
SEQ ID NO:40   (773) RDVKSXNILLDXDFEAHLTDFGIAKSLCXSKTHTSTYVMGTIGYIDPEYA
                851                                              900
SEQ ID NO: 2   (822) RTSRLTEKSDVYSYGIVLLELLTRRKAVDDESNLHHLIMSKTGNNEVMEM
SEQ ID NO: 4   (822) RTSRINEKSDIYSFGIVLLELLTGKKAVDNEANLHQLILSKADDNTVMEA
SEQ ID NO: 6   (829) RTSRLNEKSDVYSYGIVLLELLTGKKPVDNECNLHHLILSKTASNEVMET
SEQ ID NO: 8   (809) RTSRINEKSDVYSYGIVLLELLTGKKPVDDECNLHHLILSKAAENTVMET
SEQ ID NO:10   (820) RTSRLNEKSDVYSYGIVLLELLTGKKPVDNECNLHHLILSKTANNAVMET
SEQ ID NO:12   (846) RTSRLNEKSDVYSFGIVLLELLTGKKAVDNESNLHQLILSKADDNTVMEA
SEQ ID NO:14   (777) RTSRLNEKSDVYRLWHCSAGAADWQEASG-----Q-RILSKTASNEVMDT
SEQ ID NO:16   (505) -------------------------------------------------
SEQ ID NO:18   (194) RTSRLNEKSDVYSFGIVLLELLTGKKAVDNESNLHQLILSKADDNTVMEA
SEQ ID NO:20   (301) RTSRLTEKSDVYSYGIVLLELLTGRKAVDNESNLHHLILSKAATNAVMET
SEQ ID NO:22     (4) RTSHLTEKSDVYSYGIVLLELLTGRKAVDNESNLHHLILSKAATNAVMET
SEQ ID NO:24    (98) RTSRLTEKSDVYSYGIVLLELLTGRKAVDNESNLHHLILSKTANDGVMET
SEQ ID NO:26    (94) -------------------------------------------------
SEQ ID NO:40   (823) RTSRLNEKSDVYSYGIVLLELLTGKKAVDNESNLHHLILSKXAXNXVMET
                901                                              950
SEQ ID NO: 2   (872) ADPDITSTCKDLGVVKKVFQLALLCTKRQPNDRPTMHQVTRVLGSFMLSE
SEQ ID NO: 4   (872) VDPEVTVTCMDLGHIRKTFQLALLCTKRNPLERPTMLEVSRVLLSLVPSL
SEQ ID NO: 6   (879) VDPDVGDTCKDLGEVKKLFQLALLCTKRQPSDRPTMHEVVRVLDCLVNPE
SEQ ID NO: 8   (859) VDQDITDTCKDLGEVKKVFQLALLCSKRQPSDRPTMHEVARVLDSLVCPA
SEQ ID NO:10   (870) VDPDIADTCKDLGEVKKVFQLALLCTKRQPSDRPTMHEVVRVLDCLVRPD
SEQ ID NO:12   (896) VDSEVSVTCTDMGLVRKAFQLALLCTKRHPSDRPTMHEVARVLLSLLPAS
SEQ ID NO:14   (821) VDPDIGDTCKDLGEVKKLFQLALLCTKRQPSDRPTMHEVVRVLDCLVNPD
SEQ ID NO:16   (505) -------------------------------------------------
SEQ ID NO:18   (244) VDSEVSV------------------------------------------
SEQ ID NO:20   (351) VDPDITATCKDLGAVKKVYQLALLCTKRQPADRPTMHEVTRVLGSLVLSN
SEQ ID NO:22    (54) VDPDITATCKDLGAVKKVYQLALLCTKRQPADRPTMHEVTRVLGSLVPSS
SEQ ID NO:24   (148) VDPDITTTCRDMGAVKKVFQLALLCTKKQPVDRPTMHEVTRVWEALCHP-
SEQ ID NO:26    (94) -------------------------------------------------
SEQ ID NO:40   (843) VDPDITXTCKDLGXVKKVFQLALLCTKRQPSDRPTMHEVXRVLXSLVXXX
                951                                             1000
SEQ ID NO: 2   (922) QPP-----------AATDTSATLAGSCYVDEYANLKTP---HSVNCS-S
SEQ ID NO: 4   (922) QVAKKLPSLDHSTKKLQQENEVRNPDAEASQWFVQFREVISKSSI-----
SEQ ID NO: 6   (929) PPPQPQQQQQKAHAHHQLP-PQ-PSPPAYVDEYVSLRGTG---ALSCANS
SEQ ID NO: 8   (909) GPPPKQAQ---AQAQAQASEKPSTTAPSYVSEYVGLRGGGGGSALSCTNS
SEQ ID NO:10   (920) PPPKS--------AQQLAMPQRPAVPSYINEYVSLRGTG---VLSCANS
SEQ ID NO:12   (946) AMTTPKTVDYSRLLASTTTAADMRGHDVTDIGDNSSSDEQWFVRFGEVIS
SEQ ID NO:14   (871) PPPKP------S--AHQLPQPS-PAVPSYINEYVSLRGTG---ALSCANS
SEQ ID NO:16   (505) -------------------------------------------------
SEQ ID NO:18   (251) -------------------------------------------------
SEQ ID NO:20   (401) TPPKQ-------LAALPPASDPSAXVPCYVDEYGKPQDSTLGETAPQ---
SEQ ID NO:22   (104) IPPKQ-------LADLPPASNPSAKVPCYVDEYANLKTP---HLVNCP-S
SEQ ID NO:24   (197) -------------------------------------------------
SEQ ID NO:26    (94) -------------------------------------------------
SEQ ID NO:40   (923) XPPXXXXXXXXXXXXXXXXXXXXXXXXXXYVXEYXXRXXXXXXXXLXXXS
```

FIGURE 2e

```
                              1001              1021
SEQ ID NO: 2   (956)  MSASDAQLFLRFGQVISQNSE
SEQ ID NO: 4   (967)  ---------------------
SEQ ID NO: 6   (974)  SSTSDAELFLKFGEAISQNMV
SEQ ID NO: 8   (956)  SSASDAELFMKFGEVISRSTE
SEQ ID NO:10   (958)  SCTSDAELFLKFGEVISQNTE
SEQ ID NO:12   (996)  KHTM-----------------
SEQ ID NO:14   (909)  TSTSDAELFLKFGEAISQNME
SEQ ID NO:16   (505)  ---------------------
SEQ ID NO:18   (251)  ---------------------
SEQ ID NO:20   (441)  ---------------------
SEQ ID NO:22   (143)  MSTSDAQLFLKFGEVISQNSE
SEQ ID NO:24   (197)  ---------------------
SEQ ID NO:26    (94)  ---------------------
SEQ ID NO:40   (973)
```

FIGURE 2f

SEQUENCE LISTING

<160> NUMBER OF SEQ ID NOS: 40

<210> SEQ ID NO 1
<211> LENGTH: 3191
<212> TYPE: DNA
<213> ORGANISM: Arabidopsis thaliana

<400> SEQUENCE: 1

| | | | | | |
|---|---|---|---|---|---|
| gtttcttctt | catggagact | tgaaagcttt | taaagtatat | ctaaaaacgc | agtcgtttta | 60 |
| agactgtgtg | tgagaaatgg | ctctgtttag | agatattgtt | cttcttgggt | ttctcttctg | 120 |
| cttgagctta | gtagctactg | tgacttcaga | ggagggagca | acgttgctgg | agattaagaa | 180 |
| gtcattcaaa | gatgtgaaca | atgttcttta | tgactggaca | acttcacctt | cttcggatta | 240 |
| ttgtgtctgg | agaggtgtgt | cttgtgaaaa | tgtcaccttc | aatgttgttg | ctcttaattt | 300 |
| gtcagatttg | aatcttgatg | gagaaatctc | acctgctatt | ggagatctca | agagtctctt | 360 |
| gtcaattgat | ctgcgaggta | atcgcttgtc | tggacaaatc | cctgatgaga | ttggtgactg | 420 |
| ttcttctttg | caaaacttag | acttatcctt | caatgaatta | agtggtgaca | taccgttttc | 480 |
| gatttcgaag | ttgaagcaac | ttgagcagct | gattctgaag | aataaccaat | tgataggacc | 540 |
| gatcccttca | acactttcac | agattccaaa | cctgaaaatt | ctggacttgg | cacagaataa | 600 |
| actcagtggt | gagataccaa | gacttattta | ctggaatgaa | gttcttcagt | atcttgggtt | 660 |
| gcgaggaaac | aacttagtcg | gtaacatttc | tccagatttg | tgtcaactga | ctggtctttg | 720 |
| gtattttgac | gtaagaaaca | acagtttgac | tggtagtata | cctgagacga | taggaaattg | 780 |
| cactgccttc | caggttttgg | acttgtccta | caatcagcta | actggtgaga | tcccttttga | 840 |
| catcggcttc | ctgcaagttg | caacattatc | attgcaaggc | aatcaactct | ctgggaagat | 900 |
| tccatcagtg | attggtctca | tgcaagccct | tgcagtctta | gatctaagtg | caacttgtt | 960 |
| gagtggatct | attcctccga | ttctcggaaa | tcttactttc | accgagaaat | tgtatttgca | 1020 |
| cagtaacaag | ctgactggtt | caattccacc | tgagcttgga | aacatgtcaa | aactccatta | 1080 |
| cctggaactc | aatgataatc | atctcacggg | tcatatacca | ccagagcttg | ggaagcttac | 1140 |
| tgacttgttt | gatctgaatg | tggccaacaa | tgatctggaa | ggacctatac | ctgatcatct | 1200 |
| gagctcttgc | acaaatctaa | acagcttaaa | tgttcatggg | aacaagttta | gtggcactat | 1260 |
| accccgagca | tttcaaaagc | tagaaagtat | gacttacctt | aatctgtcca | gcaacaatat | 1320 |
| caaaggtcca | atcccggttg | agctatctcg | tatcggtaac | ttagatacat | tggatctttc | 1380 |
| caacaacaag | ataaatggaa | tcattccttc | ttcccttggt | gatttggagc | atcttctcaa | 1440 |
| gatgaacttg | agtagaaatc | atataactgg | tgtagttcca | ggcgactttg | gaaatctaag | 1500 |
| aagcatcatg | gaaatagatc | tttcaaataa | tgatatctct | ggcccaattc | agaagagct | 1560 |
| taaccaatta | cagaacataa | ttttgctgag | actggaaaat | aataacctga | ctggtaatgt | 1620 |
| tggttcatta | gccaactgtc | tcagtctcac | tgtattgaat | gtatctcata | caacctcgt | 1680 |
| aggtgatatc | cctaagaaca | ataacttctc | aagattttca | ccagacagct | tcattggcaa | 1740 |
| tcctggtctt | tgcggtagtt | ggctaaactc | accgtgtcat | gattctcgtc | gaactgtacg | 1800 |
| agtgtcaatc | tctagagcag | ctattcttgg | aatagctatt | ggggacttg | tgatccttct | 1860 |
| catggtctta | atagcagctt | gccgaccgca | taatcctcct | cctttcttg | atggatcact | 1920 |
| tgacaaacca | gtaacttatt | cgacaccgaa | gctcgtcatc | cttcatatga | acatggcact | 1980 |
| ccacgtttac | gaggatatca | tgagaatgac | agagaatcta | agtgagaagt | atatcattgg | 2040 |

-continued

```
gcacggagca tcaagcactg tatacaaatg tgttttgaag aattgtaaac cggttgcgat    2100
taagcggctt tactctcaca acccacagtc aatgaaacag tttgaaacag aactcgagat    2160
gctaagtagc atcaagcaca gaaatcttgt gagcctacaa gcttattccc tctctcactt    2220
ggggagtctt ctgttctatg actatttgga aaatggtagc ctctgggatc ttcttcatgg    2280
ccctacgaag aaaaagactc ttgattggga cacacggctt aagatagcat atggtgcagc    2340
acaaggttta gcttatctac accatgactg tagtccaagg atcattcaca gagacgtgaa    2400
gtcgtccaac attctcttgg acaaagactt agaggctcgt ttgacagatt ttggaatagc    2460
gaaaagcttg tgtgtgtcaa agtcacatac ttcaacttac gtgatgggca cgataggtta    2520
catagacccc gagtatgctc gcacttcacg gctcactgag aaatccgatg tctacagtta    2580
tggaatagtc cttcttgagt tgttaacccg aaggaaagcc gttgatgacg aatccaatct    2640
ccaccatctg ataatgtcaa agacggggaa caatgaagtg atggaaatgg cagatccaga    2700
catcacatcg acgtgtaaag atctcggtgt ggtgaagaaa gttttccaac tggcactcct    2760
atgcaccaaa agacagccga tgatcgacc cacaatgcac caggtgactc gtgttctcgg    2820
cagttttatg ctatcggaac aaccacctgc tgcgactgac acgtcagcga cgctggctgg    2880
ttcgtgctac gtcgatgagt atgcaaatct caagactcct cattctgtca attgctcttc    2940
catgagtgct tctgatgctc aactgtttct tcggtttgga caagttattt ctcagaacag    3000
tgagtagttt ttcgttagga ggagaatctt taaaacggta tcttttcgtt gcgttaagct    3060
gttagaaaaa ttaatgtctc atgtaaagta ttatgcactg ccttattatt attagacaag    3120
tgtgtggtgt gaatatgtct tcagactggc acttagactt cctataagtt cttgcctatc    3180
taagtttttc t                                                         3191
```

<210> SEQ ID NO 2
<211> LENGTH: 976
<212> TYPE: PRT
<213> ORGANISM: Arabidopsis thaliana

<400> SEQUENCE: 2

```
Met Ala Leu Phe Arg Asp Ile Val Leu Leu Gly Phe Leu Phe Cys Leu
 1               5                  10                  15

Ser Leu Val Ala Thr Val Thr Ser Glu Glu Gly Ala Thr Leu Leu Glu
            20                  25                  30

Ile Lys Lys Ser Phe Lys Asp Val Asn Asn Val Leu Tyr Asp Trp Thr
        35                  40                  45

Thr Ser Pro Ser Ser Asp Tyr Cys Val Trp Arg Gly Val Ser Cys Glu
    50                  55                  60

Asn Val Thr Phe Asn Val Val Ala Leu Asn Leu Ser Asp Leu Asn Leu
65                  70                  75                  80

Asp Gly Glu Ile Ser Pro Ala Ile Gly Asp Leu Lys Ser Leu Leu Ser
                85                  90                  95

Ile Asp Leu Arg Gly Asn Arg Leu Ser Gly Gln Ile Pro Asp Glu Ile
            100                 105                 110

Gly Asp Cys Ser Ser Leu Gln Asn Leu Asp Leu Ser Phe Asn Glu Leu
        115                 120                 125

Ser Gly Asp Ile Pro Phe Ser Ile Ser Lys Leu Lys Gln Leu Glu Gln
    130                 135                 140

Leu Ile Leu Lys Asn Asn Gln Leu Ile Gly Pro Ile Pro Ser Thr Leu
145                 150                 155                 160
```

-continued

```
Ser Gln Ile Pro Asn Leu Lys Ile Leu Asp Leu Ala Gln Asn Lys Leu
                165                 170                 175

Ser Gly Glu Ile Pro Arg Leu Ile Tyr Trp Asn Glu Val Leu Gln Tyr
            180                 185                 190

Leu Gly Leu Arg Gly Asn Asn Leu Val Gly Asn Ile Ser Pro Asp Leu
        195                 200                 205

Cys Gln Leu Thr Gly Leu Trp Tyr Phe Asp Val Arg Asn Asn Ser Leu
    210                 215                 220

Thr Gly Ser Ile Pro Glu Thr Ile Gly Asn Cys Thr Ala Phe Gln Val
225                 230                 235                 240

Leu Asp Leu Ser Tyr Asn Gln Leu Thr Gly Glu Ile Pro Phe Asp Ile
                245                 250                 255

Gly Phe Leu Gln Val Ala Thr Leu Ser Leu Gln Gly Asn Gln Leu Ser
            260                 265                 270

Gly Lys Ile Pro Ser Val Ile Gly Leu Met Gln Ala Leu Ala Val Leu
        275                 280                 285

Asp Leu Ser Gly Asn Leu Leu Ser Gly Ser Ile Pro Pro Ile Leu Gly
    290                 295                 300

Asn Leu Thr Phe Thr Glu Lys Leu Tyr Leu His Ser Asn Lys Leu Thr
305                 310                 315                 320

Gly Ser Ile Pro Pro Glu Leu Gly Asn Met Ser Lys Leu His Tyr Leu
                325                 330                 335

Glu Leu Asn Asp Asn His Leu Thr Gly His Ile Pro Pro Glu Leu Gly
            340                 345                 350

Lys Leu Thr Asp Leu Phe Asp Leu Asn Val Ala Asn Asp Leu Glu
        355                 360                 365

Gly Pro Ile Pro Asp His Leu Ser Ser Cys Thr Asn Leu Asn Ser Leu
    370                 375                 380

Asn Val His Gly Asn Lys Phe Ser Gly Thr Ile Pro Arg Ala Phe Gln
385                 390                 395                 400

Lys Leu Glu Ser Met Thr Tyr Leu Asn Leu Ser Ser Asn Asn Ile Lys
                405                 410                 415

Gly Pro Ile Pro Val Glu Leu Ser Arg Ile Gly Asn Leu Asp Thr Leu
            420                 425                 430

Asp Leu Ser Asn Asn Lys Ile Asn Gly Ile Ile Pro Ser Ser Leu Gly
        435                 440                 445

Asp Leu Glu His Leu Leu Lys Met Asn Leu Ser Arg Asn His Ile Thr
    450                 455                 460

Gly Val Val Pro Gly Asp Phe Gly Asn Leu Arg Ser Ile Met Glu Ile
465                 470                 475                 480

Asp Leu Ser Asn Asn Asp Ile Ser Gly Pro Ile Pro Glu Glu Leu Asn
                485                 490                 495

Gln Leu Gln Asn Ile Ile Leu Leu Arg Leu Glu Asn Asn Leu Thr
            500                 505                 510

Gly Asn Val Gly Ser Leu Ala Asn Cys Leu Ser Leu Thr Val Leu Asn
        515                 520                 525

Val Ser His Asn Asn Leu Val Gly Asp Ile Pro Lys Asn Asn Asn Phe
    530                 535                 540

Ser Arg Phe Ser Pro Asp Ser Phe Ile Gly Asn Pro Gly Leu Cys Gly
545                 550                 555                 560

Ser Trp Leu Asn Ser Pro Cys His Asp Ser Arg Arg Thr Val Arg Val
                565                 570                 575

Ser Ile Ser Arg Ala Ala Ile Leu Gly Ile Ala Ile Gly Gly Leu Val
```

```
                580                 585                 590
Ile Leu Leu Met Val Leu Ile Ala Ala Cys Arg Pro His Asn Pro Pro
            595                 600                 605

Pro Phe Leu Asp Gly Ser Leu Asp Lys Pro Val Thr Tyr Ser Thr Pro
        610                 615                 620

Lys Leu Val Ile Leu His Met Asn Met Ala Leu His Val Tyr Glu Asp
625                 630                 635                 640

Ile Met Arg Met Thr Glu Asn Leu Ser Glu Lys Tyr Ile Ile Gly His
                645                 650                 655

Gly Ala Ser Ser Thr Val Tyr Lys Cys Val Leu Lys Asn Cys Lys Pro
            660                 665                 670

Val Ala Ile Lys Arg Leu Tyr Ser His Asn Pro Gln Ser Met Lys Gln
        675                 680                 685

Phe Glu Thr Glu Leu Glu Met Leu Ser Ser Ile Lys His Arg Asn Leu
    690                 695                 700

Val Ser Leu Gln Ala Tyr Ser Leu Ser His Leu Gly Ser Leu Leu Phe
705                 710                 715                 720

Tyr Asp Tyr Leu Glu Asn Gly Ser Leu Trp Asp Leu Leu His Gly Pro
                725                 730                 735

Thr Lys Lys Thr Leu Asp Trp Asp Thr Arg Leu Lys Ile Ala Tyr
            740                 745                 750

Gly Ala Ala Gln Gly Leu Ala Tyr Leu His His Asp Cys Ser Pro Arg
        755                 760                 765

Ile Ile His Arg Asp Val Lys Ser Ser Asn Ile Leu Leu Asp Lys Asp
    770                 775                 780

Leu Glu Ala Arg Leu Thr Asp Phe Gly Ile Ala Lys Ser Leu Cys Val
785                 790                 795                 800

Ser Lys Ser His Thr Ser Thr Tyr Val Met Gly Thr Ile Gly Tyr Ile
                805                 810                 815

Asp Pro Glu Tyr Ala Arg Thr Ser Arg Leu Thr Glu Lys Ser Asp Val
            820                 825                 830

Tyr Ser Tyr Gly Ile Val Leu Leu Glu Leu Leu Thr Arg Arg Lys Ala
        835                 840                 845

Val Asp Asp Glu Ser Asn Leu His His Leu Ile Met Ser Lys Thr Gly
    850                 855                 860

Asn Asn Glu Val Met Glu Met Ala Asp Pro Asp Ile Thr Ser Thr Cys
865                 870                 875                 880

Lys Asp Leu Gly Val Val Lys Lys Val Phe Gln Leu Ala Leu Leu Cys
                885                 890                 895

Thr Lys Arg Gln Pro Asn Asp Arg Pro Thr Met His Gln Val Thr Arg
            900                 905                 910

Val Leu Gly Ser Phe Met Leu Ser Glu Gln Pro Pro Ala Ala Thr Asp
        915                 920                 925

Thr Ser Ala Thr Leu Ala Gly Ser Cys Tyr Val Asp Glu Tyr Ala Asn
    930                 935                 940

Leu Lys Thr Pro His Ser Val Asn Cys Ser Ser Met Ser Ala Ser Asp
945                 950                 955                 960

Ala Gln Leu Phe Leu Arg Phe Gly Gln Val Ile Ser Gln Asn Ser Glu
                965                 970                 975

<210> SEQ ID NO 3
<211> LENGTH: 2901
<212> TYPE: DNA
<213> ORGANISM: Arabidopsis thaliana
```

<400> SEQUENCE: 3

```
atgaaggaga agatgcagcg aatggtttta tctttagcaa tggtgggttt tatggttttt      60
ggtgttgctt cggctatgaa caacgaaggg aaagctctga tggcgataaa aggctctttc     120
agcaacttag tgaatatgct tttggattgg gacgatgttc acaacagtga cttgtgttct     180
tggcgaggtg ttttctgcga caacgttagc tactccgttg tctctctgaa tttgtccagt     240
ctgaatcttg gagggagat atctccagct attggagacc tacggaattt gcaatcaata      300
gacttgcaag gtaataaact agcaggtcaa attccagatg agattggaaa ctgtgcttct     360
cttgtttatc tggatttgtc cgagaatctg ttatatggag acatacccttt ctcaatctct    420
aaactcaagc agcttgaaac tctgaatctg aagaacaatc agctcacagg tcctgtacca     480
gcaaccttaa cccagattcc aaaccttaag agacttgatc ttgctggcaa tcatctaacg     540
ggtgagatat cgagattgct ttactggaat gaagttttgc agtatcttgg attacgaggg     600
aatatgttga ctggaacgtt atcttctgat atgtgtcagc taaccggttt gtggtacttt     660
gatgtgagag gaataatct aactggaacc atcccggaga gcatcggaaa ttgcacaagc      720
tttcaaatcc tggacatatc ttataatcag ataacaggag agattcctta caatatcggc     780
ttcctccaag ttgctactct gtcacttcaa ggaaacagat tgacgggtag aattccagaa     840
gttattggtc taatgcaggc tcttgctgtt ttggatttga gtgacaatga gcttgttggt     900
cctatcccac cgatacttgg caatctctca tttaccggaa agttgtatct ccatggcaat     960
atgctcactg gtccaatccc ctctgagctt ggaaatatgt cacgtctcag ctatttgcag   1020
ctaaacgaca taaactagt gggaactatt ccacctgagc ttggaaagct ggagcaattg    1080
tttgaactga atcttgccaa caaccgttta gtagggccca taccatccaa cattagttca   1140
tgtgcagcct tgaatcaatt caatgttcat gggaacctct gagtggatc tattccactg    1200
gcgtttcgca atctcgggag cttgacttat ctgaatcttt cgtcgaacaa tttcaaggga   1260
aaaataccag ttgagcttgg acatataatc aatcttgaca aactagatct gtctggcaat   1320
aacttctcag gtctatacc attaacgctt ggcgatcttg aacaccttct catattaaat    1380
cttagcagaa accatcttag tggacaatta cctgcagagt ttgggaaccct tcgaagcatt   1440
cagatgatta tgtatcatt caatctgctc tccggagtta ttccaactga acttggccaa   1500
ttgcagaatt taaactcttt aatattgaac aacaacaagc ttcatgggaa aattccagat   1560
cagcttacga actgcttcac tcttgtcaat ctgaatgtct ccttcaacaa tctctccggg   1620
atagtcccac caatgaaaaa cttctcacgt tttgctccag ccagctttgt tggaaatcca   1680
tatctttgtg gaaactgggt tggatctatt tgtggtccctt taccgaaatc tcgagtattc   1740
tccagaggtg ctttgatctg cattgttctt ggcgtcatca ctctcctatg tatgattttc   1800
cttgcagttt acaaatcaat gcagcagaag aagattctac aaggctcctc aaaacaagct   1860
gaagggttaa ccaagctagt gattctccac atggacatgg caattcatac atttgatgat   1920
atcatgagag tgactgagaa tcttaacgaa aagtttataa ttggatatgg tgcttctagc   1980
acggtataca aatgtgcatt aaaaagttcc cgacctattg ccattaagcg actctacaat   2040
cagtatccgc ataacttgcg ggaatttgag acagaacttg agaccattgg gagcattagg   2100
cacagaaaca tagtcagctt gcatggatat gccttgtctc ctactggcaa ccttcttttc   2160
tatgactaca tggaaaatgg atcactttgg gaccttcttc atgggtcatt gaagaaagtg   2220
aagcttgatt gggagacaag gttgaagata gcggttggag ctgcacaagg actagcctat   2280
```

-continued

```
cttcaccacg attgtactcc tcgaatcatt caccgtgaca tcaagtcatc gaacatactt    2340
cttgatgaga atttcgaagc acatttatct gatttcggga ttgctaagag cataccagct    2400
agcaaaaccc atgcctcgac ttatgttttg ggaacaattg gttatataga cccagagtat    2460
gctcgtactt cacgaatcaa tgagaaatcc gatatataca gcttcggtat tgttcttctt    2520
gagcttctca ctgggaagaa agcagtggat aacgaagcta acttgcatca actgatattg    2580
tcaaaggctg atgataatac tgtgatgaa gcagttgatc cagaggttac tgtgacttgt    2640
atggacttgg gacatatcag gaagacattt cagctggctc tcttatgcac aaagcgaaac    2700
cctttagaga gacccacaat gcttgaagtc tctagggttc tgctctctct tgtcccatct    2760
ctgcaagtag caaagaagct accttctctt gatcactcaa ccaaaaagct gcagcaagag    2820
aatgaagtta ggaatcctga tgcagaagca tctcaatggt ttgttcagtt ccgtgaagtc    2880
atctccaaaa gtagcatata a                                              2901
```

<210> SEQ ID NO 4
<211> LENGTH: 966
<212> TYPE: PRT
<213> ORGANISM: Arabidopsis thaliana

<400> SEQUENCE: 4

```
Met Lys Glu Lys Met Gln Arg Met Val Leu Ser Leu Ala Met Val Gly
  1               5                  10                  15

Phe Met Val Phe Gly Val Ala Ser Ala Met Asn Asn Glu Gly Lys Ala
                 20                  25                  30

Leu Met Ala Ile Lys Gly Ser Phe Ser Asn Leu Val Asn Met Leu Leu
             35                  40                  45

Asp Trp Asp Asp Val His Asn Ser Asp Leu Cys Ser Trp Arg Gly Val
         50                  55                  60

Phe Cys Asp Asn Val Ser Tyr Ser Val Val Ser Leu Asn Leu Ser Ser
 65                  70                  75                  80

Leu Asn Leu Gly Gly Glu Ile Ser Pro Ala Ile Gly Asp Leu Arg Asn
                 85                  90                  95

Leu Gln Ser Ile Asp Leu Gln Gly Asn Lys Leu Ala Gly Gln Ile Pro
            100                 105                 110

Asp Glu Ile Gly Asn Cys Ala Ser Leu Val Tyr Leu Asp Leu Ser Glu
        115                 120                 125

Asn Leu Leu Tyr Gly Asp Ile Pro Phe Ser Ile Ser Lys Leu Lys Gln
    130                 135                 140

Leu Glu Thr Leu Asn Leu Lys Asn Asn Gln Leu Thr Gly Pro Val Pro
145                 150                 155                 160

Ala Thr Leu Thr Gln Ile Pro Asn Leu Lys Arg Leu Asp Leu Ala Gly
                165                 170                 175

Asn His Leu Thr Gly Glu Ile Ser Arg Leu Leu Tyr Trp Asn Glu Val
            180                 185                 190

Leu Gln Tyr Leu Gly Leu Arg Gly Asn Met Leu Thr Gly Thr Leu Ser
        195                 200                 205

Ser Asp Met Cys Gln Leu Thr Gly Leu Trp Tyr Phe Asp Val Arg Gly
    210                 215                 220

Asn Asn Leu Thr Gly Thr Ile Pro Glu Ser Ile Gly Asn Cys Thr Ser
225                 230                 235                 240

Phe Gln Ile Leu Asp Ile Ser Tyr Asn Gln Ile Thr Gly Glu Ile Pro
                245                 250                 255

Tyr Asn Ile Gly Phe Leu Gln Val Ala Thr Leu Ser Leu Gln Gly Asn
```

-continued

```
                260                 265                 270
Arg Leu Thr Gly Arg Ile Pro Glu Val Ile Gly Leu Met Gln Ala Leu
            275                 280                 285
Ala Val Leu Asp Leu Ser Asp Asn Glu Leu Val Gly Pro Ile Pro Pro
            290                 295                 300
Ile Leu Gly Asn Leu Ser Phe Thr Gly Lys Leu Tyr Leu His Gly Asn
305                 310                 315                 320
Met Leu Thr Gly Pro Ile Pro Ser Glu Leu Gly Asn Met Ser Arg Leu
                325                 330                 335
Ser Tyr Leu Gln Leu Asn Asp Asn Lys Leu Val Gly Thr Ile Pro Pro
            340                 345                 350
Glu Leu Gly Lys Leu Glu Gln Leu Phe Glu Leu Asn Leu Ala Asn Asn
            355                 360                 365
Arg Leu Val Gly Pro Ile Pro Ser Asn Ile Ser Ser Cys Ala Ala Leu
            370                 375                 380
Asn Gln Phe Asn Val His Gly Asn Leu Leu Ser Gly Ser Ile Pro Leu
385                 390                 395                 400
Ala Phe Arg Asn Leu Gly Ser Leu Thr Tyr Leu Asn Leu Ser Ser Asn
                405                 410                 415
Asn Phe Lys Gly Lys Ile Pro Val Glu Leu Gly His Ile Ile Asn Leu
            420                 425                 430
Asp Lys Leu Asp Leu Ser Gly Asn Asn Phe Ser Gly Ser Ile Pro Leu
            435                 440                 445
Thr Leu Gly Asp Leu Glu His Leu Leu Ile Leu Asn Leu Ser Arg Asn
            450                 455                 460
His Leu Ser Gly Gln Leu Pro Ala Glu Phe Gly Asn Leu Arg Ser Ile
465                 470                 475                 480
Gln Met Ile Asp Val Ser Phe Asn Leu Leu Ser Gly Val Ile Pro Thr
                485                 490                 495
Glu Leu Gly Gln Leu Gln Asn Leu Asn Ser Leu Ile Leu Asn Asn Asn
            500                 505                 510
Lys Leu His Gly Lys Ile Pro Asp Gln Leu Thr Asn Cys Phe Thr Leu
            515                 520                 525
Val Asn Leu Asn Val Ser Phe Asn Asn Leu Ser Gly Ile Val Pro Pro
            530                 535                 540
Met Lys Asn Phe Ser Arg Phe Ala Pro Ala Ser Phe Val Gly Asn Pro
545                 550                 555                 560
Tyr Leu Cys Gly Asn Trp Val Gly Ser Ile Cys Gly Pro Leu Pro Lys
                565                 570                 575
Ser Arg Val Phe Ser Arg Gly Ala Leu Ile Cys Ile Val Leu Gly Val
            580                 585                 590
Ile Thr Leu Leu Cys Met Ile Phe Leu Ala Val Tyr Lys Ser Met Gln
            595                 600                 605
Gln Lys Lys Ile Leu Gln Gly Ser Ser Lys Gln Ala Glu Gly Leu Thr
            610                 615                 620
Lys Leu Val Ile Leu His Met Asp Met Ala Ile His Thr Phe Asp Asp
625                 630                 635                 640
Ile Met Arg Val Thr Glu Asn Leu Asn Glu Lys Phe Ile Ile Gly Tyr
                645                 650                 655
Gly Ala Ser Ser Thr Val Tyr Lys Cys Ala Leu Lys Ser Ser Arg Pro
            660                 665                 670
Ile Ala Ile Lys Arg Leu Tyr Asn Gln Tyr Pro His Asn Leu Arg Glu
            675                 680                 685
```

```
Phe Glu Thr Glu Leu Glu Thr Ile Gly Ser Ile Arg His Arg Asn Ile
            690                 695                 700

Val Ser Leu His Gly Tyr Ala Leu Ser Pro Thr Gly Asn Leu Leu Phe
705                 710                 715                 720

Tyr Asp Tyr Met Glu Asn Gly Ser Leu Trp Asp Leu Leu His Gly Ser
                725                 730                 735

Leu Lys Lys Val Lys Leu Asp Trp Glu Thr Arg Leu Lys Ile Ala Val
            740                 745                 750

Gly Ala Ala Gln Gly Leu Ala Tyr Leu His His Asp Cys Thr Pro Arg
        755                 760                 765

Ile Ile His Arg Asp Ile Lys Ser Ser Asn Ile Leu Leu Asp Glu Asn
770                 775                 780

Phe Glu Ala His Leu Ser Asp Phe Gly Ile Ala Lys Ser Ile Pro Ala
785                 790                 795                 800

Ser Lys Thr His Ala Ser Thr Tyr Val Leu Gly Thr Ile Gly Tyr Ile
                805                 810                 815

Asp Pro Glu Tyr Ala Arg Thr Ser Arg Ile Asn Glu Lys Ser Asp Ile
            820                 825                 830

Tyr Ser Phe Gly Ile Val Leu Leu Glu Leu Thr Gly Lys Lys Ala
        835                 840                 845

Val Asp Asn Glu Ala Asn Leu His Gln Leu Ile Leu Ser Lys Ala Asp
850                 855                 860

Asp Asn Thr Val Met Glu Ala Val Asp Pro Glu Val Thr Val Thr Cys
865                 870                 875                 880

Met Asp Leu Gly His Ile Arg Lys Thr Phe Gln Leu Ala Leu Leu Cys
                885                 890                 895

Thr Lys Arg Asn Pro Leu Glu Arg Pro Thr Met Leu Glu Val Ser Arg
            900                 905                 910

Val Leu Leu Ser Leu Val Pro Ser Leu Gln Val Ala Lys Lys Leu Pro
        915                 920                 925

Ser Leu Asp His Ser Thr Lys Lys Leu Gln Gln Glu Asn Glu Val Arg
930                 935                 940

Asn Pro Asp Ala Glu Ala Ser Gln Trp Phe Val Gln Phe Arg Glu Val
945                 950                 955                 960

Ile Ser Lys Ser Ser Ile
                965

<210> SEQ ID NO 5
<211> LENGTH: 3533
<212> TYPE: DNA
<213> ORGANISM: Zea mays

<400> SEQUENCE: 5
cctacgctgc cactctatcg cccagccata cagcagctac cccgctgcct gtcactgagc      60
cagcgcggcg caagtgcgca aagccgagcg cgagaaccca cgaaaccaac ccagagcccc     120
cattaaggca ggctcgctgc agcacgtctc gcgctccatc gccgcctgtc ctcttcctgt     180
aatgtcactc ccccgatgcc tgtgcgcagc tcagtggcca tgacgacgac ggccgcccgt     240
gctctcgccg ccctcgtgct cgtcaccgcc gccgccgccg ccgccgccgt cgccgacgat     300
ggggcggcgc tggtggagat caagaagtcc ttccgcaacg tcggcaacgt actgtacgat     360
tgggccggcg acgactactg ctcctggcgc ggcgtcctgt gcgacaacgt cacgttcgcc     420
gtcgccgcgc tcaacctctc tggcctcaac cttgagggtg agatctctcc agccgtcggc     480
```

```
agcctcaaga gcctcgtctc catcgacctc aagtcaaatg ccctatccgg gcagatccct    540
gatgagattg gcgattgttc gtcacttagg acgctggact tttcattcaa caacttggac    600
ggcgacatac cattttcaat atcaaagctg aagcacctgg agaacttgat attgaagaac    660
aaccggctga ttggtgcgat cccctcaaca ttgtcacagc tcccaaattt gaagattctg    720
gacttggcac aaaacaaact gactggggag ataccgaggc ttatctattg aacgaggtt    780
cttcaatact tgggtttgcg gggaaatcat ttagaaggaa gcctctctcc tgatatgtgc    840
cagcttactg gcctttggta ctttgatgtg aagaacaata gtttgactgg ggcgatacca    900
gacaccattg gaactgtac aagttttcag gtcttggatt tgtcttacaa ccgctttact    960
ggaccaatcc cattcaacat tggtttccta caagtggcta cactatcctt gcaagggaac   1020
aagttcactg gcccaattcc ttcagtaatt ggccttatgc aggctctcgc tgtcctagat   1080
ctgagttaca accaattatc tggtcctata ccatctatac taggcaactt gacatacact   1140
gagaagctgt acatgcaagg caacaggtta actggatcga taccaccaga gctaggaaat   1200
atgtcaacac ttcattacct agaactgaat gataatcaac ttactgggtc aattccacca   1260
gagcttggaa ggctaacagg cttgtttgac ctgaaccctg cgaataacca ccttgaagga   1320
ccaattcctg acaacctaag ttcatgtgtg aatctcaata gcttcaatgc ttatggcaac   1380
aagttaaatg gaaccattcc tcgttcgctg cggaaacttg aaagcatgac ctatttaaat   1440
ctttcatcaa atttcataag tggttctatt cctattgagc tatcaaggat caacaatttg   1500
gacacgttgg gcttatcctg taacatgatg acgggtccaa ttccatcatc cattggcaac   1560
ctagagcatc tattgaggct taacttgagc aagaatgatc tagttggatt catccctgcg   1620
gagtttggta atttgggaag tgtcatggag attgatttat cctataatca tcttggtggt   1680
ctgattcctc aagaacttgg aatgctgcaa aacctgatgt tgctaaaact ggaaaacaac   1740
aatataactg gcgatgtctc ttctctgatg aactgcttca gcctcaatat cttaaatgtg   1800
tcatacaata atttagctgg tgctgtccct actgacaaca acttcacacg ttttcacat   1860
gacagctttt taggtaatcc tggactctgt ggatattggc ttggttcttc atgtcgttcc   1920
actggccacc gagacaaacc gccaatctca aaggctgcca taattggtgt tgctgtgggt   1980
ggacttgtta tcctcctgat gatcttagta gctgtatgca ggccacacca tccacctgct   2040
tttaaagatg ccactgtaag caagccagtg agcaatggtc cacccaagct gatgatcctt   2100
catatgaaca tggctcttca tgtctttgat gatataatga ggatgactga gaacttgagt   2160
gagaaataca tcattggata cggggcatca agtacagttt ataaatgtgt tctaaagaat   2220
tgcaaaccag tggcaataaa aaagctgtat gcccactacc ctcagagcct taaggaattt   2280
gaaactgagc tcgagactgt tggtagcatc aaacaccgga atctagtcag ccttcaaggg   2340
tactcgttgt cacctgttgg gaacctcctc ttttatgatt atatggagag tggcagctta   2400
tgggatgttt tacatgaagg ctcatccaag gagaacaaac ttgactgggt gactcgccta   2460
cggatcgctc ttggtgcagc tcaaggcctc gcttaccttc accatgactg cagcccacga   2520
ataattcacc gggacgtaaa atcaaagaat atactcctcg acaaagatta tgaggcccat   2580
cttacagact tcggcatcgc taagagctta tgtgtctcga agactcacac gtcaacctac   2640
gtcatgggca ctattggtta cattgatccc gagtacgccc gcacctcccg cctcaacgag   2700
aagtctgatg tctacagcta cggcatcgtt ctgctggagc tgctgaccgg caagaagcca   2760
gtggacaacg agtgcaatct ccatcacttg atcctatcga agacggcgag caacgaggtc   2820
atggagacgg tggaccccga cgtgggagac acctgcaagg acctgggcga ggtgaagaag   2880
```

```
ctgttccagc tggcgctcct ctgcaccaag cggcagccct cggaccggcc gacgatgcac    2940
gaggtggtgc gcgtccttga ctgcctggtg aacccggagc cgccgccgca gccgcagcag    3000
cagcagcaga aggcgcacgc gcaccaccag ctgccgccgc agccgtcgcc gccggcctac    3060
gtcgacgagt acgtcagcct gcggggcacc ggcgccctct cctgcgccaa ctcgtccagc    3120
acctcggacg ccgagctgtt cctcaagttc ggcgaggcca tctcgcagaa catggtgtag    3180
gggaagacgt agacgttcgg tgaggcgcct tgagtgaggc cgattgcagg gggagtagtt    3240
tgactgacat tttgtgggac gcagcgcagg agattaacat gggactcagt agctagggtg    3300
ttgttagctg taaaaaaagt catgtgacgc aagagcagcg gagcttcttc ctcttcttta    3360 tccccctcc ccattttct tggtggtct aacttactag gaggctgtat tgatccatca       3420
tcatctctcc cgttcctctg cttgatgatc ttttgtgact ttcgcggtcc tctgtattga    3480
tccatgatct tttgtgacct ctgctttatt ttctgggatc tttacctcag aac           3533
```

<210> SEQ ID NO 6
<211> LENGTH: 994
<212> TYPE: PRT
<213> ORGANISM: Zea mays

<400> SEQUENCE: 6

```
Met Pro Val Arg Ser Ser Val Ala Met Thr Thr Thr Ala Ala Arg Ala
 1               5                  10                  15

Leu Ala Ala Leu Val Leu Val Thr Ala Ala Ala Ala Ala Ala Ala Val
                20                  25                  30

Ala Asp Asp Gly Ala Ala Leu Val Glu Ile Lys Lys Ser Phe Arg Asn
            35                  40                  45

Val Gly Asn Val Leu Tyr Asp Trp Ala Gly Asp Tyr Cys Ser Trp
    50                  55                  60

Arg Gly Val Leu Cys Asp Asn Val Thr Phe Ala Val Ala Ala Leu Asn
65                  70                  75                  80

Leu Ser Gly Leu Asn Leu Glu Gly Glu Ile Ser Pro Ala Val Gly Ser
                85                  90                  95

Leu Lys Ser Leu Val Ser Ile Asp Leu Lys Ser Asn Gly Leu Ser Gly
            100                 105                 110

Gln Ile Pro Asp Glu Ile Gly Asp Cys Ser Ser Leu Arg Thr Leu Asp
        115                 120                 125

Phe Ser Phe Asn Asn Leu Asp Gly Asp Ile Pro Phe Ser Ile Ser Lys
    130                 135                 140

Leu Lys His Leu Glu Asn Leu Ile Leu Lys Asn Asn Arg Leu Ile Gly
145                 150                 155                 160

Ala Ile Pro Ser Thr Leu Ser Gln Leu Pro Asn Leu Lys Ile Leu Asp
                165                 170                 175

Leu Ala Gln Asn Lys Leu Thr Gly Glu Ile Pro Arg Leu Ile Tyr Trp
            180                 185                 190

Asn Glu Val Leu Gln Tyr Leu Gly Leu Arg Gly Asn His Leu Glu Gly
        195                 200                 205

Ser Leu Ser Pro Asp Met Cys Gln Leu Thr Gly Leu Trp Tyr Phe Asp
    210                 215                 220

Val Lys Asn Asn Ser Leu Thr Gly Ala Ile Pro Asp Thr Ile Gly Asn
225                 230                 235                 240

Cys Thr Ser Phe Gln Val Leu Asp Leu Ser Tyr Asn Arg Phe Thr Gly
                245                 250                 255
```

-continued

```
Pro Ile Pro Phe Asn Ile Gly Phe Leu Gln Val Ala Thr Leu Ser Leu
            260                 265                 270
Gln Gly Asn Lys Phe Thr Gly Pro Ile Pro Ser Val Ile Gly Leu Met
        275                 280                 285
Gln Ala Leu Ala Val Leu Asp Leu Ser Tyr Asn Gln Leu Ser Gly Pro
    290                 295                 300
Ile Pro Ser Ile Leu Gly Asn Leu Thr Tyr Thr Glu Lys Leu Tyr Met
305                 310                 315                 320
Gln Gly Asn Arg Leu Thr Gly Ser Ile Pro Glu Leu Gly Asn Met
            325                 330                 335
Ser Thr Leu His Tyr Leu Glu Leu Asn Asp Asn Gln Leu Thr Gly Ser
            340                 345                 350
Ile Pro Pro Glu Leu Gly Arg Leu Thr Gly Leu Phe Asp Leu Asn Pro
            355                 360                 365
Ala Asn Asn His Leu Glu Gly Pro Ile Pro Asp Asn Leu Ser Ser Cys
        370                 375                 380
Val Asn Leu Asn Ser Phe Asn Ala Tyr Gly Asn Lys Leu Asn Gly Thr
385                 390                 395                 400
Ile Pro Arg Ser Leu Arg Lys Leu Glu Ser Met Thr Tyr Leu Asn Leu
            405                 410                 415
Ser Ser Asn Phe Ile Ser Gly Ser Ile Pro Ile Glu Leu Ser Arg Ile
        420                 425                 430
Asn Asn Leu Asp Thr Leu Gly Leu Ser Cys Asn Met Met Thr Gly Pro
    435                 440                 445
Ile Pro Ser Ser Ile Gly Asn Leu Glu His Leu Leu Arg Leu Asn Leu
    450                 455                 460
Ser Lys Asn Asp Leu Val Gly Phe Ile Pro Ala Glu Phe Gly Asn Leu
465                 470                 475                 480
Gly Ser Val Met Glu Ile Asp Leu Ser Tyr Asn His Leu Gly Gly Leu
            485                 490                 495
Ile Pro Gln Glu Leu Gly Met Leu Gln Asn Leu Met Leu Leu Lys Leu
        500                 505                 510
Glu Asn Asn Asn Ile Thr Gly Asp Val Ser Ser Leu Met Asn Cys Phe
    515                 520                 525
Ser Leu Asn Ile Leu Asn Val Ser Tyr Asn Asn Leu Ala Gly Ala Val
    530                 535                 540
Pro Thr Asp Asn Asn Phe Thr Arg Phe Ser His Asp Ser Phe Leu Gly
545                 550                 555                 560
Asn Pro Gly Leu Cys Gly Tyr Trp Leu Gly Ser Ser Cys Arg Ser Thr
            565                 570                 575
Gly His Arg Asp Lys Pro Ile Ser Lys Ala Ala Ile Ile Gly Val
        580                 585                 590
Ala Val Gly Gly Leu Val Ile Leu Leu Met Ile Leu Val Ala Val Cys
    595                 600                 605
Arg Pro His His Pro Ala Phe Lys Asp Ala Thr Val Ser Lys Pro
    610                 615                 620
Val Ser Asn Gly Pro Pro Lys Leu Met Ile Leu His Met Asn Met Ala
625                 630                 635                 640
Leu His Val Phe Asp Asp Ile Met Arg Met Thr Glu Asn Leu Ser Glu
            645                 650                 655
Lys Tyr Ile Ile Gly Tyr Gly Ala Ser Ser Thr Val Tyr Lys Cys Val
            660                 665                 670
Leu Lys Asn Cys Lys Pro Val Ala Ile Lys Lys Leu Tyr Ala His Tyr
```

-continued

```
                675                 680                 685
Pro Gln Ser Leu Lys Glu Phe Glu Thr Glu Leu Glu Thr Val Gly Ser
    690                 695                 700

Ile Lys His Arg Asn Leu Val Ser Leu Gln Gly Tyr Ser Leu Ser Pro
705                 710                 715                 720

Val Gly Asn Leu Leu Phe Tyr Asp Tyr Met Glu Ser Gly Ser Leu Trp
                725                 730                 735

Asp Val Leu His Glu Gly Ser Ser Lys Glu Asn Lys Leu Asp Trp Val
            740                 745                 750

Thr Arg Leu Arg Ile Ala Leu Gly Ala Ala Gln Gly Leu Ala Tyr Leu
        755                 760                 765

His His Asp Cys Ser Pro Arg Ile Ile His Arg Asp Val Lys Ser Lys
    770                 775                 780

Asn Ile Leu Leu Asp Lys Asp Tyr Glu Ala His Leu Thr Asp Phe Gly
785                 790                 795                 800

Ile Ala Lys Ser Leu Cys Val Ser Lys Thr His Thr Ser Thr Tyr Val
                805                 810                 815

Met Gly Thr Ile Gly Tyr Ile Asp Pro Glu Tyr Ala Arg Thr Ser Arg
            820                 825                 830

Leu Asn Glu Lys Ser Asp Val Tyr Ser Tyr Gly Ile Val Leu Leu Glu
        835                 840                 845

Leu Leu Thr Gly Lys Lys Pro Val Asp Asn Glu Cys Asn Leu His His
    850                 855                 860

Leu Ile Leu Ser Lys Thr Ala Ser Asn Glu Val Met Glu Thr Val Asp
865                 870                 875                 880

Pro Asp Val Gly Asp Thr Cys Lys Asp Leu Gly Glu Val Lys Lys Leu
                885                 890                 895

Phe Gln Leu Ala Leu Leu Cys Thr Lys Arg Gln Pro Ser Asp Arg Pro
            900                 905                 910

Thr Met His Glu Val Val Arg Val Leu Asp Cys Leu Val Asn Pro Glu
        915                 920                 925

Pro Pro Pro Gln Pro Gln Gln Gln Gln Lys Ala His Ala His His
    930                 935                 940

Gln Leu Pro Pro Gln Pro Ser Pro Ala Tyr Val Asp Glu Tyr Val
945                 950                 955                 960

Ser Leu Arg Gly Thr Gly Ala Leu Ser Cys Ala Asn Ser Ser Ser Thr
                965                 970                 975

Ser Asp Ala Glu Leu Phe Leu Lys Phe Gly Glu Ala Ile Ser Gln Asn
            980                 985                 990

Met Val

<210> SEQ ID NO 7
<211> LENGTH: 3224
<212> TYPE: DNA
<213> ORGANISM: Zea mays

<400> SEQUENCE: 7
gagaaacact gctggagatc aagaaatcct tccgcgacgg cggcaacgcg ctgtacgatt    60
ggtccggcga cggcgcgtcg ccgggctact gctcgtggcg cggcgtgcta tgcgacaacg   120
tcaccttcgc tgtcgcggcg ctcaacctct ctgggctcaa tctcgagggt gaaatctcag   180
cggccatcgg gagtctgcaa cgtcttgtct caatcgattt gaagtcgaat ggactctctg   240
gacagatccc cgatgagatt ggtgattgtt ctttgctcga aactttggat ttgtcatcta   300
```

```
acaatctaga aggagacata ccattctcca tgtccaagct gaagcacctt gagaacttga      360 tttttgaagaa caacaaactg gtgggagtga tcccatcgac actctctcaa cttccaaatt     420
tgaagatatt ggacttggct caaaacaagt taagtggtga aattccgaat ctaatatatt     480
ggaatgaggt tcttcaatac ttgggattgc gaagcaatag tttagaagga agcctctctc    540
ccgatatgtg ccagttaact ggtctgtggt actttgatgt gaagaacaat agcttgacgg    600
gtgcaatacc agaaaccata gggaactgta cgagctttca ggtcttagat ttgtcaaaca    660
atcatcttac tggagaaatc ccgttcaata ttggtttcct gcaagtggct acgttatctt   720
tgcaagggaa caagttctct ggtcctatac catcagtgat tggcccttatg caggcgcttg   780 cagtgctaga tctgagtttc aatgagctat ctggcccaat accctctata ctgggcaact    840
tgacatacac tgagaaatta tacctgcaag gcaataggtt aactggattg ataccgccag    900
agcttggtaa tatgtcgaca ctgcattacc tggaactgaa cgacaatctg ttgactgggt    960
tcattcctcc tgatcttgga aaacttacag aattgtttga attgaaccctt gcaaacaaca  1020 accttatagg acctatccct gagaatttaa gttcatgtgc aaatctcatt agtttcaatg   1080
cttatggcaa taaattgaat ggaaccattc cacgttcatt tcacaagctt gagagtctga   1140
cttatctgaa tctgtcatca aatcatctca gtggagcact tccaattgag gttgcaagaa   1200
tgagaaattt ggacactctg gacttatcct gtaacatgat cactggttca attccctcgg   1260
ctattgggaa actagagcat cttttgaggc tcaacttaag caaaaataat gtggctggac   1320
acattcctgc tgaatttggg aacttaagga gcatcatgga gattgatttg tcttacaacc   1380
acctcagtgg cctgattcct caagaggttg ggatgctaca aaatttgata ctgttaaaat   1440
tagaaagcaa taatattact ggagatgtct cttcacttat ttactgcttg agtctcaata   1500
tcttaaatgt atcatacaac catctttatg gtactgtacc tacagacaac aacttctcac   1560
gattttcacc cgacagcttc ttgggtaacc ctggactttg tggctattgg cttcactctg   1620
cttcatgcac acaattatcc aatgcagagc aaatgaagag atcctctagc gcaaaggcct   1680
caatgtttgc agctattggt gttggtgccg tattgcttgt tattatgctc gttatcctag   1740
tagttatttg ctggccacat aactctccag tgctcaaaga tgtctctgta aacaaaccag   1800
ataaccttgc ttcagcatca aacaacattc atcccaagct tgtgatcctc cacatgaaca   1860
tggccctcta tgtatatgat gatataatga ggatgactga aaacttgagc gaaaaataca   1920
ttattggtta tggagcctca agtacagtct acagatgcga cctgaagaac tgcaagccaa   1980
ttgcgattaa aaagctgtat gctcactacc ctcagagctt gaaggaattc gagactgaac   2040
ttgagactgt tggaagcatc aaacaccgga atcttgtaag ccttcagggg tactccctgt   2100
caccatctgg gaatctcctc ttctatgatt acatggaaaa tggcagcctc tgggacattt   2160
tacatgcttc atcgaagaaa aagaaactcg attgggaggc tcgcctcaag attgctctcg   2220
gagctgctca aggcctggct tatcttcacc atgaatgcag tccacgaata atccacaggg   2280
atgtgaagtc aaagaatatc ctcctagaca aagactacga ggctcatctt gctgacttcg   2340
gtattgccaa gagcttgtgt gtgtcgaaga cgcacacatc aacgtacgtg atgggcacca   2400
ttggctacat tgaccctgag tatgcacgga catcccggat caacgagaaa tcggatgtgt   2460
acagctacgg cattgtcttg ctggagctgc ttaccggcaa aaagcctgtc gacgacgagt   2520
gcaaccttca ccacttgatc ctatccaaag ccgcagaaaa cacggtcatg gagacggtag   2580
accaggacat caccgacacg tgcaaggacc tcggcgaggt caagaaggtg ttccagctgg   2640
cgctcctttg cagcaagagg cagccgtcgg atcgaccgac catgcacgag gtcgcgcgcg   2700
```

-continued

```
tcctggacag cctcgtctgc ccagcaggcc cgcccccgaa gcaggcgcag gcgcaggcac    2760
aggcacaggc gtcggagaag ccgtccacca cggcgccgag ctatgtcagc gagtacgtcg    2820
gcctacgagg cggcggcggc ggcagcgccc tctcctgcac caactcgtcg agcgcgtccg    2880
acgccgagct cttcatgaag tttggcgagg tgatctcgcg gagcacggaa tagtccaata    2940
gatcgacgat cattttgtgt tacagtttac aataggtgtc tggccggcgc cctgtgatgt    3000
gactcgctgt aaatatgctg ctgccttctc gttgggactc cactaggcac tagtagctat    3060
ttttctccgt tatgcacgtc tctctctttt tttttgctgg gaaactcgaa ctgtaactaa    3120
aggaatggat ttatgtgcag gctgcgttta ctgacaaaaa aaaaaaaaaa aaaaaaaaa     3180 aaaaaaaaa  aaaaaaaaaa aaaaaaaaaa aaaaaaaaaa aaaa                    3224
```

<210> SEQ ID NO 8
<211> LENGTH: 976
<212> TYPE: PRT
<213> ORGANISM: Zea mays

<400> SEQUENCE: 8

```
Glu Thr Leu Leu Glu Ile Lys Lys Ser Phe Arg Asp Gly Gly Asn Ala
 1               5                   10                  15

Leu Tyr Asp Trp Ser Gly Asp Gly Ala Ser Pro Gly Tyr Cys Ser Trp
             20                  25                  30

Arg Gly Val Leu Cys Asp Asn Val Thr Phe Ala Val Ala Ala Leu Asn
         35                  40                  45

Leu Ser Gly Leu Asn Leu Glu Gly Glu Ile Ser Ala Ala Ile Gly Ser
     50                  55                  60

Leu Gln Arg Leu Val Ser Ile Asp Leu Lys Ser Asn Gly Leu Ser Gly
 65                  70                  75                  80

Gln Ile Pro Asp Glu Ile Gly Asp Cys Ser Leu Leu Glu Thr Leu Asp
                 85                  90                  95

Leu Ser Ser Asn Asn Leu Glu Gly Asp Ile Pro Phe Ser Met Ser Lys
            100                 105                 110

Leu Lys His Leu Glu Asn Leu Ile Leu Lys Asn Asn Lys Leu Val Gly
        115                 120                 125

Val Ile Pro Ser Thr Leu Ser Gln Leu Pro Asn Leu Lys Ile Leu Asp
    130                 135                 140

Leu Ala Gln Asn Lys Leu Ser Gly Glu Ile Pro Asn Leu Ile Tyr Trp
145                 150                 155                 160

Asn Glu Val Leu Gln Tyr Leu Gly Leu Arg Ser Asn Ser Leu Glu Gly
                165                 170                 175

Ser Leu Ser Pro Asp Met Cys Gln Leu Thr Gly Leu Trp Tyr Phe Asp
            180                 185                 190

Val Lys Asn Asn Ser Leu Thr Gly Ala Ile Pro Glu Thr Ile Gly Asn
        195                 200                 205

Cys Thr Ser Phe Gln Val Leu Asp Leu Ser Asn Asn His Leu Thr Gly
    210                 215                 220

Glu Ile Pro Phe Asn Ile Gly Phe Leu Gln Val Ala Thr Leu Ser Leu
225                 230                 235                 240

Gln Gly Asn Lys Phe Ser Gly Pro Ile Pro Ser Val Ile Gly Leu Met
                245                 250                 255

Gln Ala Leu Ala Val Leu Asp Leu Ser Phe Asn Glu Leu Ser Gly Pro
            260                 265                 270

Ile Pro Ser Ile Leu Gly Asn Leu Thr Tyr Thr Glu Lys Leu Tyr Leu
```

-continued

```
                275                 280                 285
Gln Gly Asn Arg Leu Thr Gly Leu Ile Pro Pro Glu Leu Gly Asn Met
290                 295                 300
Ser Thr Leu His Tyr Leu Glu Leu Asn Asp Asn Leu Leu Thr Gly Phe
305                 310                 315                 320
Ile Pro Pro Asp Leu Gly Lys Leu Thr Glu Leu Phe Glu Leu Asn Leu
                325                 330                 335
Ala Asn Asn Asn Leu Ile Gly Pro Ile Pro Glu Asn Leu Ser Ser Cys
                340                 345                 350
Ala Asn Leu Ile Ser Phe Asn Ala Tyr Gly Asn Lys Leu Asn Gly Thr
                355                 360                 365
Ile Pro Arg Ser Phe His Lys Leu Glu Ser Leu Thr Tyr Leu Asn Leu
370                 375                 380
Ser Ser Asn His Leu Ser Gly Ala Leu Pro Ile Glu Val Ala Arg Met
385                 390                 395                 400
Arg Asn Leu Asp Thr Leu Asp Leu Ser Cys Asn Met Ile Thr Gly Ser
                405                 410                 415
Ile Pro Ser Ala Ile Gly Lys Leu Glu His Leu Leu Arg Leu Asn Leu
                420                 425                 430
Ser Lys Asn Asn Val Ala Gly His Ile Pro Ala Glu Phe Gly Asn Leu
                435                 440                 445
Arg Ser Ile Met Glu Ile Asp Leu Ser Tyr Asn His Leu Ser Gly Leu
                450                 455                 460
Ile Pro Gln Glu Val Gly Met Leu Gln Asn Leu Ile Leu Leu Lys Leu
465                 470                 475                 480
Glu Ser Asn Asn Ile Thr Gly Asp Val Ser Ser Leu Ile Tyr Cys Leu
                485                 490                 495
Ser Leu Asn Ile Leu Asn Val Ser Tyr Asn His Leu Tyr Gly Thr Val
                500                 505                 510
Pro Thr Asp Asn Asn Phe Ser Arg Phe Ser Pro Asp Ser Phe Leu Gly
                515                 520                 525
Asn Pro Gly Leu Cys Gly Tyr Trp Leu His Ser Ala Ser Cys Thr Gln
                530                 535                 540
Leu Ser Asn Ala Glu Gln Met Lys Arg Ser Ser Ser Ala Lys Ala Ser
545                 550                 555                 560
Met Phe Ala Ala Ile Gly Val Gly Ala Val Leu Leu Val Ile Met Leu
                565                 570                 575
Val Ile Leu Val Val Ile Cys Trp Pro His Asn Ser Pro Val Leu Lys
                580                 585                 590
Asp Val Ser Val Asn Lys Pro Asp Asn Leu Ala Ser Ala Ser Asn Asn
                595                 600                 605
Ile His Pro Lys Leu Val Ile Leu His Met Asn Met Ala Leu Tyr Val
                610                 615                 620
Tyr Asp Asp Ile Met Arg Met Thr Glu Asn Leu Ser Glu Lys Tyr Ile
625                 630                 635                 640
Ile Gly Tyr Gly Ala Ser Ser Thr Val Tyr Arg Cys Asp Leu Lys Asn
                645                 650                 655
Cys Lys Pro Ile Ala Ile Lys Lys Leu Tyr Ala His Tyr Pro Gln Ser
                660                 665                 670
Leu Lys Glu Phe Glu Thr Glu Leu Glu Thr Val Gly Ser Ile Lys His
                675                 680                 685
Arg Asn Leu Val Ser Leu Gln Gly Tyr Ser Leu Ser Pro Ser Gly Asn
                690                 695                 700
```

```
Leu Leu Phe Tyr Asp Tyr Met Glu Asn Gly Ser Leu Trp Asp Ile Leu
705                 710                 715                 720

His Ala Ser Ser Lys Lys Lys Leu Asp Trp Glu Ala Arg Leu Lys
            725                 730                 735

Ile Ala Leu Gly Ala Ala Gln Gly Leu Ala Tyr Leu His His Glu Cys
            740                 745                 750

Ser Pro Arg Ile Ile His Arg Asp Val Lys Ser Lys Asn Ile Leu Leu
        755                 760                 765

Asp Lys Asp Tyr Glu Ala His Leu Ala Asp Phe Gly Ile Ala Lys Ser
    770                 775                 780

Leu Cys Val Ser Lys Thr His Thr Ser Thr Tyr Val Met Gly Thr Ile
785                 790                 795                 800

Gly Tyr Ile Asp Pro Glu Tyr Ala Arg Thr Ser Arg Ile Asn Glu Lys
                805                 810                 815

Ser Asp Val Tyr Ser Tyr Gly Ile Val Leu Leu Glu Leu Leu Thr Gly
            820                 825                 830

Lys Lys Pro Val Asp Asp Glu Cys Asn Leu His His Leu Ile Leu Ser
        835                 840                 845

Lys Ala Ala Glu Asn Thr Val Met Glu Thr Val Asp Gln Asp Ile Thr
    850                 855                 860

Asp Thr Cys Lys Asp Leu Gly Glu Val Lys Lys Val Phe Gln Leu Ala
865                 870                 875                 880

Leu Leu Cys Ser Lys Arg Gln Pro Ser Asp Arg Pro Thr Met His Glu
                885                 890                 895

Val Ala Arg Val Leu Asp Ser Leu Val Cys Pro Ala Gly Pro Pro Pro
            900                 905                 910

Lys Gln Ala Gln Ala Gln Ala Gln Ala Ser Glu Lys Pro Ser
        915                 920                 925

Thr Thr Ala Pro Ser Tyr Val Ser Glu Tyr Val Gly Leu Arg Gly Gly
    930                 935                 940

Gly Gly Gly Ser Ala Leu Ser Cys Thr Asn Ser Ser Ser Ala Ser Asp
945                 950                 955                 960

Ala Glu Leu Phe Met Lys Phe Gly Glu Val Ile Ser Arg Ser Thr Glu
                965                 970                 975

<210> SEQ ID NO 9
<211> LENGTH: 2937
<212> TYPE: DNA
<213> ORGANISM: Oryza sativa

<400> SEQUENCE: 9
atgacgccgg cgccggcggc cgcctcctac cgcgctctcg tcgcgctcct gctcgtcgcc    60
gtcgccgttg ccgatgatgg gtcgacgctg ctggagatca agaagtcctt ccgcaatgtg    120
gacaacgtac tgtacgattg gccggcggc gactactgct cgtggcgcgg cgtcctctgc    180
gacaacgtca ccttcgccgt cgccgcgctc aacctatccg ggctcaacct cggaggcgag    240
atctctccgg ccgtcggcag gttgaagggc atcgtctcga ttgacttgaa gtcgaatggg    300
ctgtctgggc agatccctga tgagattggc gattgttcat cactaaaaac tctggatttg    360
tctttcaata gcttggatgg ggacattccg ttctcagtat cgaagctgaa gcacattgag    420
agcttgatat tgaagaacaa ccaactgatc ggagtgatcc catcaacgct ctcacagctc    480
ccaaatttga agattttgga cttggcacag aacaaactga gtggagagat accaagactg    540
atatattgga acgaggttct tcaatacttg ggattacgcg gtaataattt agaaggcagc    600
```

-continued

```
atctccccag atatatgcca gttgactggg ctttggtact ttgacgtaaa gaacaacagc      660
ttgactgggc cgataccaga aaccattggg aactgtacaa gttttcaggt cttggatttg      720
tcttacaata aactttctgg atcaattcct ttcaacattg gtttcctaca agttgctaca      780
ctatctttgc aagggaacat gtttactggt cctattccat cagttattgg acttatgcag      840
gctctcgctg tactggatct gagttacaac caattgtctg gtcctattcc atcgatacta      900
ggcaatttaa catacactga gaagctgtat atgcaaggca ataagttaac aggtccaata      960
ccacctgagc ttggaaatat gtcaaccctt cattacttag aacttaacga taatcaactt     1020
agcgggttca ttcctccaga gttcggaaag ctaacagggt tatttgactt aaaccttgca     1080
aacaacaact tgaaggtcc aatccctgat aacataagct catgtgtgaa tctcaatagc      1140
ttcaatgctt atggcaacag attaaatggg accattcctc cttcattgca taaacttgag     1200
agcatgactt atttgaattt gtcatcaaat tttctaagtg gttctattcc tattgagcta     1260
tcgagaatca acaatttgga caccttggat ttatcctgta acatgattac tggcccaatt     1320
ccatcaacca ttgggagttt ggagcatcta ttaagactta acttgagcaa caatggtcta     1380
gtaggattca ttcctgcaga aattggcaac ttgaggagta tcatggagat tgatatgtcc     1440
aacaatcatc ttggcggttt gattcctcaa gaactcggaa tgctgcaaaa tctgatgttg     1500
ttaaatctca aaaacaacaa cataactggg gatgtctctt cactgatgaa ctgcttcagc     1560
ctcaatatct aaatgtatc ctataataat ttggctggtg ttgtacctac tgataacaac      1620
ttctcacggt tttcgcctga cagcttttg ggtaatccag actttgtgg atattggctt       1680
ggttcttcgt gccgttcatc tggccatcaa cagaaaccac taatctcaaa ggctgcaata     1740
cttgaattg ccgtgggtgg gcttgttatc ctcctgatga tcttagtagc ggtctgcagg      1800
cctcatagtc cacctgtttt caaagatgtc tctgttagca aaccagtgag caatgttccc     1860
cccaagctgg ttatccttca tatgaacctt tccttcttg tatacgagga tataatgacg      1920
atgactgaaa acctgagtga gaagtacatc attgggtacg gagcatccag cacggtttat     1980
aaatgtgttt cgaagaaccg caaaccagtg gcagtaaaaa agctatatgc ccactatcca     2040
cagagcttca aggaatttga aactgagctt gagactgttg gtagcatcaa acaccggaat     2100
ctagtcagtc ttcaaggata ttccctatct cctgttggaa atcttctctt ctacgattac     2160
atggaaaatg gaagcctctg ggatgttttg catgaaggtc caactaagaa gaaaaaactt     2220
gattgggaaa ctcgtctacg aattgctcta ggtgcggccc aaggccttgc ttatcttcat     2280
catgactgta gcccacggat aatacacagg gatgtgaaat caaaaatat actccttgat      2340
aaagattatg aggcacatct tacagacttt ggcattgcta gagtttgtg tgtttcaaaa      2400
actcacacgt ccacctatgt catgggaact attggctata cgatcctga gtatgctcgc      2460
acctcccgtc tcaatgaaaa gtctgatgtc tacagctatg cattgttct gcttgagctg      2520
ctgaccggaa aaaagccagt ggacaacgag tgcaatctcc atcacttgat cttgtcaaag     2580
acggctaaca atgctgtcat ggagacagtc gacccggaca ttgcagacac ttgcaaggat     2640
cttggtgagg tcaagaaggt gttccagctg gcgctccttt gcaccaagag acaaccatcg     2700
gatcggccga caatgcacga ggttgtgcgc gtcctggact gcctagttcg tcccgacccg     2760
ccaccgaagt ccgcacagca gctggccatg ccgcagcggc ctgctgtccc gagctacatc     2820
aacgagtatg tcagcttaag aggcaccagc gtgctctcct gcgccaactc gtcgtgtact     2880
tccgatgctg agctgtttct caagtttggc gaggtcattt ctcagaacac agagtag       2937
```

<210> SEQ ID NO 10
<211> LENGTH: 978
<212> TYPE: PRT
<213> ORGANISM: Oryza sativa

<400> SEQUENCE: 10

```
Met Thr Pro Ala Pro Ala Ala Ser Tyr Arg Ala Leu Val Ala Leu
 1               5                  10                  15

Leu Leu Val Ala Val Ala Val Ala Asp Asp Gly Ser Thr Leu Leu Glu
                 20                  25                  30

Ile Lys Lys Ser Phe Arg Asn Val Asp Asn Val Leu Tyr Asp Trp Ala
             35                  40                  45

Gly Gly Asp Tyr Cys Ser Trp Arg Gly Val Leu Cys Asp Asn Val Thr
 50                  55                  60

Phe Ala Val Ala Ala Leu Asn Leu Ser Gly Leu Asn Leu Gly Gly Glu
 65                  70                  75                  80

Ile Ser Pro Ala Val Gly Arg Leu Lys Gly Ile Val Ser Ile Asp Leu
                 85                  90                  95

Lys Ser Asn Gly Leu Ser Gly Gln Ile Pro Asp Glu Ile Gly Asp Cys
            100                 105                 110

Ser Ser Leu Lys Thr Leu Asp Leu Ser Phe Asn Ser Leu Asp Gly Asp
        115                 120                 125

Ile Pro Phe Ser Val Ser Lys Leu Lys His Ile Glu Ser Leu Ile Leu
    130                 135                 140

Lys Asn Asn Gln Leu Ile Gly Val Ile Pro Ser Thr Leu Ser Gln Leu
145                 150                 155                 160

Pro Asn Leu Lys Ile Leu Asp Leu Ala Gln Asn Lys Leu Ser Gly Glu
                165                 170                 175

Ile Pro Arg Leu Ile Tyr Trp Asn Glu Val Leu Gln Tyr Leu Gly Leu
            180                 185                 190

Arg Gly Asn Asn Leu Glu Gly Ser Ile Ser Pro Asp Ile Cys Gln Leu
        195                 200                 205

Thr Gly Leu Trp Tyr Phe Asp Val Lys Asn Asn Ser Leu Thr Gly Pro
    210                 215                 220

Ile Pro Glu Thr Ile Gly Asn Cys Thr Ser Phe Gln Val Leu Asp Leu
225                 230                 235                 240

Ser Tyr Asn Lys Leu Ser Gly Ser Ile Pro Phe Asn Ile Gly Phe Leu
                245                 250                 255

Gln Val Ala Thr Leu Ser Leu Gln Gly Asn Met Phe Thr Gly Pro Ile
            260                 265                 270

Pro Ser Val Ile Gly Leu Met Gln Ala Leu Ala Val Leu Asp Leu Ser
        275                 280                 285

Tyr Asn Gln Leu Ser Gly Pro Ile Pro Ser Ile Leu Gly Asn Leu Thr
    290                 295                 300

Tyr Thr Glu Lys Leu Tyr Met Gln Gly Asn Lys Leu Thr Gly Pro Ile
305                 310                 315                 320

Pro Pro Glu Leu Gly Asn Met Ser Thr Leu His Tyr Leu Glu Leu Asn
                325                 330                 335

Asp Asn Gln Leu Ser Gly Phe Ile Pro Pro Glu Phe Gly Lys Leu Thr
            340                 345                 350

Gly Leu Phe Asp Leu Asn Leu Ala Asn Asn Phe Glu Gly Pro Ile
        355                 360                 365

Pro Asp Asn Ile Ser Ser Cys Val Asn Leu Asn Ser Phe Asn Ala Tyr
    370                 375                 380
```

-continued

```
Gly Asn Arg Leu Asn Gly Thr Ile Pro Pro Ser Leu His Lys Leu Glu
385                 390                 395                 400

Ser Met Thr Tyr Leu Asn Leu Ser Ser Asn Phe Leu Ser Gly Ser Ile
            405                 410                 415

Pro Ile Glu Leu Ser Arg Ile Asn Asn Leu Asp Thr Leu Asp Leu Ser
        420                 425                 430

Cys Asn Met Ile Thr Gly Pro Ile Pro Ser Thr Ile Gly Ser Leu Glu
    435                 440                 445

His Leu Leu Arg Leu Asn Leu Ser Asn Asn Gly Leu Val Gly Phe Ile
450                 455                 460

Pro Ala Glu Ile Gly Asn Leu Arg Ser Ile Met Glu Ile Asp Met Ser
465                 470                 475                 480

Asn Asn His Leu Gly Gly Leu Ile Pro Gln Glu Leu Gly Met Leu Gln
                485                 490                 495

Asn Leu Met Leu Asn Leu Lys Asn Asn Ile Thr Gly Asp Val
            500                 505                 510

Ser Ser Leu Met Asn Cys Phe Ser Leu Asn Ile Leu Asn Val Ser Tyr
        515                 520                 525

Asn Asn Leu Ala Gly Val Val Pro Thr Asp Asn Asn Phe Ser Arg Phe
    530                 535                 540

Ser Pro Asp Ser Phe Leu Gly Asn Pro Gly Leu Cys Gly Tyr Trp Leu
545                 550                 555                 560

Gly Ser Ser Cys Arg Ser Ser Gly His Gln Gln Lys Pro Leu Ile Ser
                565                 570                 575

Lys Ala Ala Ile Leu Gly Ile Ala Val Gly Gly Leu Val Ile Leu Leu
            580                 585                 590

Met Ile Leu Val Ala Val Cys Arg Pro His Ser Pro Val Phe Lys
        595                 600                 605

Asp Val Ser Val Ser Lys Pro Val Ser Asn Val Pro Pro Lys Leu Val
    610                 615                 620

Ile Leu His Met Asn Leu Ser Leu Leu Val Tyr Glu Asp Ile Met Thr
625                 630                 635                 640

Met Thr Glu Asn Leu Ser Glu Lys Tyr Ile Ile Gly Tyr Gly Ala Ser
                645                 650                 655

Ser Thr Val Tyr Lys Cys Val Ser Lys Asn Arg Lys Pro Val Ala Val
            660                 665                 670

Lys Lys Leu Tyr Ala His Tyr Pro Gln Ser Phe Lys Glu Phe Glu Thr
        675                 680                 685

Glu Leu Glu Thr Val Gly Ser Ile Lys His Arg Asn Leu Val Ser Leu
    690                 695                 700

Gln Gly Tyr Ser Leu Ser Pro Val Gly Asn Leu Leu Phe Tyr Asp Tyr
705                 710                 715                 720

Met Glu Asn Gly Ser Leu Trp Asp Val Leu His Glu Gly Pro Thr Lys
                725                 730                 735

Lys Lys Lys Leu Asp Trp Glu Thr Arg Leu Arg Ile Ala Leu Gly Ala
            740                 745                 750

Ala Gln Gly Leu Ala Tyr Leu His His Asp Cys Ser Pro Arg Ile Ile
        755                 760                 765

His Arg Asp Val Lys Ser Lys Asn Ile Leu Leu Asp Lys Asp Tyr Glu
    770                 775                 780

Ala His Leu Thr Asp Phe Gly Ile Ala Lys Ser Leu Cys Val Ser Lys
785                 790                 795                 800
```

-continued

```
Thr His Thr Ser Thr Tyr Val Met Gly Thr Ile Gly Tyr Ile Asp Pro
                805                 810                 815
Glu Tyr Ala Arg Thr Ser Arg Leu Asn Glu Lys Ser Asp Val Tyr Ser
            820                 825                 830
Tyr Gly Ile Val Leu Leu Glu Leu Leu Thr Gly Lys Lys Pro Val Asp
        835                 840                 845
Asn Glu Cys Asn Leu His His Leu Ile Leu Ser Lys Thr Ala Asn Asn
    850                 855                 860
Ala Val Met Glu Thr Val Asp Pro Asp Ile Ala Asp Thr Cys Lys Asp
865                 870                 875                 880
Leu Gly Glu Val Lys Lys Val Phe Gln Leu Ala Leu Leu Cys Thr Lys
                885                 890                 895
Arg Gln Pro Ser Asp Arg Pro Thr Met His Glu Val Val Arg Val Leu
            900                 905                 910
Asp Cys Leu Val Arg Pro Asp Pro Pro Lys Ser Ala Gln Gln Leu
        915                 920                 925
Ala Met Pro Gln Arg Pro Ala Val Pro Ser Tyr Ile Asn Glu Tyr Val
    930                 935                 940
Ser Leu Arg Gly Thr Ser Val Leu Ser Cys Ala Asn Ser Ser Cys Thr
945                 950                 955                 960
Ser Asp Ala Glu Leu Phe Leu Lys Phe Gly Glu Val Ile Ser Gln Asn
                965                 970                 975
Thr Glu

<210> SEQ ID NO 11
<211> LENGTH: 3000
<212> TYPE: DNA
<213> ORGANISM: Oryza sativa

<400> SEQUENCE: 11
```

| | | | | | |
|---|---|---|---|---|---|
| atggcggcgg | cgagggcgcc | gtggctgtgg | tggtgggtgg | tggtggttgt | tggtgtggcg | 60 |
| gtggcggagg | cggcctccgg | aggaggagga | ggggagatg | gggagggaa | ggcgctgatg | 120 |
| ggcgtgaagg | ccggtttcgg | gaacgcggcc | aacgcgctcg | tcgactggga | cggcggcgcc | 180 |
| gaccactgcg | cgtggcgcgg | cgtcacctgc | gacaacgcct | ccttcgccgt | cctcgccctg | 240 |
| aacttgtcaa | atctaaacct | aggaggtgag | atctcgccgg | ccatcggaga | gctcaagaat | 300 |
| ctacagttcg | ttgatctcaa | ggggaacaag | ctcactggcc | aaatcccaga | tgagattggg | 360 |
| gactgcatct | ccttaaaata | tttggatttg | tctggcaact | tgctgtatgg | agacatcccc | 420 |
| ttctccatct | ccaagctcaa | gcagcttgag | gagctgattt | tgaagaacaa | ccagctcacg | 480 |
| ggacccatcc | cttccacatt | gtcccaaatt | ccaaatctca | agacattgga | cctggcacag | 540 |
| aaccagctta | caggcgatat | cccaaggctc | atatactgga | atgaagttct | gcaataccta | 600 |
| ggtttgaggg | gtaactcact | gactggaact | tgtcacctg | acatgtgcca | actgactggc | 660 |
| ctgtggtact | tgatgtaag | gggaaacaat | ctcacaggga | ccattccaga | gagcataggg | 720 |
| aactgcacca | gctttgagat | tctggacatt | tcgtataacc | aaatctctgg | agaaatacct | 780 |
| tacaacatag | gctttcttca | gtagccaca | ctgtcacttc | aaggaaatag | actgactggg | 840 |
| aaaattccag | atgtgattgg | cctgatgcaa | gctcttgctg | ttctagacct | gagtgagaac | 900 |
| gagctggtag | ggcccattcc | ttctatactg | ggcaatctat | cctatactgg | aaaactatat | 960 |
| ttacatggga | acaaacttac | tggagtcata | ccgccggagc | ttgggaacat | gagtaaactt | 1020 |
| agctacctac | aactgaatga | taatgaattg | gtgggcacaa | ttccagcaga | gcttggcaaa | 1080 |

-continued

```
cttgaagagc tttttgaact aaatcttgcc aacaacaatc ttcaaggtcc tattcctgca      1140
aacatcagtt cttgcactgc tctaaacaaa ttcaatgttt atggcaataa gctaaatggt      1200
tctattcctg ctggtttcca gaagttggag agtctgactt acttgaacct atcttcaaac      1260
aatttcaaag gcaatattcc ttctgagctt ggtcacatca tcaacttgga cacattggat      1320
ctttcctaca tgaattctc tggaccagtt cctgctacca ttggtgatct agagcacctt      1380
cttgaactga atttgagtaa gaaccatctt gatgggccag ttcctgctga gtttggaaac      1440
ttgagaagcg tccaagtaat tgatatgtcc aacaacaact tatctggtag tctgcccgag      1500
gaacttggac aacttcaaaa ccttgatagc ctgattctta acaacaacaa tttggttggg      1560
gagatccctg ctcaattggc caactgcttc agcttaaata accttgcatt tcaggaattt      1620
gtcatacaac aatttatctg gacatgtccc gatggcaaag aacttctcga aattcccaat      1680
ggaaagcatc ttctaatttc tgattgcaac cagtacataa atcataaatg cagcttcttg      1740
ggtaatccat tactgcatgt ttactgccaa gattccagct gtggacactc tcatggacaa      1800
agagttaata tttcaaagac agcaattgct tgcattatct taggctttat catattgctc      1860
tgcgttctgc tgttggctat atataaaaca aatcaaccac agccacttgt caaaggatcc      1920
gataagccag tgcaaggacc tccaaagcta gttgttctcc agatggacat ggctatccat      1980
acttacgagg acatcatgag gctgacagag aatttgagcg agaaatacat cattggctat      2040
ggcgcctcaa gcactgtcta caaatgtgaa ctcaagagcg gcaaggccat tgctgtcaag      2100
cggctttaca gtcagtataa ccatagcctc gagagtttg aaacagaact agagacaatt      2160
ggcagcatac ggcacaggaa tcttgttagc ctccatggct tctcgctatc tccacatgga      2220
aacttgctct ctctatgatta catggaaaat ggttccttgt gggatcttct ccacggtcca      2280
tcaaagaaag tgaagctcaa ctgggacaca agactgagga tcgcggtcgg agctgcacaa      2340
gggctggcct atctccacca tgactgcaac cctcgcataa tccacagaga tgtcaagtcc      2400
tccaacatcc tgctcgacga gaacttcgaa gcgcacctct cagatttcgg catagccaaa      2460
tgtgtcccct ctgccaagtc ccatgcctcc acttatgtgc taggaaccat cggctacatt      2520
gatccggagt atgccaggac ttccaggctc aatgagaaat ctgatgtgta cagcttcggc      2580
atcgtccttc tggaattgct cacagggaag aaggccgtcg acaacgaatc gaacttgcat      2640
caattgatac tctccaaagc tgatgacaac acagtcatgg aggcagtgga ctcggaggtg      2700
tcagtgacgt gcacggacat gggactggtc aggaaggcct tccagctcgc ccttctgtgc      2760
accaagaggc acccttcaga ccggccgacc atgcacgagg ttgcaagggt gctgctctcc      2820
ctgctgccgg cctccgccat gacaacgccc aagacggtgg actactcccg gttgctggcg      2880
tcgacgacga cggcggccga catgcgaggg cacgacgtga ccgacatcgg cgacaacagc      2940
tcctccgacg agcagtggtt cgtcaggttc ggcgaggtca tatccaagca cacaatgtga      3000
```

<210> SEQ ID NO 12
<211> LENGTH: 999
<212> TYPE: PRT
<213> ORGANISM: Oryza sativa

<400> SEQUENCE: 12

```
Met Ala Ala Ala Arg Ala Pro Trp Leu Trp Trp Trp Val Val Val Val
 1               5                  10                  15

Val Gly Val Ala Val Ala Glu Ala Ala Ser Gly Gly Gly Gly Gly Gly
            20                  25                  30

Asp Gly Glu Gly Lys Ala Leu Met Gly Val Lys Ala Gly Phe Gly Asn
```

-continued

```
                35                  40                  45
Ala Ala Asn Ala Leu Val Asp Trp Asp Gly Ala Asp His Cys Ala
 50                  55                  60

Trp Arg Gly Val Thr Cys Asp Asn Ala Ser Phe Ala Val Leu Ala Leu
 65                  70                  75                  80

Asn Leu Ser Asn Leu Asn Leu Gly Gly Glu Ile Ser Pro Ala Ile Gly
                 85                  90                  95

Glu Leu Lys Asn Leu Gln Phe Val Asp Leu Lys Gly Asn Lys Leu Thr
                100                 105                 110

Gly Gln Ile Pro Asp Glu Ile Gly Asp Cys Ile Ser Leu Lys Tyr Leu
                115                 120                 125

Asp Leu Ser Gly Asn Leu Leu Tyr Gly Asp Ile Pro Phe Ser Ile Ser
                130                 135                 140

Lys Leu Lys Gln Leu Glu Glu Leu Ile Leu Lys Asn Asn Gln Leu Thr
145                 150                 155                 160

Gly Pro Ile Pro Ser Thr Leu Ser Gln Ile Pro Asn Leu Lys Thr Leu
                165                 170                 175

Asp Leu Ala Gln Asn Gln Leu Thr Gly Asp Ile Pro Arg Leu Ile Tyr
                180                 185                 190

Trp Asn Glu Val Leu Gln Tyr Leu Gly Leu Arg Gly Asn Ser Leu Thr
                195                 200                 205

Gly Thr Leu Ser Pro Asp Met Cys Gln Leu Thr Gly Leu Trp Tyr Phe
210                 215                 220

Asp Val Arg Gly Asn Asn Leu Thr Gly Thr Ile Pro Glu Ser Ile Gly
225                 230                 235                 240

Asn Cys Thr Ser Phe Glu Ile Leu Asp Ile Ser Tyr Asn Gln Ile Ser
                245                 250                 255

Gly Glu Ile Pro Tyr Asn Ile Gly Phe Leu Gln Val Ala Thr Leu Ser
                260                 265                 270

Leu Gln Gly Asn Arg Leu Thr Gly Lys Ile Pro Asp Val Ile Gly Leu
                275                 280                 285

Met Gln Ala Leu Ala Val Leu Asp Leu Ser Glu Asn Glu Leu Val Gly
290                 295                 300

Pro Ile Pro Ser Ile Leu Gly Asn Leu Ser Tyr Thr Gly Lys Leu Tyr
305                 310                 315                 320

Leu His Gly Asn Lys Leu Thr Gly Val Ile Pro Pro Glu Leu Gly Asn
                325                 330                 335

Met Ser Lys Leu Ser Tyr Leu Gln Leu Asn Asp Asn Glu Leu Val Gly
                340                 345                 350

Thr Ile Pro Ala Glu Leu Gly Lys Leu Glu Glu Leu Phe Glu Leu Asn
                355                 360                 365

Leu Ala Asn Asn Asn Leu Gln Gly Pro Ile Pro Ala Asn Ile Ser Ser
                370                 375                 380

Cys Thr Ala Leu Asn Lys Phe Asn Val Tyr Gly Asn Lys Leu Asn Gly
385                 390                 395                 400

Ser Ile Pro Ala Gly Phe Gln Lys Leu Glu Ser Leu Thr Tyr Leu Asn
                405                 410                 415

Leu Ser Ser Asn Asn Phe Lys Gly Asn Ile Pro Ser Glu Leu Gly His
                420                 425                 430

Ile Ile Asn Leu Asp Thr Leu Asp Leu Ser Tyr Asn Glu Phe Ser Gly
                435                 440                 445

Pro Val Pro Ala Thr Ile Gly Asp Leu Glu His Leu Leu Glu Leu Asn
450                 455                 460
```

```
Leu Ser Lys Asn His Leu Asp Gly Pro Val Pro Ala Glu Phe Gly Asn
465                 470                 475                 480

Leu Arg Ser Val Gln Val Ile Asp Met Ser Asn Asn Asn Leu Ser Gly
                485                 490                 495

Ser Leu Pro Glu Glu Leu Gly Gln Leu Gln Asn Leu Asp Ser Leu Ile
            500                 505                 510

Leu Asn Asn Asn Leu Val Gly Glu Ile Pro Ala Gln Leu Ala Asn
        515                 520                 525

Cys Phe Ser Leu Asn Asn Leu Ala Phe Gln Glu Phe Val Ile Gln Gln
530                 535                 540

Phe Ile Trp Thr Cys Pro Asp Gly Lys Glu Leu Leu Glu Ile Pro Asn
545                 550                 555                 560

Gly Lys His Leu Leu Ile Ser Asp Cys Asn Gln Tyr Ile Asn His Lys
                565                 570                 575

Cys Ser Phe Leu Gly Asn Pro Leu Leu His Val Tyr Cys Gln Asp Ser
            580                 585                 590

Ser Cys Gly His Ser His Gly Gln Arg Val Asn Ile Ser Lys Thr Ala
        595                 600                 605

Ile Ala Cys Ile Ile Leu Gly Phe Ile Ile Leu Leu Cys Val Leu Leu
610                 615                 620

Leu Ala Ile Tyr Lys Thr Asn Gln Pro Gln Pro Leu Val Lys Gly Ser
625                 630                 635                 640

Asp Lys Pro Val Gln Gly Pro Pro Lys Leu Val Val Leu Gln Met Asp
                645                 650                 655

Met Ala Ile His Thr Tyr Glu Asp Ile Met Arg Leu Thr Glu Asn Leu
            660                 665                 670

Ser Glu Lys Tyr Ile Ile Gly Tyr Gly Ala Ser Ser Thr Val Tyr Lys
        675                 680                 685

Cys Glu Leu Lys Ser Gly Lys Ala Ile Ala Val Lys Arg Leu Tyr Ser
690                 695                 700

Gln Tyr Asn His Ser Leu Arg Glu Phe Glu Thr Glu Leu Glu Thr Ile
705                 710                 715                 720

Gly Ser Ile Arg His Arg Asn Leu Val Ser Leu His Gly Phe Ser Leu
                725                 730                 735

Ser Pro His Gly Asn Leu Leu Phe Tyr Asp Tyr Met Glu Asn Gly Ser
            740                 745                 750

Leu Trp Asp Leu Leu His Gly Pro Ser Lys Val Lys Leu Asn Trp
        755                 760                 765

Asp Thr Arg Leu Arg Ile Ala Val Gly Ala Ala Gln Gly Leu Ala Tyr
770                 775                 780

Leu His His Asp Cys Asn Pro Arg Ile Ile His Arg Asp Val Lys Ser
785                 790                 795                 800

Ser Asn Ile Leu Leu Asp Glu Asn Phe Glu Ala His Leu Ser Asp Phe
                805                 810                 815

Gly Ile Ala Lys Cys Val Pro Ser Ala Lys Ser His Ala Ser Thr Tyr
            820                 825                 830

Val Leu Gly Thr Ile Gly Tyr Ile Asp Pro Glu Tyr Ala Arg Thr Ser
        835                 840                 845

Arg Leu Asn Glu Lys Ser Asp Val Tyr Ser Phe Gly Ile Val Leu Leu
850                 855                 860

Glu Leu Leu Thr Gly Lys Lys Ala Val Asp Asn Glu Ser Asn Leu His
865                 870                 875                 880
```

```
Gln Leu Ile Leu Ser Lys Ala Asp Asp Asn Thr Val Met Glu Ala Val
                885                 890                 895

Asp Ser Glu Val Ser Val Thr Cys Thr Asp Met Gly Leu Val Arg Lys
            900                 905                 910

Ala Phe Gln Leu Ala Leu Leu Cys Thr Lys Arg His Pro Ser Asp Arg
        915                 920                 925

Pro Thr Met His Glu Val Ala Arg Val Leu Leu Ser Leu Leu Pro Ala
    930                 935                 940

Ser Ala Met Thr Thr Pro Lys Thr Val Asp Tyr Ser Arg Leu Leu Ala
945                 950                 955                 960

Ser Thr Thr Thr Ala Ala Asp Met Arg Gly His Asp Val Thr Asp Ile
                965                 970                 975

Gly Asp Asn Ser Ser Ser Asp Glu Gln Trp Phe Val Arg Phe Gly Glu
            980                 985                 990

Val Ile Ser Lys His Thr Met
        995

<210> SEQ ID NO 13
<211> LENGTH: 3317
<212> TYPE: DNA
<213> ORGANISM: Sorghum bicolor

<400> SEQUENCE: 13
cctactggat cgcctatcgc ccagccatac agctactcgc tgtcactgag aaccagcggc      60
gcaagtgcgc aaagccgagc gcgagaaccc acgaaaccaa ccaagctctg cccccattaa     120
ggcagggcag gcagaggagg caggctcgct gcagcacgct tcgcgctcca tcgtcgctgt     180
cctcttctcc ctgtaatgtc actccccga tgcctgtccg cagctcagtg gccatgacga     240
cgacggccgc ccgtgctctc gtcgccctcc tcctcgtcgc cgtcgccgtc gccgacgatg     300
gggcgacgct ggtggagatc aagaagtcct tccgcaacgt cggcaacgta ctgtacgatt     360
gggccggcga cgactactgc tcctggcgcg gcgtcctgtg cgacaacgtc acattcgccg     420
tcgctgcgct caacctctct ggcctcaacc ttgagggcga gatctctcca gccgtcggca     480
gcctcaagag cctcgtctcc atcgatctga agtcaaatgg gctatccggg cagatccctg     540
atgagattgg tgattgttca tcacttagga cgctggactt ttctttcaac aacttggatg     600
gcgacatacc attctctata tcaaagctga agcacctgga gaacttgata ttgaagaaca     660
accagctgat tggtgcgatc ccatcaacat tgtcacagct cccaaatttg aagattttgg     720
atttggcaca aaacaaactg actggggaga taccaaggct tatctactgg aatgaggttc     780
ttcaatatct tgatgtgaag aacaatagct tgaccggggt gataccagac accattggga     840
actgtacaag ttttcaagtc ttggatttgt cttacaaccg ctttactgga ccaatcccat     900
tcaacattgg tttcctacaa gtggctacac tatccttgca agggaacaag ttcaccggtc     960
caattccttc agtaattggt cttatgcagg ctctcgctgt tctagatctg agttacaacc    1020
aattatctgg tcctatacca tcaatactag gcaacttgac atacactgag aagctgtaca    1080
tccaaggcaa taagttaact gggtcgatac caccagagtt aggaaatatg tcaacacttc    1140
attacctaga actgaacgat aatcaactta ctgggtcaat tccaccagag cttggaaggc    1200
taacaggctt gtttgacctg aaccttgcga ataaccacct ggaaggacca attcctgaca    1260
acctaagttc atgtgtgaat ctcaatagct tcaatgctta tggcaacaag ttaaatggga    1320
ccattcctcg ttcgttgcgg aaacttgaaa gcatgaccta tttaaatctg tcatcaaact    1380
tcataagtgg ctctattcct attgagttat caaggatcaa caatttggac acgctggatt    1440
```

```
tatcctgtaa catgatgact ggtccaattc catcatcaat tggcagccta gagcatctat   1500
tgagacttaa cttgagcaag aatggtctag ttggattcat ccccgcggag tttggtaatt   1560
tgaggagtgt catggagatt gatttatcct ataatcacct tggtggcctg attcctcaag   1620
aacttgaaat gctgcaaaac ctgatgttgc taaatgtgtc gtacaataat ttggctggtg   1680
ttgtccctgc tgacaacaac ttcacacggt tttcacctga cagcttttta ggtaatcctg   1740
gactctgtgg atactggctt ggttcgtcgt gtcgttccac tggccaccac gagaaaccgc   1800
ctatctcaaa ggctgccata attggtgttg ctgtgggtgg acttgttatc ctcttgatga   1860
tcttagtagc tgttttgcagg ccacatcgtc cacctgcttt taaagatgtc actgtaagca   1920
agccagtgag aaatgctccc cccaagctgg tgatccttca tatgaacatg gcccttcatg   1980
tatacgatga cataatgagg atgactgaga acttgagtga gaaatacatc attggatacg   2040
gggcgtcaag tacagtttat aaatgtgtcc taaagaattg caaaccggtg gcaataaaaa   2100
agctgtatgc ccactaccca cagagcctta aggaatttga aactgagctt gagactgttg   2160
gtagcatcaa gcaccggaat ctagtcagcc ttcaagggta ctcattatca cctgttggga   2220
acctcctctt ttatgattat atggaatgtg gcagcttatg ggatgtttta catgaaggtt   2280
catccaagaa gaaaaaactt gactgggaga ctcgcctacg gattgctctt ggtgcagctc   2340
aaggccttgc ttaccttcac catgactgca gtccacggat aattcatcgg gatgtaaaat   2400
caaagaatat actccttgac aaagattatg aggcccatct tacagacttt ggaattgcta   2460
agagcttatg tgtctcaaaa actcacacat caacctatgt catgggaact attggctaca   2520
ttgatcctga gtacgcccgc acttcccgtc tcaacgaaaa gtctgatgtc tacaggctat   2580
ggcattgttc tgctggagct gctgactggc aagaagccag tggacaacga atcctatcga   2640
agacggcaag caacgaggtc atggataccg tggaccctga catcggggac acctgcaagg   2700
acctcggcga ggtgaagaag ctgttccagc tggcgctcct ttgcaccaag cggcaacccc   2760
cggaccgacc gacgatgcac gaggtggtgc gcgtcctgga ctgcctggtg aacccggacc   2820
cgccgccaaa gccgtcggcg caccagctgc cgcagccgtc gccagccgtg ccaagctaca   2880
tcaacgagta cgtcagcctg cggggcaccg gcgctctctc ctgcgccaac tcgaccagca   2940
cctcggacgc cgagctgttc ctcaagttcg gcgaggccat ctcgcagaac atggagtagg   3000
gaagagagag aggtctgggg agttgaagga tgcagggagt agtgggagta gctgactgac   3060
attttgcggg atgcaggagg agattaacat ggggaactca gtagggtgtt ggttaactgt   3120
aaaaaaagtc atgtgcctct agagcagcag tagagcttct tcctcatctt tctttttttt   3180
atcacccccc atttttcctt ggtggtctct aacttgttag gaggctgtat tggtcatctc   3240
tcacagttgt gtgcctgatg atcttttgtg tgacttttgc cgtgttggaa tcatgggagg   3300
tgactttctt gatctgc                                                 3317
```

<210> SEQ ID NO 14
<211> LENGTH: 929
<212> TYPE: PRT
<213> ORGANISM: Sorghum bicolor

<400> SEQUENCE: 14

Met Pro Val Arg Ser Ser Val Ala Met Thr Thr Thr Ala Ala Arg Ala
 1               5                  10                  15

Leu Val Ala Leu Leu Leu Val Ala Val Ala Asp Asp Gly Ala
            20                  25                  30

-continued

```
Thr Leu Val Glu Ile Lys Lys Ser Phe Arg Asn Val Gly Asn Val Leu
         35                  40                  45

Tyr Asp Trp Ala Gly Asp Tyr Cys Ser Trp Arg Gly Val Leu Cys
     50                  55                  60

Asp Asn Val Thr Phe Ala Val Ala Leu Asn Leu Ser Gly Leu Asn
65                  70                  75                  80

Leu Glu Gly Glu Ile Ser Pro Ala Val Gly Ser Leu Lys Ser Leu Val
                 85                  90                  95

Ser Ile Asp Leu Lys Ser Asn Gly Leu Ser Gly Gln Ile Pro Asp Glu
                100                 105                 110

Ile Gly Asp Cys Ser Ser Leu Arg Thr Leu Asp Phe Ser Phe Asn Asn
                115                 120                 125

Leu Asp Gly Asp Ile Pro Phe Ser Ile Ser Lys Leu Lys His Leu Glu
130                 135                 140

Asn Leu Ile Leu Lys Asn Asn Gln Leu Ile Gly Ala Ile Pro Ser Thr
145                 150                 155                 160

Leu Ser Gln Leu Pro Asn Leu Lys Ile Leu Asp Leu Ala Gln Asn Lys
                165                 170                 175

Leu Thr Gly Glu Ile Pro Arg Leu Ile Tyr Trp Asn Glu Val Leu Gln
                180                 185                 190

Tyr Leu Asp Val Lys Asn Asn Ser Leu Thr Gly Val Ile Pro Asp Thr
                195                 200                 205

Ile Gly Asn Cys Thr Ser Phe Gln Val Leu Asp Leu Ser Tyr Asn Arg
                210                 215                 220

Phe Thr Gly Pro Ile Pro Phe Asn Ile Gly Phe Leu Gln Val Ala Thr
225                 230                 235                 240

Leu Ser Leu Gln Gly Asn Lys Phe Thr Gly Pro Ile Pro Ser Val Ile
                245                 250                 255

Gly Leu Met Gln Ala Leu Ala Val Leu Asp Leu Ser Tyr Asn Gln Leu
                260                 265                 270

Ser Gly Pro Ile Pro Ser Ile Leu Gly Asn Leu Thr Tyr Thr Glu Lys
                275                 280                 285

Leu Tyr Ile Gln Gly Asn Lys Leu Thr Gly Ser Ile Pro Pro Glu Leu
                290                 295                 300

Gly Asn Met Ser Thr Leu His Tyr Leu Glu Leu Asn Asp Asn Gln Leu
305                 310                 315                 320

Thr Gly Ser Ile Pro Pro Glu Leu Gly Arg Leu Thr Gly Leu Phe Asp
                325                 330                 335

Leu Asn Leu Ala Asn Asn His Leu Glu Gly Pro Ile Pro Asp Asn Leu
                340                 345                 350

Ser Ser Cys Val Asn Leu Asn Ser Phe Asn Ala Tyr Gly Asn Lys Leu
                355                 360                 365

Asn Gly Thr Ile Pro Arg Ser Leu Arg Lys Leu Glu Ser Met Thr Tyr
370                 375                 380

Leu Asn Leu Ser Ser Asn Phe Ile Ser Gly Ser Ile Pro Ile Glu Leu
385                 390                 395                 400

Ser Arg Ile Asn Asn Leu Asp Thr Leu Asp Leu Ser Cys Asn Met Met
                405                 410                 415

Thr Gly Pro Ile Pro Ser Ser Ile Gly Ser Leu Glu His Leu Leu Arg
                420                 425                 430

Leu Asn Leu Ser Lys Asn Gly Leu Val Gly Phe Ile Pro Ala Glu Phe
                435                 440                 445

Gly Asn Leu Arg Ser Val Met Glu Ile Asp Leu Ser Tyr Asn His Leu
```

```
                450                 455                 460
Gly Gly Leu Ile Pro Gln Glu Leu Glu Met Leu Gln Asn Leu Met Leu
465                 470                 475                 480

Leu Asn Val Ser Tyr Asn Asn Leu Ala Gly Val Val Pro Ala Asp Asn
                485                 490                 495

Asn Phe Thr Arg Phe Ser Pro Asp Ser Phe Leu Gly Asn Pro Gly Leu
                500                 505                 510

Cys Gly Tyr Trp Leu Gly Ser Ser Cys Arg Ser Thr Gly His His Glu
                515                 520                 525

Lys Pro Pro Ile Ser Lys Ala Ala Ile Ile Gly Val Ala Val Gly Gly
                530                 535                 540

Leu Val Ile Leu Leu Met Ile Leu Val Ala Val Cys Arg Pro His Arg
545                 550                 555                 560

Pro Pro Ala Phe Lys Asp Val Thr Val Ser Lys Pro Val Arg Asn Ala
                565                 570                 575

Pro Pro Lys Leu Val Ile Leu His Met Asn Met Ala Leu His Val Tyr
                580                 585                 590

Asp Asp Ile Met Arg Met Thr Glu Asn Leu Ser Glu Lys Tyr Ile Ile
                595                 600                 605

Gly Tyr Gly Ala Ser Ser Thr Val Tyr Lys Cys Val Leu Lys Asn Cys
                610                 615                 620

Lys Pro Val Ala Ile Lys Lys Leu Tyr Ala His Tyr Pro Gln Ser Leu
625                 630                 635                 640

Lys Glu Phe Glu Thr Glu Leu Glu Thr Val Gly Ser Ile Lys His Arg
                645                 650                 655

Asn Leu Val Ser Leu Gln Gly Tyr Ser Leu Ser Pro Val Gly Asn Leu
                660                 665                 670

Leu Phe Tyr Asp Tyr Met Glu Cys Gly Ser Leu Trp Asp Val Leu His
                675                 680                 685

Glu Gly Ser Ser Lys Lys Lys Leu Asp Trp Glu Thr Arg Leu Arg
                690                 695                 700

Ile Ala Leu Gly Ala Ala Gln Gly Leu Ala Tyr Leu His His Asp Cys
705                 710                 715                 720

Ser Pro Arg Ile Ile His Arg Asp Val Lys Ser Lys Asn Ile Leu Leu
                725                 730                 735

Asp Lys Asp Tyr Glu Ala His Leu Thr Asp Phe Gly Ile Ala Lys Ser
                740                 745                 750

Leu Cys Val Ser Lys Thr His Thr Ser Thr Tyr Val Met Gly Thr Ile
                755                 760                 765

Gly Tyr Ile Asp Pro Glu Tyr Ala Arg Thr Ser Arg Leu Asn Glu Lys
                770                 775                 780

Ser Asp Val Tyr Arg Leu Trp His Cys Ser Ala Gly Ala Ala Asp Trp
785                 790                 795                 800

Gln Glu Ala Ser Gly Gln Arg Ile Leu Ser Lys Thr Ala Ser Asn Glu
                805                 810                 815

Val Met Asp Thr Val Asp Pro Asp Ile Gly Asp Thr Cys Lys Asp Leu
                820                 825                 830

Gly Glu Val Lys Lys Leu Phe Gln Leu Ala Leu Leu Cys Thr Lys Arg
                835                 840                 845

Gln Pro Ser Asp Arg Pro Thr Met His Glu Val Val Arg Val Leu Asp
                850                 855                 860

Cys Leu Val Asn Pro Asp Pro Pro Lys Pro Ser Ala His Gln Leu
865                 870                 875                 880
```

```
Pro Gln Pro Ser Pro Ala Val Pro Ser Tyr Ile Asn Glu Tyr Val Ser
                885                 890                 895

Leu Arg Gly Thr Gly Ala Leu Ser Cys Ala Asn Ser Thr Ser Thr Ser
            900                 905                 910

Asp Ala Glu Leu Phe Leu Lys Phe Gly Glu Ala Ile Ser Gln Asn Met
        915                 920                 925

Glu

<210> SEQ ID NO 15
<211> LENGTH: 1514
<212> TYPE: DNA
<213> ORGANISM: Sorghum bicolor

<400> SEQUENCE: 15
atggcagcga gggcggcggc ggcggtggtg ctgcttattg cggctgtggt gtcggtgtcg     60 gcggaggag gtgaagggga cggagacggg cagacgctga tggcggtcaa ggcggggttc    120
gggaacgcgg ccaacgcgct ggcggactgg gacggcggcc gcgaccactg cgcctggcgc    180
ggcgtcgcct cgacgccgc ctctttcgcc gtcgtcggcc tgaacctgtc aaatctaaac    240
ctcggagggg agatctcgcc ggctataggg cagctcaaga gcctacagtt cgtggatctc    300
aagctgaaca gctcacaagg ccaaatccca atgagattg ggattgtgt ctccttaaaa    360 tatttggatt tgtctggaaa cttgctgtat ggagacatcc ccttctccat ctccaagctc    420
aaacagcttg aggacctgat tttgaagaac aaccaactca cgggacccat cccttccaca    480
ctgtcccaga ttccaaatct caagaccttg gatctggcgc agaacaagct caccggagac    540
attcccaggc tcatctactg gaatgaagta ctgcaatacc taggcttgag gggcaattca    600
ctgactggaa ctctgtcacc tgatatgtgc caactgactg gcctgtggta ttttgatgta    660 aggggggaaca atctcacagg aacaattcca gagggcatag gaactgcac tagctttgag    720 attctggata tttcatacaa ccaaatctct ggagaaatac cttacaacat aggttacctt    780
caagtagcca cacttgatct tagcgagaat gaacttgtgg accaattcc tccgatactt    840 ggcaacctgt cctacacagg caaactctat ttacatggca caaactcac gggacatata    900 ccaccagaac tggggaacat gagtaaactt agctacctgc agctgaatga caatgaacta    960
gtgggcacaa tcccagctga gcttggcaaa ctcacagagt tatttgaatt gaatcttgcc   1020
aacaacaatc ttgagggtca tattcctgca aacatcagct cttgcagtgc actgaacaaa   1080
ttcaatgtgt atggcaatag actgaatggc tctatccctg ctggtttcca ggagttggag   1140
agtttgacat acctgaacct ttcttcaaac aatttcaaag ccagattcc ctctgagctt   1200 ggtcacatag tcaacttgga cacactagat cttttcctaca atgaattctc tggaccagtt   1260
cctcctacta ttggtgatct cgagcatctt cttgaattga atttgagtaa aaaccatctt   1320
actggatctg tgcctgctga atttggaaac ttgagaagtg tccaagtaat tgacatatcc   1380
agcaacaact tgactggtta tctccctgaa gaacttggac agctgcaaaa ccttgatagc   1440
ttgattctta acaacaacaa tttggttggg gagatccctg ctcagctggc taactgcttc   1500
agcttaatta cctt                                                     1514

<210> SEQ ID NO 16
<211> LENGTH: 504
<212> TYPE: PRT
<213> ORGANISM: Sorghum bicolor

<400> SEQUENCE: 16
```

```
Met Ala Ala Arg Ala Ala Ala Val Val Leu Leu Ile Ala Ala Val
  1               5                  10                  15

Val Ser Val Ser Ala Gly Gly Glu Gly Asp Gly Asp Gly Gln Thr
             20                  25                  30

Leu Met Ala Val Lys Ala Gly Phe Gly Asn Ala Ala Asn Ala Leu Ala
         35                  40                  45

Asp Trp Asp Gly Gly Arg Asp His Cys Ala Trp Arg Gly Val Ala Cys
     50                  55                  60

Asp Ala Ala Ser Phe Ala Val Val Gly Leu Asn Leu Ser Asn Leu Asn
 65              70                  75                  80

Leu Gly Gly Glu Ile Ser Pro Ala Ile Gly Gln Leu Lys Ser Leu Gln
                 85                  90                  95

Phe Val Asp Leu Lys Leu Asn Lys Leu Thr Gly Gln Ile Pro Asp Glu
             100                 105                 110

Ile Gly Asp Cys Val Ser Leu Lys Tyr Leu Asp Leu Ser Gly Asn Leu
             115                 120                 125

Leu Tyr Gly Asp Ile Pro Phe Ser Ile Ser Lys Leu Lys Gln Leu Glu
         130                 135                 140

Asp Leu Ile Leu Lys Asn Asn Gln Leu Thr Gly Pro Ile Pro Ser Thr
145                 150                 155                 160

Leu Ser Gln Ile Pro Asn Leu Lys Thr Leu Asp Leu Ala Gln Asn Lys
                 165                 170                 175

Leu Thr Gly Asp Ile Pro Arg Leu Ile Tyr Trp Asn Glu Val Leu Gln
             180                 185                 190

Tyr Leu Gly Leu Arg Gly Asn Ser Leu Thr Gly Thr Leu Ser Pro Asp
         195                 200                 205

Met Cys Gln Leu Thr Gly Leu Trp Tyr Phe Asp Val Arg Gly Asn Asn
     210                 215                 220

Leu Thr Gly Thr Ile Pro Glu Gly Ile Gly Asn Cys Thr Ser Phe Glu
225                 230                 235                 240

Ile Leu Asp Ile Ser Tyr Asn Gln Ile Ser Gly Glu Ile Pro Tyr Asn
                 245                 250                 255

Ile Gly Tyr Leu Gln Val Ala Thr Leu Asp Leu Ser Glu Asn Glu Leu
             260                 265                 270

Val Gly Pro Ile Pro Pro Ile Leu Gly Asn Leu Ser Tyr Thr Gly Lys
         275                 280                 285

Leu Tyr Leu His Gly Asn Lys Leu Thr Gly His Ile Pro Pro Glu Leu
     290                 295                 300

Gly Asn Met Ser Lys Leu Ser Tyr Leu Gln Leu Asn Asp Asn Glu Leu
305                 310                 315                 320

Val Gly Thr Ile Pro Ala Glu Leu Gly Lys Leu Thr Glu Leu Phe Glu
                 325                 330                 335

Leu Asn Leu Ala Asn Asn Leu Glu Gly His Ile Pro Ala Asn Ile
             340                 345                 350

Ser Ser Cys Ser Ala Leu Asn Lys Phe Asn Val Tyr Gly Asn Arg Leu
     355                 360                 365

Asn Gly Ser Ile Pro Ala Gly Phe Gln Glu Leu Glu Ser Leu Thr Tyr
     370                 375                 380

Leu Asn Leu Ser Ser Asn Asn Phe Lys Gly Gln Ile Pro Ser Glu Leu
385                 390                 395                 400

Gly His Ile Val Asn Leu Asp Thr Leu Asp Leu Ser Tyr Asn Glu Phe
                 405                 410                 415
```

```
Ser Gly Pro Val Pro Pro Thr Ile Gly Asp Leu Glu His Leu Leu Glu
            420                 425                 430

Leu Asn Leu Ser Lys Asn His Leu Thr Gly Ser Val Pro Ala Glu Phe
        435                 440                 445

Gly Asn Leu Arg Ser Val Gln Val Ile Asp Ile Ser Ser Asn Asn Leu
    450                 455                 460

Thr Gly Tyr Leu Pro Glu Glu Leu Gly Gln Leu Gln Asn Leu Asp Ser
465                 470                 475                 480

Leu Ile Leu Asn Asn Asn Leu Val Gly Glu Ile Pro Ala Gln Leu
                485                 490                 495

Ala Asn Cys Phe Ser Leu Ile Thr
            500

<210> SEQ ID NO 17
<211> LENGTH: 752
<212> TYPE: PRT
<213> ORGANISM: Sorghum bicolor

<400> SEQUENCE: 17

Cys Thr Thr Cys Ala Ala Ala Thr Gly Gly Ala Cys Ala Thr Gly Gly
 1               5                  10                  15

Cys Thr Ala Cys Cys Ala Thr Ala Cys Cys Thr Ala Thr Gly Gly Ala
            20                  25                  30

Ala Gly Ala Cys Ala Thr Thr Ala Thr Gly Ala Gly Gly Thr Thr Gly
        35                  40                  45

Ala Cys Thr Gly Ala Gly Ala Ala Thr Thr Gly Ala Gly Gly Cys Gly
    50                  55                  60

Ala Gly Ala Ala Ala Thr Ala Cys Ala Thr Cys Ala Thr Thr Gly Gly
65                  70                  75                  80

Thr Thr Ala Thr Gly Gly Gly Cys Ala Thr Cys Ala Ala Gly Thr
                85                  90                  95

Ala Cys Thr Gly Thr Gly Thr Ala Cys Ala Ala Ala Thr Gly Thr Gly
            100                 105                 110

Ala Thr Cys Thr Cys Ala Ala Gly Gly Gly Cys Gly Gly Cys Ala Ala
            115                 120                 125

Ala Gly Cys Cys Ala Thr Cys Gly Cys Thr Gly Thr Cys Ala Ala Ala
        130                 135                 140

Cys Gly Gly Cys Thr Thr Thr Ala Cys Ala Gly Thr Cys Ala Gly Thr
145                 150                 155                 160

Ala Thr Ala Ala Cys Cys Ala Cys Ala Gly Cys Cys Thr Cys Cys Gly
                165                 170                 175

Thr Gly Ala Gly Thr Thr Thr Gly Ala Gly Ala Cys Ala Gly Ala Ala
            180                 185                 190

Cys Thr Gly Gly Ala Gly Ala Cys Gly Ala Thr Cys Gly Gly Thr Ala
        195                 200                 205

Gly Cys Ala Thr Cys Cys Gly Ala Cys Ala Cys Ala Gly Gly Ala Ala
    210                 215                 220

Thr Cys Thr Cys Gly Thr Cys Ala Gly Cys Cys Thr Cys Ala Thr
225                 230                 235                 240

Gly Gly Cys Thr Cys Thr Cys Ala Cys Thr Cys Cys Cys
                245                 250                 255

Cys Thr Cys Ala Thr Gly Gly Ala Ala Ala Cys Cys Thr Gly Cys Thr
            260                 265                 270

Thr Thr Thr Cys Thr Ala Cys Gly Ala Thr Thr Ala Cys Ala Thr Gly
            275                 280                 285
```

-continued

```
Gly Ala Ala Ala Ala Thr Gly Gly Thr Thr Cys Cys Cys Thr Gly Thr
    290                 295                 300
Gly Gly Gly Ala Thr Cys Thr Thr Cys Thr Thr Cys Ala Thr Gly Gly
305                 310                 315                 320

Thr Cys Cys Ala Thr Cys Ala Ala Ala Gly Ala Ala Gly Gly Thr Gly
                325                 330                 335

Ala Ala Gly Cys Thr Thr Gly Ala Thr Thr Gly Gly Gly Ala Cys Ala
            340                 345                 350

Cys Ala Ala Gly Gly Cys Thr Thr Ala Ala Gly Ala Thr Thr Gly Cys
        355                 360                 365

Gly Gly Thr Ala Gly Gly Thr Gly Cys Thr Gly Cys Gly Cys Ala Ala
    370                 375                 380

Gly Gly Ala Cys Thr Gly Gly Cys Cys Thr Ala Thr Cys Thr Thr Cys
385                 390                 395                 400
Ala Cys Cys Ala Thr Gly Ala Cys Thr Gly Cys Ala Ala Cys Cys Cys
                405                 410                 415
Thr Cys Gly Cys Ala Thr Ala Ala Thr Cys Cys Ala Cys Ala Gly Gly
            420                 425                 430
Gly Ala Thr Gly Thr Cys Ala Ala Gly Thr Cys Cys Thr Cys Ala Ala
        435                 440                 445
Ala Cys Ala Thr Cys Cys Thr Gly Cys Thr Cys Gly Ala Cys Gly Ala
    450                 455                 460

Gly Ala Ala Cys Thr Thr Cys Gly Ala Ala Gly Cys Gly Cys Ala Cys
465                 470                 475                 480

Cys Thr Cys Thr Cys Thr Gly Ala Thr Thr Thr Cys Gly Gly Cys Ala
                485                 490                 495

Thr Cys Gly Cys Cys Ala Ala Ala Thr Gly Thr Gly Thr Cys Cys Cys
            500                 505                 510

Gly Gly Cys Thr Gly Cys Cys Ala Ala Gly Thr Cys Cys Cys Ala Thr
        515                 520                 525

Gly Cys Cys Thr Cys Cys Ala Cys Cys Thr Ala Cys Gly Thr Gly Cys
    530                 535                 540

Thr Thr Gly Gly Ala Ala Cys Cys Ala Thr Thr Gly Gly Cys Thr Ala
545                 550                 555                 560

Cys Ala Thr Thr Gly Ala Thr Cys Cys Ala Gly Ala Gly Thr Ala Thr
                565                 570                 575

Gly Cys Cys Cys Gly Cys Ala Cys Gly Thr Cys Gly Ala Gly Gly Cys
            580                 585                 590

Thr Cys Ala Ala Thr Gly Ala Gly Ala Ala Ala Thr Cys Gly Gly Ala
        595                 600                 605

Thr Gly Thr Cys Thr Ala Cys Ala Gly Cys Thr Thr Thr Gly Gly Cys
    610                 615                 620

Ala Thr Cys Gly Thr Cys Cys Thr Thr Cys Thr Gly Gly Ala Gly Cys
625                 630                 635                 640

Thr Gly Cys Thr Cys Ala Cys Cys Gly Gly Gly Ala Ala Gly Ala Ala
                645                 650                 655

Gly Gly Cys Thr Gly Thr Ala Gly Ala Cys Ala Ala Thr Gly Ala Ala
            660                 665                 670

Thr Cys Cys Ala Ala Cys Thr Thr Gly Cys Ala Cys Cys Ala Ala Thr
        675                 680                 685

Thr Gly Ala Thr Ala Cys Thr Cys Thr Cys Ala Ala Ala Ala Gly Cys
    690                 695                 700
```

```
Thr Gly Ala Cys Gly Ala Cys Ala Cys Ala Cys Gly Gly Thr Gly
705                 710                 715                 720

Ala Thr Gly Gly Ala Gly Gly Cys Thr Gly Thr Gly Ala Cys Thr
            725                 730                 735

Cys Gly Gly Ala Gly Gly Thr Thr Cys Ala Gly Thr Gly Ala Cys
            740                 745                 750

<210> SEQ ID NO 18
<211> LENGTH: 250
<212> TYPE: PRT
<213> ORGANISM: Sorghum bicolor

<400> SEQUENCE: 18

Leu Gln Met Asp Met Ala Thr His Thr Tyr Glu Asp Ile Met Arg Leu
1               5                   10                  15

Thr Glu Asn Leu Ser Glu Lys Tyr Ile Ile Gly Tyr Gly Ala Ser Ser
            20                  25                  30

Thr Val Tyr Lys Cys Asp Leu Lys Gly Lys Ala Ile Ala Val Lys
        35                  40                  45

Arg Leu Tyr Ser Gln Tyr Asn His Ser Leu Arg Glu Phe Glu Thr Glu
50                  55                  60

Leu Glu Thr Ile Gly Ser Ile Arg His Arg Asn Leu Val Ser Leu His
65                  70                  75                  80

Gly Phe Ser Leu Ser Pro His Gly Asn Leu Phe Tyr Asp Tyr Met
                85                  90                  95

Glu Asn Gly Ser Leu Trp Asp Leu Leu His Gly Pro Ser Lys Lys Val
            100                 105                 110

Lys Leu Asp Trp Asp Thr Arg Leu Lys Ile Ala Val Gly Ala Ala Gln
        115                 120                 125

Gly Leu Ala Tyr Leu His His Asp Cys Asn Pro Arg Ile Ile His Arg
130                 135                 140

Asp Val Lys Ser Ser Asn Ile Leu Leu Asp Glu Asn Phe Glu Ala His
145                 150                 155                 160

Leu Ser Asp Phe Gly Ile Ala Lys Cys Val Pro Ala Ala Lys Ser His
                165                 170                 175

Ala Ser Thr Tyr Val Leu Gly Thr Ile Gly Tyr Ile Asp Pro Glu Tyr
            180                 185                 190

Ala Arg Thr Ser Arg Leu Asn Glu Lys Ser Asp Val Tyr Ser Phe Gly
        195                 200                 205

Ile Val Leu Leu Glu Leu Leu Thr Gly Lys Lys Ala Val Asp Asn Glu
210                 215                 220

Ser Asn Leu His Gln Leu Ile Leu Ser Lys Ala Asp Asp Asn Thr Val
225                 230                 235                 240

Met Glu Ala Val Asp Ser Glu Val Ser Val
                245                 250

<210> SEQ ID NO 19
<211> LENGTH: 1402
<212> TYPE: DNA
<213> ORGANISM: Glycine max
<220> FEATURE:
<221> NAME/KEY: misc_feature
<222> LOCATION: 1253
<223> OTHER INFORMATION: n = A,T,C or G
<221> NAME/KEY: misc_feature
<222> LOCATION: 1253
<223> OTHER INFORMATION: n = A,T,C or G

<400> SEQUENCE: 19
```

-continued

```
cttagtctct ctctacttaa tgtgtcctat aacaaactat ttggtgttat ccccacgagt    60
aacaacttta ccaggtttcc ccctgacagt ttcattggaa accctggtct tgtgtggtaat  120 tggctgaatt tgccatgcca tggtgctcgt ccttcagagc gagttacatt atctaaggct   180
gccattcttg gaattacttt gggtgccctt gtgattcttc ttatggtatt ggtggcagct   240
tgccgaccac acagccccct ccttttcctt gatggatcat ttgacaaacc aattaatttc   300 tccctccaa agctagtgat tcttcatatg aatatggcac tacatgtgta tgaagatatc    360
atgaggatga ctgaaaacct aagtgagaag tatatcattg gatatggtgc atcaagtaca   420
gtttataaat gtgttcttaa gaattgtaag ccggtggcta tcaagaggat ctattctcac   480
tatccccaat gtattaaaga atttgaaact gaactcgaga ctgttggcag catcaagcac   540
cggaatttgg tcagtctcca aggctactcc ttgtccccat atggccatct cctgttttat   600
gactacatgg aaaatggcag tctatgggat cttcttcatg gacctaccaa gaagaaaaag   660
cttgactggg agctgcgtct aaaaatagca cttggagcag cacaagggct tgcttatcta   720
caccatgatt gctgtcctag aatcatccac agagatgtga aatcatctaa cattctattg   780
gatgcagact ttgagcctca tctcactgat tttggcattg ccaaaagtct ctgcccctca   840
aagtcccata cttctactta cataatgggc acaattggct atatagaccc tgagtatgct   900
agaacttcac gtctcactga agtctgatg tgtacagtt acggtattgt tttacttgag     960
ttgctaactg gaaggaaagc tgttgacaat gaatccaacc tccaccatct gattttgtcc  1020
aaggcagcaa ccaatgcagt gatggaaaca gttgatccag acattactgc cacatgcaag  1080
gacctaggag ctgtaaaaaa ggtttatcag cttgctctat tatgcacaaa gaggcagcca  1140
gctgataggc cgacaatgca cgaagtgaca cgtgtactcg gaagccttgt gctgtccaac  1200
accccaccaa agcaactagc tgcactacca cctgcttcag atccatctgc canagtgcca  1260
tgctacgtgg atgagtatgg caaacctcaa gactccacac ttggtgaaac tgcccctcaa  1320
tgagccacct aaatgctcaa ctctttctca gtttggagaa gtaatctct tcaaacaatg   1380 aggtgaaaga gtgaagccgg ga                                            1402
```

<210> SEQ ID NO 20
<211> LENGTH: 440
<212> TYPE: PRT
<213> ORGANISM: Glycine max
<220> FEATURE:
<221> NAME/KEY: VARIANT
<222> LOCATION: 418
<223> OTHER INFORMATION: Xaa = Any Amino Acid
<221> NAME/KEY: VARIANT
<222> LOCATION: 418
<223> OTHER INFORMATION: Xaa = Any Amino Acid

<400> SEQUENCE: 20

```
Leu Ser Leu Ser Leu Leu Asn Val Ser Tyr Asn Lys Leu Phe Gly Val
 1               5                  10                  15

Ile Pro Thr Ser Asn Asn Phe Thr Arg Phe Pro Pro Asp Ser Phe Ile
            20                  25                  30

Gly Asn Pro Gly Leu Cys Gly Asn Trp Leu Asn Leu Pro Cys His Gly
        35                  40                  45

Ala Arg Pro Ser Glu Arg Val Thr Leu Ser Lys Ala Ala Ile Leu Gly
    50                  55                  60

Ile Thr Leu Gly Ala Leu Val Ile Leu Leu Met Val Leu Val Ala Ala
65                  70                  75                  80
```

Cys Arg Pro His Ser Pro Ser Pro Phe Pro Asp Gly Ser Phe Asp Lys
                85                  90                  95

Pro Ile Asn Phe Ser Pro Pro Lys Leu Val Ile Leu His Met Asn Met
            100                 105                 110

Ala Leu His Val Tyr Glu Asp Ile Met Arg Met Thr Glu Asn Leu Ser
        115                 120                 125

Glu Lys Tyr Ile Ile Gly Tyr Gly Ala Ser Ser Thr Val Tyr Lys Cys
    130                 135                 140

Val Leu Lys Asn Cys Lys Pro Val Ala Ile Lys Arg Ile Tyr Ser His
145                 150                 155                 160

Tyr Pro Gln Cys Ile Lys Glu Phe Glu Thr Glu Leu Glu Thr Val Gly
                165                 170                 175

Ser Ile Lys His Arg Asn Leu Val Ser Leu Gln Gly Tyr Ser Leu Ser
            180                 185                 190

Pro Tyr Gly His Leu Leu Phe Tyr Asp Tyr Met Glu Asn Gly Ser Leu
        195                 200                 205

Trp Asp Leu Leu His Gly Pro Thr Lys Lys Lys Leu Asp Trp Glu
    210                 215                 220

Leu Arg Leu Lys Ile Ala Leu Gly Ala Ala Gln Gly Leu Ala Tyr Leu
225                 230                 235                 240

His His Asp Cys Cys Pro Arg Ile Ile His Arg Asp Val Lys Ser Ser
                245                 250                 255

Asn Ile Leu Leu Asp Ala Asp Phe Glu Pro His Leu Thr Asp Phe Gly
            260                 265                 270

Ile Ala Lys Ser Leu Cys Pro Ser Lys Ser His Thr Ser Thr Tyr Ile
        275                 280                 285

Met Gly Thr Ile Gly Tyr Ile Asp Pro Glu Tyr Ala Arg Thr Ser Arg
    290                 295                 300

Leu Thr Glu Lys Ser Asp Val Tyr Ser Tyr Gly Ile Val Leu Leu Glu
305                 310                 315                 320

Leu Leu Thr Gly Arg Lys Ala Val Asp Asn Glu Ser Asn Leu His His
                325                 330                 335

Leu Ile Leu Ser Lys Ala Ala Thr Asn Ala Val Met Glu Thr Val Asp
            340                 345                 350

Pro Asp Ile Thr Ala Thr Cys Lys Asp Leu Gly Ala Val Lys Lys Val
        355                 360                 365

Tyr Gln Leu Ala Leu Leu Cys Thr Lys Arg Gln Pro Ala Asp Arg Pro
    370                 375                 380

Thr Met His Glu Val Thr Arg Val Leu Gly Ser Leu Val Leu Ser Asn
385                 390                 395                 400

Thr Pro Pro Lys Gln Leu Ala Ala Leu Pro Pro Ala Ser Asp Pro Ser
                405                 410                 415

Ala Xaa Val Pro Cys Tyr Val Asp Glu Tyr Gly Lys Pro Gln Asp Ser
            420                 425                 430

Thr Leu Gly Glu Thr Ala Pro Gln
        435                 440

<210> SEQ ID NO 21
<211> LENGTH: 492
<212> TYPE: DNA
<213> ORGANISM: Glycine max

<400> SEQUENCE: 21
gagtatgcta gaacttcgca tctcactgag aagtctgatg tgtacagtta tggtattgtt    60

-continued

```
ttactcgagt tgctaactgg aaggaaagct gttgacaatg aatccaacct ccaccatctt    120
attttgtcca aggcagcaac caatgctgtg atggaaacag ttgatcccga cattactgcc    180
acatgcaagg acctaggagc tgtaaaaaag gtttatcagc ttgctctatt atgcacaaag    240
aggcagccag ctgataggcc aacaatgcac gaagtgacac gtgtactcgg aagtctcgtg    300
ccatcaagca tcccaccaaa gcaactagct gacctaccac ctgcttcaaa tccatctgcc    360
aaagtgccat gctacgtgga tgagtatgca aacctcaaaa ccccacactt agtaaactgc    420
ccctcaatga gcacttcaga tgctcaactc ttcctcaagt ttggagaagt aatctctcaa    480
aacagtgagt ga                                                        492
```

<210> SEQ ID NO 22
<211> LENGTH: 163
<212> TYPE: PRT
<213> ORGANISM: Glycine max

<400> SEQUENCE: 22

```
Glu Tyr Ala Arg Thr Ser His Leu Thr Glu Lys Ser Asp Val Tyr Ser
 1               5                  10                  15

Tyr Gly Ile Val Leu Leu Glu Leu Leu Thr Gly Arg Lys Ala Val Asp
            20                  25                  30

Asn Glu Ser Asn Leu His His Leu Ile Leu Ser Lys Ala Ala Thr Asn
        35                  40                  45

Ala Val Met Glu Thr Val Asp Pro Asp Ile Thr Ala Thr Cys Lys Asp
    50                  55                  60

Leu Gly Ala Val Lys Lys Val Tyr Gln Leu Ala Leu Leu Cys Thr Lys
65                  70                  75                  80

Arg Gln Pro Ala Asp Arg Pro Thr Met His Glu Val Thr Arg Val Leu
                85                  90                  95

Gly Ser Leu Val Pro Ser Ser Ile Pro Pro Lys Gln Leu Ala Asp Leu
            100                 105                 110

Pro Pro Ala Ser Asn Pro Ser Ala Lys Val Pro Cys Tyr Val Asp Glu
        115                 120                 125

Tyr Ala Asn Leu Lys Thr Pro His Leu Val Asn Cys Pro Ser Met Ser
    130                 135                 140

Thr Ser Asp Ala Gln Leu Phe Leu Lys Phe Gly Glu Val Ile Ser Gln
145                 150                 155                 160

Asn Ser Glu
```

<210> SEQ ID NO 23
<211> LENGTH: 797
<212> TYPE: DNA
<213> ORGANISM: Glycine max

<400> SEQUENCE: 23

```
ggaaaatggc agtctatggg atcttctgca tggacctacc aagaagaaaa agcttgattg     60
ggatcttcgt ctaaaaatag cactaggatc agcccaaggg cttgcttatc tacaccatga    120
ttgcagtcca ctcatcattc acagggacgt gaaatcatct aatattttac tagacaaaga    180
ctttgagccc catctcgctg atttcggcat tgcaaaaagt ctatgcccat ctaagaccca    240
cacttcaact tacataatgg gcacaattgg ctacatagac cctgagtatg ctagaacttc    300
ccgcctcact gagaagtccg atgtgtatag ctatggtatc gtattgcttg agcttctaac    360
tgggaggaaa gctgttgaca acgaatcaaa cctccatcat ctgattttgt ccaagacagc    420
taatgatggc gtaatggaaa ccgttgatcc agatattact accacatgca gggacatggg    480
```

-continued

```
agcagtaaaa aaggtttttc agcttgctct tttatgcaca agaagcaac cagtcgatag      540 gcctacaatg catgaagtga ctcgcgtctg ggaagccttg tgccatccat aaccctacca    600
aaacaaactg actcaacaca agtgctgcta cctgattctc agtcatctgc taaaatgcaa    660
tgctacaaag atgaatatgc aaatctcaaa actcctcact tggttaactg tccttccatg    720
agcacctctg atgcacaact cttcctcaaa tttggggaag taatatcaca aaatagtcac    780
tgaggatttt gataatc                                                    797
```

<210> SEQ ID NO 24
<211> LENGTH: 196
<212> TYPE: PRT
<213> ORGANISM: Glycine max

<400> SEQUENCE: 24

```
Glu Asn Gly Ser Leu Trp Asp Leu Leu His Gly Pro Thr Lys Lys Lys
 1               5                  10                  15

Lys Leu Asp Trp Asp Leu Arg Leu Lys Ile Ala Leu Gly Ser Ala Gln
             20                  25                  30

Gly Leu Ala Tyr Leu His His Asp Cys Ser Pro Leu Ile Ile His Arg
         35                  40                  45

Asp Val Lys Ser Ser Asn Ile Leu Leu Asp Lys Asp Phe Glu Pro His
     50                  55                  60

Leu Ala Asp Phe Gly Ile Ala Lys Ser Leu Cys Pro Ser Lys Thr His
 65                  70                  75                  80

Thr Ser Thr Tyr Ile Met Gly Thr Ile Gly Tyr Ile Asp Pro Glu Tyr
                 85                  90                  95

Ala Arg Thr Ser Arg Leu Thr Glu Lys Ser Asp Val Tyr Ser Tyr Gly
            100                 105                 110

Ile Val Leu Leu Glu Leu Leu Thr Gly Arg Lys Ala Val Asp Asn Glu
        115                 120                 125

Ser Asn Leu His His Leu Ile Leu Ser Lys Thr Ala Asn Asp Gly Val
    130                 135                 140

Met Glu Thr Val Asp Pro Asp Ile Thr Thr Thr Cys Arg Asp Met Gly
145                 150                 155                 160

Ala Val Lys Lys Val Phe Gln Leu Ala Leu Leu Cys Thr Lys Lys Gln
                165                 170                 175

Pro Val Asp Arg Pro Thr Met His Glu Val Thr Arg Val Trp Glu Ala
            180                 185                 190

Leu Cys His Pro
        195
```

<210> SEQ ID NO 25
<211> LENGTH: 279
<212> TYPE: DNA
<213> ORGANISM: Glycine max

<400> SEQUENCE: 25

```
agtacagttt ataaatgtgt ccttaaaaat tgcaagccgg tggctatcaa gaagctctat     60
tcccactacc cacaatactt gaaagagttt gagactgagc ttgagacagt tggtagcgtt    120
aagcacagaa atctggtcag tctccaaggc tactctttgt caacgtacgg aaatcttctc    180 tttatgact acatggaaaa tggcagtcta tgggatcttc tgcatggacc taccaagaag    240
aaaaagcttg attgggatct tcgtctaaaa atagcacta                            279
```

<210> SEQ ID NO 26
<211> LENGTH: 93
<212> TYPE: PRT
<213> ORGANISM: Glycine max

<400> SEQUENCE: 26

Ser Thr Val Tyr Lys Cys Val Leu Lys Asn Cys Lys Pro Val Ala Ile
1               5                   10                  15
Lys Lys Leu Tyr Ser His Tyr Pro Gln Tyr Leu Lys Glu Phe Glu Thr
            20                  25                  30
Glu Leu Glu Thr Val Gly Ser Val Lys His Arg Asn Leu Val Ser Leu
        35                  40                  45
Gln Gly Tyr Ser Leu Ser Thr Tyr Gly Asn Leu Leu Phe Tyr Asp Tyr
    50                  55                  60
Met Glu Asn Gly Ser Leu Trp Asp Leu Leu His Gly Pro Thr Lys Lys
65                  70                  75                  80
Lys Lys Leu Asp Trp Asp Leu Arg Leu Lys Ile Ala Leu
                85                  90

<210> SEQ ID NO 27
<211> LENGTH: 2931
<212> TYPE: DNA
<213> ORGANISM: Arabidopsis thaliana

<400> SEQUENCE: 27
atggctctgt ttagagatat tgttcttctt gggtttctct tctgcttgag cttagtagct      60
actgtgactt cagaggaggg agcaacgttg ctggagatta gaagtcatt caaagatgtg     120
aacaatgttc tttatgactg gacaacttca ccttcttcgg attattgtgt ctggagaggt     180
gtgtcttgtg aaaatgtcac cttcaatgtt gttgctctta tttgtcaga tttgaatctt     240
gatggagaaa tctcacctgc tattggagat ctcaagagtc tcttgtcaat tgatctgcga     300
ggtaatcgct tgtctggaca aatccctgat gagattggtg actgttcttc tttgcaaaac     360
ttagacttat ccttcaatga attaagtggt gacataccgt tttcgatttc gaagttgaag     420
caacttgagc agctgattct gaagaataac caattgatag gaccgatccc ttcaacactt     480
tcacagattc aaacctgaa attctggac ttggcacaga ataaactcag tggtgagata     540
ccaagactta tttactggaa tgaagttctt cagtatcttg ggttgcgagg aaacaactta     600
gtcggtaaca tttctccaga tttgtgtcaa ctgactggtc tttggtattt tgacgtaaga     660
aacaacagtt tgactggtag atacctgag acgataggaa attgcactgc cttccaggtt     720
ttggacttgt cctacaatca gctaactggt gagatccctt ttgacatcgg cttcctgcaa     780
gttgcaacat tatcattgca aggcaatcaa ctctctggga agattccatc agtgattggt     840
ctcatgcaag cccttgcagt cttagatcta agtggcaact tgttgagtgg atctattcct     900
ccgattctcg gaaatcttac tttcaccgag aaattgtatt tgcacagtaa caagctgact     960
ggttcaattc cacctgagct tggaaacatg tcaaaactcc attacctgga actcaatgat    1020
aatcatctca cgggtcatat accaccagag cttgggaagc ttactgactt gttttgatctg    1080
aatgtggcca acaatgatct ggaaggacct atacctgatc atctgagctc ttgcacaaat    1140
ctaaacagct aaatgttca tgggaacaag tttagtggca ctataccccg agcatttcaa    1200
aagctagaaa gtatgactta ccttaatctg tccagcaaca atatcaaagg tccaatcccg    1260
gttgagctat ctcgtatcgg taacttagat acattggatc tttccaacaa caagataaat    1320
ggaatcattc cttcttccct tggtgatttg gagcatcttc tcaagatgaa cttgagtaga    1380

| | |
|---|---|
| aatcatataa ctggtgtagt tccaggcgac tttggaaatc taagaagcat catggaaata | 1440 |
| gatctttcaa ataatgatat ctctggccca attccagaag agcttaacca attacagaac | 1500 |
| ataattttgc tgagactgga aaataataac ctgactggta atgttggttc attagccaac | 1560 |
| tgtctcagtc tcactgtatt gaatgtatct cataacaacc tcgtaggtga tatccctaag | 1620 |
| aacaataact tctcaagatt ttcaccagac agcttcattg gcaatcctgg tctttgcggt | 1680 |
| agttggctaa actcaccgtg tcatgattct cgtcgaactg tacgagtgtc aatctctaga | 1740 |
| gcagctattc ttggaatagc tattggggga cttgtgatcc ttctcatggt cttaatagca | 1800 |
| gcttgccgac cgcataatcc tcctcctttt cttgatggat cacttgacaa accagtaact | 1860 |
| tattcgacac cgaagctcgt catccttcat atgaacatgg cactccacgt ttacgaggat | 1920 |
| atcatgagaa tgacagagaa tctaagtgag aagtatatca ttgggcacgg agcatcaagc | 1980 |
| actgtataca aatgtgtttt gaagaattgt aaaccggttg cgattaagcg gctttactct | 2040 |
| cacaacccac agtcaatgaa acagtttgaa acagaactcg agatgctaag tagcatcaag | 2100 |
| cacagaaatc ttgtgagcct acaagcttat tccctctctc acttggggag tcttctgttc | 2160 |
| tatgactatt tggaaaatgg tagcctctgg gatcttcttc atggccctac gaagaaaaag | 2220 |
| actcttgatt gggacacacg gcttaagata gcatatggtg cagcacaagg tttagcttat | 2280 |
| ctacaccatg actgtagtcc aaggatcatt cacagagacg tgaagtcgtc caacattctc | 2340 |
| ttggacaaag acttagaggc tcgtttgaca gattttggaa tagcgaaaag cttgtgtgtg | 2400 |
| tcaaagtcac atacttcaac ttacgtgatg ggcacgatag gttacataga ccccgagtat | 2460 |
| gctcgcactt cacggctcac tgagaaatcc gatgtctaca gttatggaat agtccttctt | 2520 |
| gagttgttaa cccgaaggaa agccgttgat gacgaatcca atctccacca tctgataatg | 2580 |
| tcaaagacgg ggaacaatga agtgatggaa atggcagatc cagacatcac atcgacgtgt | 2640 |
| aaagatctcg gtgtggtgaa gaaagttttc caactggcac tcctatgcac caaaagacag | 2700 |
| ccgaatgatc gacccacaat gcaccaggtg actcgtgttc tcggcagttt tatgctatcg | 2760 |
| gaacaaccac ctgctgcgac tgacacgtca gcgacgctgg ctggttcgtg ctacgtcgat | 2820 |
| gagtatgcaa atctcaagac tcctcattct gtcaattgct cttccatgag tgcttctgat | 2880 |
| gctcaactgt ttcttcggtt tggacaagtt atttctcaga acagtgagta g | 2931 |

<210> SEQ ID NO 28
<211> LENGTH: 2901
<212> TYPE: DNA
<213> ORGANISM: Arabidopsis thaliana

<400> SEQUENCE: 28

| | |
|---|---|
| atgaaggaga agatgcagcg aatggtttta tctttagcaa tggtgggttt tatggttttt | 60 |
| ggtgttgctt cggctatgaa caacgaaggg aaagctctga tggcgataaa aggctctttc | 120 |
| agcaacttag tgaatatgct tttggattgg acgatgttca caacagtga cttgtgttct | 180 |
| tggcgaggtg ttttctgcga caacgttagc tactccgttg tctctctgaa tttgtccagt | 240 |
| ctgaatcttg gagggagat atctccagct attggagacc tacggaattt gcaatcaata | 300 |
| gacttgcaag gtaataaact agcaggtcaa attccagatg agattggaaa ctgtgcttct | 360 |
| cttgtttatc tggatttgtc cgagaatctg ttatatggag atatacccttt ctcaatctct | 420 |
| aaactcaagc agcttgaaac tctgaatctg aagaacaatc agctcacagg tcctgtacca | 480 |
| gcaaccttaa cccagattcc aaaccttaag agacttgatc ttgctggcaa tcatctaacg | 540 |
| ggtgagatat cgagattgct ttactggaat gaagttttgc agtatcttgg attacgaggg | 600 |

-continued

```
aatatgttga ctggaacgtt atcttctgat atgtgtcagc taaccggttt gtggtacttt      660
gatgtgagag gaaataatct aactggaacc atcccggaga gcatcggaaa ttgcacaagc      720
tttcaaatcc tggacatatc ttataatcag ataacaggag agattcctta caatatcggc      780
ttcctccaag ttgctactct gtcacttcaa ggaaacagat tgacgggtag aattccagaa      840
gttattggtc taatgcaggc tcttgctgtt ttggatttga gtgacaatga gcttgttggt      900
cctatcccac cgatacttgg caatctctca tttaccggaa agttgtatct ccatggcaat      960
atgctcactg tccaatccc ctctgagctt gggaatatgt cacgtctcag ctatttgcag      1020
ctaaacgaca ataaactagt gggaactatt ccacctgagc ttggaaagct ggagcaattg      1080
tttgaactga atcttgccaa caaccgttta gtagggccca taccatccaa cattagttca      1140
tgtgcagcct tgaatcaatt caatgttcat gggaacctct tgagtggatc tattccactg      1200
gcgtttcgca atctcgggag cttgactat ctgaatcttt cgtcgaacaa tttcaaggga      1260
aaaataccag ttgagcttgg acatataatc aatcttgaca aactagatct gtctggcaat      1320
aacttctcag gtctatacc attaacgctt ggcgatcttg aacaccttct catattaaat      1380
cttagcagaa accatcttag tggacaatta cctgcagagt ttgggaacct tcgaagcatt      1440
cagatgattg atgtatcatt caatctgctc tccggagtta ttccaactga acttggccaa      1500
ttgcagaatt taaactcttt aatattgaac aacaacaagc ttcatgggaa aattccagat      1560
cagcttacga actgcttcac tcttgtcaat ctgaatgtct ccttcaacaa tctctccggg      1620
atagtcccac caatgaaaaa cttctcacgt tttgctccag ccagctttgt tggaaatcca      1680
tatctttgtg gaaactgggt tggatctatt tgtggtcctt taccgaaatc tcgagtattc      1740
tccagaggtg ctttgatctg cattgttctt ggcgtcatca ctctcctatg tatgattttc      1800
cttgcagttt acaaatcaat gcagcagaag aagattctac aaggctcctc aaaacaagct      1860
gaagggttaa ccaagctagt gattctccac atggacatgg caattcatac atttgatgat      1920
atcatgagag tgactgagaa tcttaacgaa aagtttataa ttggatatgg tgcttctagc      1980
acggtataca aatgtgcatt aaaaagttcc cgacctattg ccattaagcg actctacaat      2040
cagtatccgc ataacttgcg ggaatttgag acagaacttg agaccattgg gagcattagg      2100
cacagaaaca tagtcagctt gcatggatat gccttgtctc ctactggcaa ccttctttc      2160 tatgactaca tggaaaatgg atcactttgg gaccttcttc atgggtcatt gaagaaagtg      2220
aagcttgatt gggagacaag gttgaagata gcggttggag ctgcacaagg actagcctat      2280
cttcaccacg attgtactcc tcgaatcatt caccgtgaca tcaagtcatc gaacatactt      2340
cttgatgaga atttcgaagc acatttatct gatttcggga ttgctaagag cataccagct      2400
agcaaaaccc atgcctcgac ttatgttttg ggaacaattg gttatataga cccagagtat      2460
gctcgtactt cacgaatcaa tgagaaatcc gatatataca gcttcggtat tgttcttctt      2520
gagcttctca ctgggaagaa agcagtggat aacgaagcta acttgcatca actgatattg      2580
tcaaaggctg atgataatac tgtgatggaa gcagttgatc cagaggttac tgtgacttgt      2640
atggacttgg gacatatcag gaagacattt cagctggctc tcttatgcac aaagcgaaac      2700
cctttagaga gacccacaat gcttgaagtc tctagggttc tgctctctct tgtcccatct      2760
ctgcaagtag caaagaagct accttctctt gatcactcaa ccaaaaagct gcagcaagag      2820
aatgaagtta ggaatcctga tgcagaagca tctcaatggt ttgttcagtt ccgtgaagtc      2880
atctccaaaa gtagcatata a                                                2901
```

<210> SEQ ID NO 29
<211> LENGTH: 2985
<212> TYPE: DNA
<213> ORGANISM: Zea mays

<400> SEQUENCE: 29

| | | | | | |
|---|---|---|---|---|---|
| atgcctgtgc | gcagctcagt | ggccatgacg | acgacggccg | cccgtgctct | cgccgccctc | 60 |
| gtgctcgtca | ccgccgccgc | cgccgccgcc | gccgtcgccg | acgatggggc | ggcgctggtg | 120 |
| gagatcaaga | agtccttccg | caacgtcggc | aacgtactgt | acgattgggc | cggcgacgac | 180 |
| tactgctcct | ggcgcggcgt | cctgtgcgac | aacgtcacgt | cgccgtcgc | cgcgctcaac | 240 |
| ctctctggcc | tcaaccttga | gggtgagatc | tctccagccg | tcggcagcct | caagagcctc | 300 |
| gtctccatcg | acctcaagtc | aaatggccta | tccgggcaga | tccctgatga | gattggcgat | 360 |
| tgttcgtcac | ttaggacgct | ggactttca | ttcaacaact | ggacggcga | cataccattt | 420 |
| tcaatatcaa | agctgaagca | cctggagaac | ttgatattga | agaacaaccg | gctgattggt | 480 |
| gcgatcccct | caacattgtc | acagctccca | aatttgaaga | ttctggactt | ggcacaaaac | 540 |
| aaactgactg | gggagatacc | gaggcttatc | tattggaacg | aggttcttca | atacttgggt | 600 |
| ttgcggggaa | atcatttaga | aggaagcctc | tctcctgata | tgtgccagct | tactggcctt | 660 |
| tggtactttg | atgtgaagaa | caatagtttg | actgggcga | taccagacac | cattgggaac | 720 |
| tgtacaagtt | ttcaggtctt | ggatttgtct | tacaaccgct | ttactggacc | aatcccattc | 780 |
| aacattggtt | tcctacaagt | ggctacacta | tccttgcaag | ggacaagtt | cactggccca | 840 |
| attccttcag | taattggcct | tatgcaggct | ctcgctgtcc | tagatctgag | ttacaaccaa | 900 |
| ttatctggtc | ctataccatc | tatactaggc | aacttgacat | acactgagaa | gctgtacatg | 960 |
| caaggcaaca | ggttaactgg | atcgatacca | ccagagctag | gaaatatgtc | aacacttcat | 1020 |
| tacctagaac | tgaatgataa | tcaacttact | gggtcaattc | caccagagct | tggaaggcta | 1080 |
| acaggcttgt | ttgacctgaa | ccctgcgaat | aaccaccttg | aaggaccaat | tcctgacaac | 1140 |
| ctaagttcat | gtgtgaatct | caatagcttc | aatgcttatg | caacaagtt | aaatggaacc | 1200 |
| attcctcgtt | cgctgcggaa | acttgaaagc | atgaccatt | taaatctttc | atcaaatttc | 1260 |
| ataagtggtt | ctattcctat | tgagctatca | aggatcaaca | atttggacac | gttgggctta | 1320 |
| tcctgtaaca | tgatgacggg | tccaattcca | tcatccattg | gcaacctaga | gcatctattg | 1380 |
| aggcttaact | tgagcaagaa | tgatctagtt | ggattcatcc | ctgcggagtt | tggtaatttg | 1440 |
| ggaagtgtca | tggagattga | tttatcctat | aatcatcttg | gtggtctgat | tcctcaagaa | 1500 |
| cttggaatgc | tgcaaaaacct | gatgttgcta | aaactggaaa | acaacaatat | aactggcgat | 1560 |
| gtctcttctc | tgatgaactg | cttcagcctc | aatatcttaa | atgtgtcata | caataattta | 1620 |
| gctggtgctg | tccctactga | caacaacttc | acacggtttt | cacatgacag | cttttaggt | 1680 |
| aatcctggac | tctgtggata | ttggcttggt | tcttcatgtc | gttccactgg | ccaccgagac | 1740 |
| aaaccgccaa | tctcaaaggc | tgccataatt | ggtgttgctg | tgggtggact | tgttatcctc | 1800 |
| ctgatgatct | tagtagctgt | atgcaggcca | caccatccac | ctgcttttaa | agatgccact | 1860 |
| gtaagcaagc | cagtgagcaa | tggtccaccc | aagctgatga | tccttcatat | gaacatggct | 1920 |
| cttcatgtct | ttgatgatat | aatgaggatg | actgagaact | tgagtgagaa | atacatcatt | 1980 |
| ggatacgggg | catcaagtac | agtttataaa | tgtgttctaa | agaattgcaa | accagtggca | 2040 |
| ataaaaaagc | tgtatgccca | ctaccctcag | agccttaagg | aatttgaaac | tgagctcgag | 2100 |
| actgttggta | gcatcaaaca | ccggaatcta | gtcagccttc | aagggtactc | gttgtcacct | 2160 |

```
gttgggaacc tcctcttta tgattatatg gagagtggca gcttatggga tgttttacat    2220
gaaggctcat ccaaggagaa caaacttgac tgggtgactc gcctacggat cgctcttggt    2280
gcagctcaag gcctcgctta ccttcaccat gactgcagcc cacgaataat tcaccgggac    2340
gtaaaatcaa agaatatact cctcgacaaa gattatgagg cccatcttac agacttcggc    2400
atcgctaaga gctatgtgt ctcgaagact cacacgtcaa cctacgtcat gggcactatt    2460
ggttacattg atcccgagta cgcccgcacc tcccgcctca acgagaagtc tgatgtctac    2520
agctacggca tcgttctgct ggagctgctg accggcaaga agccagtgga caacgagtgc    2580
aatctccatc acttgatcct atcgaagacg gcgagcaacg aggtcatgga cacggtggac    2640
cccgacgtgg agacacctg caaggacctg ggcgaggtga agaagctgtt ccagctggcg    2700
ctcctctgca ccaagcggca gccctcggac cggccgacga tgcacgaggt ggtgcgcgtc    2760
cttgactgcc tggtgaaccc ggagccgccc ccgcagccgc agcagcagca gcagaaggcg    2820
cacgcgcacc accagctgcc gccgcagccg tcgccgccgg cctacgtcga cgagtacgtc    2880
agcctgcggg gcaccggcgc cctctcctgc gccaactcgt ccagcacctc ggacgccgag    2940
ctgttcctca agttcggcga ggccatctcg cagaacatgg tgtag    2985

<210> SEQ ID NO 30
<211> LENGTH: 2931
<212> TYPE: DNA
<213> ORGANISM: Zea mays

<400> SEQUENCE: 30
gaaacactgc tggagatcaa gaatccttc cgcgacggcg gcaacgcgct gtacgattgg      60
tccggcgacg cgcgtcgcc gggctactgc tcgtggcgcg cgtgctatg cgacaacgtc     120 accttcgctg tcgcggcgct caacctctct gggctcaatc tcgagggtga aatctcagcg     180
gccatcggga gtctgcaacg tcttgtctca atcgatttga agtcgaatgg actctctgga     240
cagatccccg atgagattgg tgattgttct ttgctcgaaa ctttggattt gtcatctaac     300
aatctagaag gagacatacc attctccatg tccaagctga agcaccttga gaacttgatt     360
ttgaagaaca caaactggt gggagtgatc ccatcgacac tctctcaact tccaaatttg     420
aagatattgg acttggctca aaacaagtta agtggtgaaa ttccgaatct aatatattgg     480
aatgaggttc ttcaatactt gggattgcga agcaatagtt tagaaggaag cctctctccc     540
gatatgtgcc agttaactgg tctgtggtac tttgatgtga agaacaatag cttgacgggt     600
gcaataccag aaaccatagg gaactgtacg agctttcagg tcttagattt gtcaaacaat     660
catcttactg gagaaatccc gttcaatatt ggtttcctgc aagtggctac gttatctttg     720
caagggaaca agttctctgg tcctatacca tcagtgattg gccttatgca ggcgcttgca     780
gtgctagatc tgagtttcaa tgagctatct ggcccaatac cctctatact gggcaacttg     840
acatacactg agaaattata cctgcaaggc aataggttaa ctggattgat accgccagag     900
cttggtaata tgtcgacact gcattacctg gaactgaacg acaatctgtt gactgggttc     960
attcctcctg atcttggaaa acttacagaa ttgtttgaat tgaaccttgc aaacaacaac    1020
cttataggac ctatccctga gaatttaagt tcatgtgcaa atctcattag tttcaatgct    1080
tatggcaata aattgaatgg aaccattcca cgttcatttc acaagcttga gagtctgact    1140
tatctgaatc tgtcatcaaa tcatctcagt ggagcacttc caattgaggt tgcaagaatg    1200
agaaatttgg acactctgga cttatcctgt aacatgatca ctggttcaat tccctcggct    1260
```

```
attgggaaac tagagcatct tttgaggctc aacttaagca aaaataatgt ggctggacac    1320
attcctgctg aatttgggaa cttaaggagc atcatggaga ttgatttgtc ttacaaccac    1380
ctcagtggcc tgattcctca agaggttggg atgctacaaa atttgatact gttaaaatta    1440
gaaagcaata atattactgg agatgtctct tcacttattt actgcttgag tctcaatatc    1500
ttaaatgtat catacaacca tctttatggt actgtaccta cagacaacaa cttctcacga    1560
ttttcacccg acagcttctt gggtaaccct ggactttgtg gctattggct tcactctgct    1620
tcatgcacac aattatccaa tgcagagcaa atgaagagat cctctagcgc aaaggcctca    1680
atgtttgcag ctattggtgt tggtgccgta ttgcttgtta ttatgctcgt tatcctagta    1740
gttatttgct ggccacataa ctctccagtg ctcaaagatg tctctgtaaa caaaccagat    1800
aaccttgctt cagcatcaaa caacattcat cccaagcttg tgatcctcca catgaacatg    1860
gccctctatg tatatgatga tataatgagg atgactgaaa acttgagcga aaaatacatt    1920
attggttatg gagcctcaag tacagtctac agatgcgacc tgaagaactg caagccaatt    1980
gcgattaaaa agctgtatgc tcactaccct cagagcttga aggaattcga gactgaactt    2040
gagactgttg gaagcatcaa acaccggaat cttgtaagcc ttcagggta ctccctgtca    2100 ccatctggga atctcctctt ctatgattac atggaaaatg gcagcctctg gacatttta    2160 catgcttcat cgaagaaaaa gaaactcgat tgggaggctc gcctcaagat tgctctcgga    2220
gctgctcaag gcctggctta tcttcaccat gaatgcagtc cacgaataat ccacagggat    2280
gtgaagtcaa agaatatcct cctagacaaa gactacgagg ctcatcttgc tgacttcggt    2340
attgccaaga gcttgtgtgt gtcgaagacg cacacatcaa cgtacgtgat gggcaccatt    2400
ggctacattg accctgagta tgcacggaca tcccggatca acgagaaatc ggatgtgtac    2460
agctacggca ttgtcttgct ggagctgctt accggcaaaa agcctgtcga cgacgagtgc    2520
aaccttcacc acttgatcct atccaaagcc gcagaaaaca cggtcatgga gacggtagac    2580
caggacatca ccgacacgtg caaggacctc ggcgaggtca agaaggtgtt ccagctggcg    2640
ctcctttgca gcaagaggca gccgtcggat cgaccgacca tgcacgaggt cgcgcgcgtc    2700
ctggacagcc tcgtctgccc agcaggcccg ccccgaagc aggcgcaggc gcaggcacag    2760
gcacaggcgt cggagaagcc gtccaccacg gcgccgagct atgtcagcga gtacgtcggc    2820
ctacgaggcg gcggcggcgg cagcgccctc tcctgcacca actcgtcgag cgcgtccgac    2880
gccgagctct tcatgaagtt tggcgaggtg atctcgcgga gcacggaata g            2931

<210> SEQ ID NO 31
<211> LENGTH: 2937
<212> TYPE: DNA
<213> ORGANISM: Oryza sativa

<400> SEQUENCE: 31
atgacgccgg cgccggcggc cgcctcctac cgcgctctcg tcgcgctcct gctcgtcgcc      60
gtcgccgttg ccgatgatgg gtcgacgctg ctggagatca agaagtcctt ccgcaatgtg     120
gacaacgtac tgtacgattg gccggcggc gactactgct cgtggcgcgg cgtcctctgc     180
gacaacgtca ccttcgccgt cgccgcgctc aacctatccg ggctcaacct cggaggcgag     240
atctctccgg ccgtcggcag gttgaagggc atcgtctcga ttgacttgaa gtcgaatggg     300
ctgtcctggc agatccctga tgagattggc gattgttcat cactaaaaac tctggatttg     360
tctttcaata gcttggatgg ggacattccg ttctcagtat cgaagctgaa gcacattgag     420
agcttgatat tgaagaacaa ccaactgatc ggagtgatcc catcaacgct ctcacagctc     480
```

```
ccaaatttga agattttgga cttggcacag aacaaactga gtggagagat accaagactg    540
atatattgga acgaggttct tcaatacttg ggattacgcg gtaataattt agaaggcagc    600
atctccccag atatatgcca gttgactggg ctttggtact ttgacgtaaa gaacaacagc    660
ttgactgggc cgataccaga aaccattggg aactgtacaa gttttcaggt cttggatttg    720
tcttacaata aactttctgg atcaattcct ttcaacattg gtttcctaca agttgctaca    780
ctatctttgc aagggaacat gtttactggt cctattccat cagttattgg acttatgcag    840
gctctcgctg tactggatct gagttacaac caattgtctg gtcctattcc atcgatacta    900
ggcaatttaa catacactga gaagctgtat atgcaaggca ataagttaac aggtccaata    960
ccacctgagc ttggaaatat gtcaacccct cattacttag aacttaacga taatcaactt   1020
agcgggttca ttcctccaga gttcggaaag ctaacagggt tatttgactt aaaccttgca   1080
aacaacaact ttgaaggtcc aatccctgat aacataagct catgtgtgaa tctcaatagc   1140
ttcaatgctt atggcaacag attaaatggg accattcctc cttcattgca taaacttgag   1200
agcatgactt atttgaattt gtcatcaaat tttctaagtg gttctattcc tattgagcta   1260
tcgagaatca acaatttgga caccttggat ttatcctgta acatgattac tggcccaatt   1320
ccatcaacca ttgggagttt ggagcatcta ttaagactta acttgagcaa caatggtcta   1380
gtaggattca ttcctgcaga aattggcaac ttgaggagta tcatggagat tgatatgtcc   1440
aacaatcatc ttggcggttt gattcctcaa gaactcggaa tgctgcaaaa tctgatgttg   1500
ttaaatctca aaaacaacaa cataactggg gatgtctctt cactgatgaa ctgcttcagc   1560
ctcaatatct taaatgtatc ctataataat ttggctggtg ttgtacctac tgataacaac   1620
ttctcacggt tttcgcctga cagcttttgg ggtaatccag gactttgtgg atattggctt   1680
ggttcttcgt gccgttcatc tggccatcaa cagaaaccac taatctcaaa ggctgcaata   1740
cttgaaattg ccgtgggtgg gcttgttatc ctcctgatga tcttagtagc ggtctgcagg   1800
cctcatagtc cacctgtttt caaagatgtc tctgttagca aaccagtgag caatgttccc   1860
cccaagctgg ttatccttca tatgaacctt tcccttcttg tatacgagga tataatgacg   1920
atgactgaaa acctgagtga gaagtacatc attgggtacg gagcatccag cacggtttat   1980
aaatgtgttt cgaagaaccg caaaccagtg gcagtaaaaa agctatatgc ccactatcca   2040
cagagcttca aggaatttga aactgagctt gagactgttg gtagcatcaa acaccggaat   2100
ctagtcagtc ttcaaggata ttccctatct cctgttggaa atcttctctt ctacgattac   2160
atggaaaatg gaagcctctg ggatgttttg catgaaggtc caactaagaa gaaaaaactt   2220
gattgggaaa ctcgtctacg aattgctcta ggtgcggccc aaggccttgc ttatcttcat   2280
catgactgta gcccacggat aatacacagg gatgtgaaat caaaaatat actccttgat   2340 aaagattatg aggcacatct tacagacttt ggcattgcta agagtttgtg tgtttcaaaa   2400
actcacacgt ccacctatgt catgggaact attggctata tcgatcctga gtatgctcgc   2460
acctcccgtc tcaatgaaaa gtctgatgtc tacagctatg gcattgttct gcttgagctg   2520
ctgaccggaa aaaagccagt ggacaacgag tgcaatctcc atcacttgat cttgtcaaag   2580
acggctaaca atgctgtcat ggagacagtc gacccggaca ttgcagacac ttgcaaggat   2640
cttggtgagg tcaagaaggt gttccagctg gcgctccttt gcaccaagag acaaccatcg   2700
gatcggccga caatgcacga ggttgtgcgc gtcctggact gcctagttcg tcccgacccg   2760
ccaccgaagt ccgcacagca gctggccatg ccgcagcggc ctgctgtccc gagctacatc   2820
```

-continued

| | | |
|---|---|---|
| aacgagtatg tcagcttaag aggcaccagc gtgctctcct gcgccaactc gtcgtgtact | 2880 |
| tccgatgctg agctgtttct caagtttggc gaggtcattt ctcagaacac agagtag | 2937 |

<210> SEQ ID NO 32
<211> LENGTH: 3000
<212> TYPE: DNA
<213> ORGANISM: Oryza sativa

<400> SEQUENCE: 32

| | | |
|---|---|---|
| atggcggcgg cgagggcgcc gtggctgtgg tggtgggtgg tggtggttgt tggtgtggcg | 60 |
| gtggcggagg cggcctccgg aggaggagga gggggagatg gggagggggaa ggcgctgatg | 120 |
| ggcgtgaagg ccggtttcgg gaacgcggcc aacgcgctcg tcgactggga cggcggcgcc | 180 |
| gaccactgcg cgtggcgcgg cgtcacctgc gacaacgcct ccttcgccgt cctcgccctg | 240 |
| aacttgtcaa atctaaacct aggaggtgag atctcgccgg ccatcggaga gctcaagaat | 300 |
| ctacagttcg ttgatctcaa ggggaacaag ctcactggcc aaatcccaga tgagattggg | 360 |
| gactgcatct ccttaaaata tttggatttg tctggcaact tgctgtatgg agacatcccc | 420 |
| ttctccatct ccaagctcaa gcagcttgag gagctgattt tgaagaacaa ccagctcacg | 480 |
| ggacccatcc cttccacatt gtcccaaatt ccaaatctca agacattgga cctggcacag | 540 |
| aaccagctta caggcgatat cccaaggctc atatactgga atgaagttct gcaataccta | 600 |
| ggtttgaggg gtaactcact gactggaact tgtcacctg acatgtgcca actgactggc | 660 |
| ctgtggtact tgatgtaag gggaaacaat ctcacaggga ccattccaga gagcataggg | 720 |
| aactgcacca gctttgagat tctggacatt tcgtataacc aaatctctgg agaaatacct | 780 |
| tacaacatag gctttcttca gtagccaca ctgtcacttc aaggaaatag actgactggg | 840 |
| aaaattccag atgtgattgg cctgatgcaa gctcttgctg ttctagacct gagtgagaac | 900 |
| gagctggtag ggcccattcc ttctatactg ggcaatctat cctatactgg aaaactatat | 960 |
| ttacatggga acaaacttac tggagtcata ccgccggagc ttgggaacat gagtaaactt | 1020 |
| agctacctac aactgaatga taatgaattg gtgggcacaa ttccagcaga gcttggcaaa | 1080 |
| cttgaagagc ttttttgaact aaatcttgcc aacaacaatc ttcaaggtcc tattcctgca | 1140 |
| aacatcagtt cttgcactgc tctaaacaaa ttcaatgttt atggcaataa gctaaatggt | 1200 |
| tctattcctg ctggtttcca gaagttggag agtctgactt acttgaacct atcttcaaac | 1260 |
| aatttcaaag gcaatattcc ttctgagctt ggtcacatca tcaacttgga cacattggat | 1320 |
| ctttcctaca atgaattctc tggaccagtt cctgctacca ttggtgatct agagcacctt | 1380 |
| cttgaactga atttgagtaa gaaccatctt gatgggccag ttcctgctga gtttggaaac | 1440 |
| ttgagaagcg tccaagtaat tgatatgtcc aacaacaact tatctggtag tctgcccgag | 1500 |
| gaacttggac aacttcaaaa ccttgatagc ctgattctta caacaacaa tttggttggg | 1560 |
| gagatccctg ctcaattggc caactgcttc agcttaaata accttgcatt tcaggaattt | 1620 |
| gtcatacaac aatttatctg acatgtcccc gatggcaaag aacttctcga aattcccaat | 1680 |
| ggaaagcatc ttctaatttc tgattgcaac cagtacataa atcataaatg cagcttcttg | 1740 |
| ggtaatccat tactgcatgt ttactgccaa gattccagct gtggacactc tcatggacaa | 1800 |
| agagttaata tttcaaagac agcaattgct tgcattatct taggctttat catattgctc | 1860 |
| tgcgttctgc tgttggctat atataaaaca aatcaaccac agccacttgt caaaggatcc | 1920 |
| gataagccag tgcaaggacc tccaaagcta gttgttctcc agatggacat ggctatccat | 1980 |
| acttacgagg acatcatgag gctgacagag aatttgagcg agaaatacat cattggctat | 2040 |

-continued

| | |
|---|---|
| ggcgcctcaa gcactgtcta caaatgtgaa ctcaagagcg gcaaggccat tgctgtcaag | 2100 |
| cggctttaca gtcagtataa ccatagcctc cgagagtttg aaacagaact agagacaatt | 2160 |
| ggcagcatac ggcacaggaa tcttgttagc ctccatggct tctcgctatc tccacatgga | 2220 |
| aacttgctct tctatgatta catggaaaat ggttccttgt gggatcttct ccacggtcca | 2280 |
| tcaaagaaag tgaagctcaa ctgggacaca agactgagga tcgcggtcgg agctgcacaa | 2340 |
| gggctggcct atctccacca tgactgcaac cctcgcataa tccacagaga tgtcaagtcc | 2400 |
| tccaacatcc tgctcgacga gaacttcgaa gcgcacctct cagatttcgg catagccaaa | 2460 |
| tgtgtcccct ctgccaagtc ccatgcctcc acttatgtgc taggaaccat cggctacatt | 2520 |
| gatccggagt atgccaggac ttccaggctc aatgagaaat ctgatgtgta cagcttcggc | 2580 |
| atcgtccttc tggaattgct cacagggaag aaggccgtcg acaacgaatc gaacttgcat | 2640 |
| caattgatac tctccaaagc tgatgacaac acagtcatgg aggcagtgga ctcggaggtg | 2700 |
| tcagtgacgt gcacggacat gggactggtc aggaaggcct tccagctcgc ccttctgtgc | 2760 |
| accaagaggc acccttcaga ccggccgacc atgcacgagg ttgcaagggt gctgctctcc | 2820 |
| ctgctgccgg cctccgccat gacaacgccc aagacggtgg actactcccg gttgctggcg | 2880 |
| tcgacgacga cggcggccga catgcgaggg cacgacgtga ccgacatcgg cgacaacagc | 2940 |
| tcctccgacg agcagtggtt cgtcaggttc ggcgaggtca tatccaagca cacaatgtga | 3000 |

<210> SEQ ID NO 33
<211> LENGTH: 2790
<212> TYPE: DNA
<213> ORGANISM: Sorghum bicolor

<400> SEQUENCE: 33

| | |
|---|---|
| atgcctgtcc gcagctcagt ggccatgacg acgacggccg cccgtgctct cgtcgccctc | 60 |
| ctcctcgtcg ccgtcgccgt cgccgacgat ggggcgacgc tggtggagat caagaagtcc | 120 |
| ttccgcaacg tcggcaacgt actgtacgat tgggccggcg acgactactg ctcctggcgc | 180 |
| ggcgtcctgt gcgacaacgt cacattcgcc gtcgctgcgc tcaacctctc tggcctcaac | 240 |
| cttgagggcg agatctctcc agccgtcggc agcctcaaga gcctcgtctc catcgatctg | 300 |
| aagtcaaatg gctatccgg gcagatccct gatgagattg tgattgttc tcacttagg | 360 |
| acgctggact tttctttcaa caacttggat ggcgacatac cattctctat atcaaagctg | 420 |
| aagcacctgg agaacttgat attgaagaac aaccagctga ttggtgcgat cccatcaaca | 480 |
| ttgtcacagc tcccaaattt gaagattttg gatttggcac aaaacaaact gactggggag | 540 |
| ataccaaggc ttatctactg gaatgaggtt cttcaatatc ttgatgtgaa gaacaatagc | 600 |
| ttgaccgggg tgataccaga caccattggg aactgtacaa gttttcaagt cttggatttg | 660 |
| tcttacaacc gctttactgg accaatccca ttcaacattg gttcctaca agtggctaca | 720 |
| ctatccttgc aagggaacaa gttcaccggt ccaattcctt cagtaattgg tcttatgcag | 780 |
| gctctcgctg ttctagatct gagttacaac caattatctg gtcctatacc atcaatacta | 840 |
| ggcaacttga catacactga gaagctgtac atccaaggca ataagttaac tgggtcgata | 900 |
| ccaccagagt taggaaatat gtcaacactt cattacctag aactgaacga taatcaactt | 960 |
| actgggtcaa ttccaccaga gcttggaagg ctaacaggct tgtttgacct gaaccttgcg | 1020 |
| aataaccacc tggaaggacc aattcctgac aacctaagtt catgtgtgaa tctcaatagc | 1080 |
| ttcaatgctt atggcaacaa gttaaatggg accattcctc gttcgttgcg gaaacttgaa | 1140 |

```
agcatgacct atttaaatct gtcatcaaac ttcataagtg gctctattcc tattgagtta    1200
tcaaggatca acaatttgga cacgctggat ttatcctgta acatgatgac tggtccaatt    1260
ccatcatcaa ttggcagcct agagcatcta ttgagactta acttgagcaa gaatggtcta    1320
gttggattca tccccgcgga gtttggtaat ttgaggagtg tcatggagat tgatttatcc    1380
tataatcacc ttggtggcct gattcctcaa gaacttgaaa tgctgcaaaa cctgatgttg    1440
ctaaatgtgt cgtacaataa tttggctggt gttgtccctg ctgacaacaa cttcacacgg    1500
ttttcacctg acagcttttt aggtaatcct ggactctgtg gatactggct tggttcgtcg    1560
tgtcgttcca ctggccacca cgagaaaccg cctatctcaa aggctgccat aattggtgtt    1620
gctgtgggtg gacttgttat cctcttgatg atcttagtag ctgtttgcag gccacatcgt    1680
ccacctgctt ttaaagatgt cactgtaagc aagccagtga gaaatgctcc ccccaagctg    1740
gtgatccttc atatgaacat ggcccttcat gtatacgatg acataatgag gatgactgag    1800
aacttgagtg agaaatacat cattggatac ggggcgtcaa gtacagttta taaatgtgtc    1860
ctaaagaatt gcaaaccggt ggcaataaaa aagctgtatg cccactaccc acagagcctt    1920
aaggaatttg aaactgagct tgagactgtt ggtagcatca agcaccggaa tctagtcagc    1980
cttcaagggt actcattatc acctgttggg aacctcctct tttatgatta tatggaatgt    2040
ggcagcttat gggatgtttt acatgaaggt tcatccaaga agaaaaaact tgactgggag    2100
actcgcctac ggattgctct tggtgcagct caaggccttg cttaccttca ccatgactgc    2160
agtccacgga taattcatcg ggatgtaaaa tcaaagaata tactccttga caaagattat    2220
gaggcccatc ttacagactt tggaattgct aagagcttat gtgtctcaaa aactcacaca    2280
tcaacctatg tcatgggaac tattggctac attgatcctg agtacgcccg cacttcccgt    2340
ctcaacgaaa agtctgatgt ctacaggcta tggcattgtt ctgctggagc tgctgactgg    2400
caagaagcca gtggacaacg aatcctatcg aagacggcaa gcaacgaggt catggatacc    2460
gtggaccctg acatcgggga cacctgcaag gacctcggcg aggtgaagaa gctgttccag    2520
ctggcgctcc tttgcaccaa gcggcaaccc tcggaccgac cgacgatgca cgaggtggtg    2580
cgcgtcctgg actgcctggt gaacccggac ccgccgccaa agccgtcggc gcaccagctg    2640
ccgcagccgt cgccagccgt gccaagctac atcaacgagt acgtcagcct gcggggcacc    2700
ggcgctctct cctgcgccaa ctcgaccagc acctcggacg ccgagctgtt cctcaagttc    2760
ggcgaggcca tctcgcagaa catggagtag                                     2790
```

<210> SEQ ID NO 34
<211> LENGTH: 1514
<212> TYPE: DNA
<213> ORGANISM: Sorghum bicolor

<400> SEQUENCE: 34

```
atggcagcga gggcggcggc ggcggtggtg ctgcttattg cggctgtggt gtcggtgtcg     60
gcgggaggag gtgaagggga cggagacggg cagacgctga tggcggtcaa ggcggggttc    120
gggaacgcgg ccaacgcgct ggcggactgg gacggcggcc gcgaccactg cgcctggcgc    180
ggcgtcgcct gcgacgccgc ctctttcgcc gtcgtcggcc tgaacctgtc aaatctaaac    240
ctcggagggg agatctcgcc ggctataggg cagctcaaga gcctacagtt cgtggatctc    300
aagctgaaca agctcacagg ccaaatccca gatgagattg gggattgtgt ctccttaaaa    360
tatttggatt tgtctggaaa cttgctgtat ggagacatcc ccttctccat ctccaagctc    420
aaacagcttg aggacctgat tttgaagaac aaccaactca cgggacccat cccttccaca    480
```

-continued

```
ctgtcccaga ttccaaatct caagaccttg gatctggcgc agaacaagct caccggagac      540
attcccaggc tcatctactg gaatgaagta ctgcaatacc taggcttgag gggcaattca      600
ctgactggaa ctctgtcacc tgatatgtgc caactgactg gcctgtggta ttttgatgta      660 aggggggaaca atctcacagg aacaattcca gagggcatag ggaactgcac tagctttgag     720
attctggata tttcatacaa ccaaatctct ggagaaatac cttacaacat aggttacctt      780
caagtagcca cacttgatct tagcgagaat gaacttgtgg gaccaattcc tccgatactt      840
ggcaacctgt cctacacagg caaactctat ttacatggca acaaactcac gggacatata      900
ccaccagaac tggggaacat gagtaaactt agctacctgc agctgaatga caatgaacta      960
gtgggcacaa tcccagctga gcttggcaaa ctcacagagt tatttgaatt gaatcttgcc     1020
aacaacaatc ttgagggtca tattcctgca acatcagct cttgcagtgc actgaacaaa      1080
ttcaatgtgt atggcaatag actgaatggc tctatccctg ctggtttcca ggagttggag     1140
agtttgacat acctgaacct ttcttcaaac aatttcaaag gccagattcc ctctgagctt     1200
ggtcacatag tcaacttgga cacactagat cttttcctaca atgaattctc tggaccagtt    1260
cctcctacta ttggtgatct cgagcatctt cttgaattga atttgagtaa aaaccatctt     1320
actggatctg tgcctgctga atttggaaac ttgagaagtg tccaagtaat tgacatatcc     1380
agcaacaact tgactggtta tctccctgaa gaacttggac agctgcaaaa ccttgatagc     1440
ttgattctta acaacaacaa tttggttggg gagatccctg ctcagctggc taactgcttc     1500
agcttaatta cctt                                                       1514
```

<210> SEQ ID NO 35
<211> LENGTH: 752
<212> TYPE: DNA
<213> ORGANISM: Sorghum bicolor

<400> SEQUENCE: 35

```
cttcaaatgg acatggctac ccatacctat gaagacatta tgaggttgac tgagaatttg       60
agcgagaaat acatcattgg ttatggggca tcaagtactg tgtacaaatg tgatctcaag      120
ggcggcaaag ccatcgctgt caaacggctt tacagtcagt ataaccacag cctccgtgag      180
tttgagacag aactggagac gatcggtagc atccgacaca ggaatctcgt cagccttcat      240
ggcttctcac tctcccctca tggaaacctg cttttctacg attacatgga aaatggttcc      300
ctgtgggatc ttcttcatgg tccatcaaag aaggtgaagc ttgattggga cacaaggctt      360
aagattgcgg taggtgctgc gcaaggactg gcctatcttc accatgactg caaccctcgc      420
ataatccaca gggatgtcaa gtcctcaaac atcctgctcg acgagaactt cgaagcgcac      480
ctctctgatt tcggcatcgc caaatgtgtc ccggctgcca agtcccatgc ctccacctac      540
gtgcttggaa ccattggcta cattgatcca gagtatgccc gcacgtcgag gctcaatgag      600
aaatcggatg tctacagctt tggcatcgtc cttctggagc tgctcaccgg gaagaaggct      660
gtagacaatg aatccaactt gcaccaattg atactctcaa agctgacgca caacacggtg      720
atggaggctg tggactcgga ggtgtcagtg ac                                    752
```

<210> SEQ ID NO 36
<211> LENGTH: 1323
<212> TYPE: DNA
<213> ORGANISM: Glycine max
<220> FEATURE:
<221> NAME/KEY: misc_feature
<222> LOCATION: 1253

<223> OTHER INFORMATION: n = A,T,C or G
<221> NAME/KEY: misc_feature
<222> LOCATION: 1253
<223> OTHER INFORMATION: n = A,T,C or G

<400> SEQUENCE: 36

```
cttagtctct ctctacttaa tgtgtcctat aacaaactat ttggtgttat ccccacgagt      60
aacaacttta ccaggtttcc ccctgacagt ttcattggaa accctggtct ttgtggtaat     120
tggctgaatt tgccatgcca tggtgctcgt ccttcagagc gagttacatt atctaaggct     180
gccattcttg gaattacttt gggtgcccct gtgattcttc ttatggtatt ggtggcagct     240
tgccgaccac acagccctc tccttttcct gatggatcat ttgacaaacc aattaatttc     300
tcccctccaa agctagtgat tcttcatatg aatatggcac tacatgtgta tgaagatatc     360
atgaggatga ctgaaaacct aagtgagaag tatatcattg gatatggtgc atcaagtaca     420
gtttataaat gtgttcttaa gaattgtaag ccggtggcta tcaagaggat ctattctcac     480
tatccccaat gtattaaaga atttgaaact gaactcgaga ctgttggcag catcaagcac     540
cggaatttgg tcagtctcca aggctactcc ttgtccccat atggccatct cctgttttat     600
gactacatgg aaaatggcag tctatgggat cttcttcatg gacctaccaa gaagaaaaag     660
cttgactggg agctgcgtct aaaaatagca cttggagcag cacaagggct tgcttatcta     720
caccatgatt gctgtcctag aatcatccac agagatgtga atcatctaa cattctattg     780
gatgcagact ttgagcctca tctcactgat tttggcattg ccaaaagtct ctgcccctca     840
aagtcccata cttctactta cataatgggc acaattggct atatagaccc tgagtatgct     900
agaacttcac gtctcactga gaagtctgat gtgtacagtt acggtattgt tttacttgag     960
ttgctaactg gaaggaaagc tgttgacaat gaatccaacc tccaccatct gattttgtcc    1020
aaggcagcaa ccaatgcagt gatggaaaca gttgatccag acattactgc cacatgcaag    1080
gacctaggag ctgtaaaaaa ggtttatcag cttgctctat tatgcacaaa gaggcagcca    1140
gctgataggc cgacaatgca cgaagtgaca cgtgtactcg gaagccttgt gctgtccaac    1200
accccaccaa agcaactagc tgcactacca cctgcttcag atccatctgc canagtgcca    1260
tgctacgtgg atgagtatgg caaacctcaa gactccacac ttggtgaaac tgcccctcaa    1320
tga                                                                  1323
```

<210> SEQ ID NO 37
<211> LENGTH: 492
<212> TYPE: DNA
<213> ORGANISM: Glycine max

<400> SEQUENCE: 37

```
gagtatgcta gaacttcgca tctcactgag aagtctgatg tgtacagtta tggtattgtt      60
ttactcgagt tgctaactgg aaggaaagct gttgacaatg aatccaacct ccaccatctt     120
attttgtcca aggcagcaac caatgctgtg atggaaacag ttgatcccga cattactgcc     180
acatgcaagg acctaggagc tgtaaaaaag gtttatcagc ttgctctatt atgcacaaag     240
aggcagccag ctgataggcc aacaatgcac gaagtgacac gtgtactcgg aagtctcgtg     300
ccatcaagca tccccaccaaa gcaactagct gacctaccac ctgcttcaaa tccatctgcc     360
aaagtgccat gctacgtgga tgagtatgca aacctcaaaa ccccacactt agtaaactgc     420
ccctcaatga gcacttcaga tgctcaactc ttcctcaagt ttggagaagt aatctctcaa     480
aacagtgagt ga                                                         492
```

-continued

```
<210> SEQ ID NO 38
<211> LENGTH: 591
<212> TYPE: DNA
<213> ORGANISM: Glycine max

<400> SEQUENCE: 38
gaaaatggca gtctatggga tcttctgcat ggacctacca agaagaaaaa gcttgattgg      60
gatcttcgtc taaaaatagc actaggatca gcccaagggc ttgcttatct acaccatgat     120
tgcagtccac tcatcattca cagggacgtg aaatcatcta atatttact agacaaagac      180 tttgagcccc atctcgctga tttcggcatt gcaaaaagtc tatgcccatc taagacccac     240
acttcaactt acataatggg cacaattggc tacatagacc ctgagtatgc tagaacttcc     300
cgcctcactg agaagtccga tgtgtatagc atggtatcg tattgcttga gcttctaact      360
gggaggaaag ctgttgacaa cgaatcaaac ctccatcatc tgattttgtc caagacagct     420
aatgatggcg taatggaaac cgttgatcca gatattacta ccacatgcag ggacatggga     480
gcagtaaaaa aggttttca gcttgctctt ttatgcacaa agaagcaacc agtcgatagg      540
cctacaatgc atgaagtgac tcgcgtctgg gaagccttgt gccatccata a              591

<210> SEQ ID NO 39
<211> LENGTH: 279
<212> TYPE: DNA
<213> ORGANISM: Glycine max

<400> SEQUENCE: 39
agtacagttt ataaatgtgt ccttaaaaat tgcaagccgg tggctatcaa gaagctctat      60
tcccactacc cacaatactt gaaagagttt gagactgagc ttgagacagt tggtagcgtt     120
aagcacagaa atctggtcag tctccaaggc tactctttgt caacgtacgg aaatcttctc     180
ttttatgact acatggaaaa tggcagtcta tgggatcttc tgcatggacc taccaagaag     240
aaaaagcttg attgggatct tcgtctaaaa atagcacta                             279

<210> SEQ ID NO 40
<211> LENGTH: 972
<212> TYPE: PRT
<213> ORGANISM: Artificial Sequence
<220> FEATURE:
<223> OTHER INFORMATION: Consensus sequence
<221> NAME/KEY: VARIANT
<222> LOCATION: 2, 3, 4, 5, 6, 9, 10, 13, 16, 17, 19, 20, 21, 22, 24,
      26, 29, 30, 31, 32, 33, 34, 35, 36, 45, 49, 54, 60, 64, 73,
      76, 78, 79, 84, 86, 99, 102, 103, 106, 108, 110, 112, 124,
      127, 134, 136, 138, 151, 158, 180, 182, 184, 186, 189, 204
<223> OTHER INFORMATION: Xaa = Any Amino Acid
<221> NAME/KEY: VARIANT
<222> LOCATION: 206, 210, 222, 230, 231, 234, 253, 254, 257, 260, 275,
      277, 279, 284, 293, 298, 305, 315, 317, 320, 325, 327, 329, 332,
      338, 339, 349, 351, 356, 362, 363, 366, 369, 375, 380, 381,
      382, 383, 384, 397, 398, 399, 401, 404, 407, 408, 410
<223> OTHER INFORMATION: Xaa = Any Amino Acid
<221> NAME/KEY: VARIANT
<222> LOCATION: 419, 421, 422, 425, 428, 432, 438, 445, 447, 449, 461,
      462, 467, 469, 471, 473, 476, 479, 480, 485, 486, 488, 490, 491,
      493, 495, 497, 499, 500, 501, 503, 504, 506, 509, 510, 512,
      513, 514, 516, 518, 520, 522, 524, 525, 526, 532, 533
<223> OTHER INFORMATION: Xaa = Any Amino Acid
<221> NAME/KEY: VARIANT
<222> LOCATION: 534, 541, 545, 548, 549, 550, 551, 552, 553, 554, 555,
      556, 557, 558, 559, 560, 561, 562, 563, 564, 565, 566, 567, 568,
      569, 570, 571, 572, 574, 575, 576, 577, 579, 581, 582, 583,
      587, 591, 594, 595, 596, 597, 598, 599, 600, 601, 602
<223> OTHER INFORMATION: Xaa = Any Amino Acid
<221> NAME/KEY: VARIANT
<222> LOCATION: 603, 605, 606, 607, 608, 609, 610, 612, 614, 615, 616,
```

```
        617, 618, 619, 620, 621, 622, 623, 632, 637, 666, 670, 715, 736,
        737, 778, 784, 801, 864, 866, 868, 879, 886, 912, 916, 920,
        921, 922, 923, 926, 927, 928, 929, 930, 931, 932, 933
<223> OTHER INFORMATION: Xaa = Any Amino Acid
<221> NAME/KEY: VARIANT
<222> LOCATION: 934, 935, 936, 937, 938, 939, 940, 941, 942, 943, 944,
        945, 946, 947, 948, 949, 950, 953, 956, 957, 958, 960, 961, 962,
        963, 964, 965, 966, 968, 969, 970, 971
<223> OTHER INFORMATION: Xaa = Any Amino Acid

<400> SEQUENCE: 40

Ala Xaa Xaa Xaa Xaa Asp Gly Xaa Xaa Leu Leu Xaa Ile Lys Xaa
 1               5                  10                  15

Xaa Phe Xaa Xaa Xaa Asn Xaa Leu Xaa Asp Trp Xaa Xaa Xaa Xaa
                20                  25                  30

Xaa Xaa Xaa Xaa Asp Tyr Cys Ser Trp Arg Gly Val Xaa Cys Asp Asn
            35                  40                  45

Xaa Thr Phe Ala Val Xaa Ala Leu Asn Leu Ser Xaa Leu Asn Leu Xaa
 50                  55                  60

Gly Glu Ile Ser Pro Ala Ile Gly Xaa Leu Lys Xaa Leu Xaa Xaa Ile
 65                  70                  75                  80

Asp Leu Lys Xaa Asn Xaa Leu Ser Gly Gln Ile Pro Asp Glu Ile Gly
                85                  90                  95

Asp Cys Xaa Ser Leu Xaa Xaa Leu Asp Xaa Ser Xaa Asn Xaa Leu Xaa
            100                 105                 110

Gly Asp Ile Pro Phe Ser Ile Ser Lys Leu Lys Xaa Leu Glu Xaa Leu
            115                 120                 125

Ile Leu Lys Asn Asn Xaa Leu Xaa Gly Xaa Ile Pro Ser Thr Leu Ser
 130                 135                 140

Gln Ile Pro Asn Leu Lys Xaa Leu Asp Leu Ala Gln Asn Xaa Leu Thr
 145                 150                 155                 160

Gly Glu Ile Pro Arg Leu Ile Tyr Trp Asn Glu Val Leu Gln Tyr Leu
                165                 170                 175

Gly Leu Arg Xaa Asn Xaa Leu Xaa Gly Xaa Leu Ser Xaa Asp Met Cys
            180                 185                 190

Gln Leu Thr Gly Leu Trp Tyr Phe Asp Val Lys Xaa Asn Xaa Leu Thr
            195                 200                 205

Gly Xaa Ile Pro Glu Thr Ile Gly Asn Cys Thr Ser Phe Xaa Val Leu
 210                 215                 220

Asp Leu Ser Tyr Asn Xaa Xaa Thr Gly Xaa Ile Pro Phe Asn Ile Gly
 225                 230                 235                 240

Phe Leu Gln Val Ala Thr Leu Ser Leu Gln Gly Asn Xaa Xaa Thr Gly
                245                 250                 255

Xaa Ile Pro Xaa Val Ile Gly Leu Met Gln Ala Leu Ala Val Leu Asp
            260                 265                 270

Leu Ser Xaa Asn Xaa Leu Xaa Gly Pro Ile Pro Xaa Ile Leu Gly Asn
            275                 280                 285

Leu Thr Tyr Thr Xaa Lys Leu Tyr Leu Xaa Gly Asn Lys Leu Thr Gly
            290                 295                 300

Xaa Ile Pro Pro Glu Leu Gly Asn Met Ser Xaa Leu Xaa Tyr Leu Xaa
 305                 310                 315                 320

Leu Asn Asp Asn Xaa Leu Xaa Gly Xaa Ile Pro Xaa Glu Leu Gly Lys
            325                 330                 335

Leu Xaa Xaa Leu Phe Asp Leu Asn Leu Ala Asn Asn Xaa Leu Xaa Gly
            340                 345                 350

Pro Ile Pro Xaa Asn Ile Ser Ser Cys Xaa Xaa Leu Asn Xaa Phe Asn
```

-continued

```
                355                 360                 365
Xaa Tyr Gly Asn Lys Leu Xaa Gly Thr Ile Pro Xaa Xaa Xaa Xaa Xaa
    370                 375                 380
Leu Glu Ser Leu Thr Tyr Leu Asn Leu Ser Ser Asn Xaa Xaa Xaa Gly
385                 390                 395                 400
Xaa Ile Pro Xaa Glu Leu Xaa Xaa Ile Xaa Asn Leu Asp Thr Leu Asp
                405                 410                 415
Leu Ser Xaa Asn Xaa Xaa Thr Gly Xaa Ile Pro Xaa Thr Ile Gly Xaa
            420                 425                 430
Leu Glu His Leu Leu Xaa Leu Asn Leu Ser Lys Asn Xaa Leu Xaa Gly
                435                 440                 445
Xaa Ile Pro Ala Glu Phe Gly Asn Leu Arg Ser Ile Xaa Xaa Ile Asp
    450                 455                 460
Leu Ser Xaa Asn Xaa Leu Xaa Gly Xaa Ile Pro Xaa Glu Leu Xaa Xaa
465                 470                 475                 480
Leu Gln Asn Leu Xaa Xaa Leu Xaa Leu Xaa Xaa Asn Xaa Leu Xaa Gly
                485                 490                 495
Xaa Val Xaa Xaa Xaa Leu Xaa Xaa Cys Xaa Ser Leu Xaa Xaa Leu Xaa
            500                 505                 510
Xaa Xaa Asn Xaa Leu Xaa Gly Xaa Val Xaa Pro Xaa Xaa Xaa Asn Phe
            515                 520                 525
Ser Arg Phe Xaa Xaa Xaa Ser Phe Leu Gly Asn Pro Xaa Leu Cys Gly
            530                 535                 540
Xaa Trp Leu Xaa Xaa Xaa Xaa Xaa Xaa Xaa Xaa Xaa Xaa Xaa Xaa Xaa
545                 550                 555                 560
Xaa Xaa Xaa Xaa Xaa Xaa Xaa Xaa Xaa Xaa Xaa Ser Xaa Xaa Xaa
                565                 570                 575
Xaa Ile Xaa Ile Xaa Xaa Xaa Gly Leu Val Xaa Leu Leu Met Xaa Leu
            580                 585                 590
Val Xaa Xaa Xaa Xaa Xaa Xaa Xaa Xaa Phe Xaa Xaa Xaa
            595                 600                 605
Xaa Xaa Lys Xaa Val Xaa Xaa Xaa Xaa Xaa Xaa Xaa Xaa Pro
    610                 615                 620
Lys Leu Val Ile Leu His Met Xaa Met Ala Leu His Xaa Tyr Glu Asp
625                 630                 635                 640
Ile Met Arg Met Thr Glu Asn Leu Ser Glu Lys Tyr Ile Ile Gly Tyr
                645                 650                 655
Gly Ala Ser Ser Thr Val Tyr Lys Cys Xaa Leu Lys Asn Xaa Lys Pro
            660                 665                 670
Val Ala Ile Lys Lys Leu Tyr Ser His Tyr Pro Gln Ser Leu Lys Glu
            675                 680                 685
Phe Glu Thr Glu Leu Glu Thr Val Gly Ser Ile Lys His Arg Asn Leu
    690                 695                 700
Val Ser Leu Gln Gly Tyr Ser Leu Ser Pro Xaa Gly Asn Leu Leu Phe
705                 710                 715                 720
Tyr Asp Tyr Met Glu Asn Gly Ser Leu Trp Asp Leu Leu His Gly Xaa
                725                 730                 735
Xaa Ser Lys Lys Lys Lys Leu Asp Trp Asp Thr Arg Leu Lys Ile Ala
            740                 745                 750
Leu Gly Ala Ala Gln Gly Leu Ala Tyr Leu His His Asp Cys Ser Pro
            755                 760                 765
Arg Ile Ile His Arg Asp Val Lys Ser Xaa Asn Ile Leu Leu Asp Xaa
    770                 775                 780
```

-continued

```
Asp Phe Glu Ala His Leu Thr Asp Phe Gly Ile Ala Lys Ser Leu Cys
785                 790                 795                 800

Xaa Ser Lys Thr His Thr Ser Thr Tyr Val Met Gly Thr Ile Gly Tyr
                805                 810                 815

Ile Asp Pro Glu Tyr Ala Arg Thr Ser Arg Leu Asn Glu Lys Ser Asp
            820                 825                 830

Val Tyr Ser Tyr Gly Ile Val Leu Leu Glu Leu Leu Thr Gly Lys Lys
        835                 840                 845

Ala Val Asp Asn Glu Ser Asn Leu His His Leu Ile Leu Ser Lys Xaa
        850                 855                 860

Ala Xaa Asn Xaa Val Met Glu Thr Val Asp Pro Asp Ile Thr Xaa Thr
865                 870                 875                 880

Cys Lys Asp Leu Gly Xaa Val Lys Lys Val Phe Gln Leu Ala Leu Leu
            885                 890                 895

Cys Thr Lys Arg Gln Pro Ser Asp Arg Pro Thr Met His Glu Val Xaa
            900                 905                 910

Arg Val Leu Xaa Ser Leu Val Xaa Xaa Xaa Pro Pro Xaa Xaa Xaa
            915                 920                 925

Xaa Xaa Xaa Xaa Xaa Xaa Xaa Xaa Xaa Xaa Xaa Xaa Xaa Xaa Xaa
        930                 935                 940

Xaa Xaa Xaa Xaa Xaa Xaa Tyr Val Xaa Glu Tyr Xaa Xaa Xaa Arg Xaa
945                 950                 955                 960

Xaa Xaa Xaa Xaa Xaa Xaa Leu Xaa Xaa Xaa Xaa Ser
            965                 970
```

MAIZE ERECTA GENES FOR IMPROVING PLANT GROWTH, TRANSPIRATION, EFFICIENCY AND DROUGHT TOLERANCE IN CROP PLANTS

CROSS REFERENCE

This utility application claims the benefit U.S. Provisional Application No. 60/847,304, filed Sep. 25, 2006, which is incorporated herein by reference.

FIELD OF THE INVENTION

The invention relates generally to the field of molecular biology.

BACKGROUND OF THE INVENTION

The domestication of many plants has correlated with dramatic increases in yield. Most phenotypic variation occurring in natural populations is continuous and is effected by multiple gene influences. The identification of specific genes responsible for the dramatic differences in yield, in domesticated plants, has become an important focus of agricultural research.

In *Arabidopsis*, the ERECTA gene has been shown to control organ growth and flower development by promoting cell proliferation (Shpak, et al., (2003) *Plant Cell* 15:1095-1110; *Development* (2004) 131:1491-501). The *Arabidopsis* ERECTA gene affects inflorescence development, and controls organ growth by promoting cell proliferation. Transgenic *Arabidopsis* plants that ectopically over express the ERECTA gene improve plant transpiration efficiency and drought tolerance by affecting stomatal density, epidermal cell expansion, mesophyll cell proliferation and cell-cell contact. The ERECTA gene encodes a leucine-rich repeat receptor-like kinase (LRR-RLK) and may controlling plant growth/organ size and biomass accumulation. In addition, Masle Gilmore and Farquhar, *Nature* (2005) 436:866, indicates that the *Arabidopsis* ERECTA gene is responsible for plant transformation efficiency, in addition to the varied effects it is already known to have on plant architecture. There are implications for agriculture, especially in the area of drought tolerance and agronomic performance.

ERECTA is associated with growth enhancement. The ERECTA genes may find utility in controlling the size of the whole plants, or specific organs in maize or other crops. Potential usage of this gene are over expressing it in transgenics to increase biomass accumulation, targeting the gene expression to specific tissues using tissue-specific promoters for enhanced root growth, accelerated seedling growth for fast canopy closure, larger leaf, increased ear size, enhanced embryo, endosperm growth for larger kernel and manipulate the content of oil, protein or starch in the whole kernel, and etc. By altering the silk growth rate one could manipulate the synchronization or ASI (anthesis and silking interval), which may improve stress tolerance. Another potential application is in improving the transformation and regeneration of crop plants from in vitro tissue culture. One could control the expression of this gene to increase cell proliferation rate and cultured tissue growth rate. ERECTA could also be used to manipulate the gene to reduce the organ size such as tassel size by down regulation of the expression in specific tissues. The ERECTA genes can be useful for enhancing drought tolerance by improving the transpiration efficiency in maize and other crops. Exploring natural allelic variation of this gene can be used in breeding improvement or transgenics by identifying allele haplotypes that are associated with the stress tolerant phenotypes of inbreds. The gene maps to a chromosomal location in the general vicinity of drought QTLs, suggesting possibly tolerant allele variants.

The present invention includes the identification of the putative maize ERECTA genes, ZmERECTA A and B (SEQ ID NOS: 5 and 7) that are related to the *Arabidopsis* ERECTA genes (SEQ ID NOS: 1 and 3). The ortholog having the most similarity to *Arabidopsis* ERECTA (SEQ ID NO: 1), is ZmERECTA 1 (SEQ ID NO: 5). The expression is associated with immature reproductive tissues, and is found mainly in the inflorescence meristem and shoot apical meristem and to a lesser degree in other meristem related tissues.

Transgenic plants expressing ZmERECTA A (SEQ ID NO: 5) are expected to show a positive impact on biomass accumulation and rate of maize plant growth, as well as an increase in organ size. Transgenic plants expressing ZmERECTA are also expected to show improved drought tolerance. These maize genes will find utility for enhancing agronomic traits in maize (and other crops).

The present invention also includes the identification of ERECTA genes in other plant species. The rice gene family is represented by 2 family members. Four gene sequences were also found in Soybean (*Glycine max*) and 3 genes in *Sorghum bicolor*. Two members of the ERECTA *Arabidopsis* gene family are disclosed herein.

BRIEF SUMMARY OF THE INVENTION

Compositions and methods for controlling plant growth and organ size for increasing yield in a plant are provided. The compositions include ERECTA sequences from maize, soybean, arabidopsis, rice and sorghum. Compositions of the invention comprise amino acid sequences and nucleotide sequences selected from SEQ ID NOS: 5-8 as well as variants and fragments thereof.

Polynucleotides encoding the ERECTA sequences are provided in DNA constructs for expression in a plant of interest. Expression cassettes, plants, plant cells, plant parts, and seeds comprising the sequences of the invention are further provided. In specific embodiments, the polynucleotide is operably linked to a constitutive promoter.

Methods for modulating the level of an ERECTA sequence in a plant or plant part is provided. The methods comprise introducing into a plant or plant part a heterologous polynucleotide comprising an ERECTA sequence of the invention. The level of ERECTA polypeptide can be increased or decreased. Such method can be used to increase the yield in plants; in one embodiment, the method is used to increase grain yield in cereals.

BRIEF DESCRIPTION OF THE DRAWINGS

FIG. 2: Alignment of ERECTA sequences from maize, *Arabidopsis*, rice, sorghum and soybean showing consensus sequence and conserved regions.

DETAILED DESCRIPTION OF THE INVENTION

Figure 1:
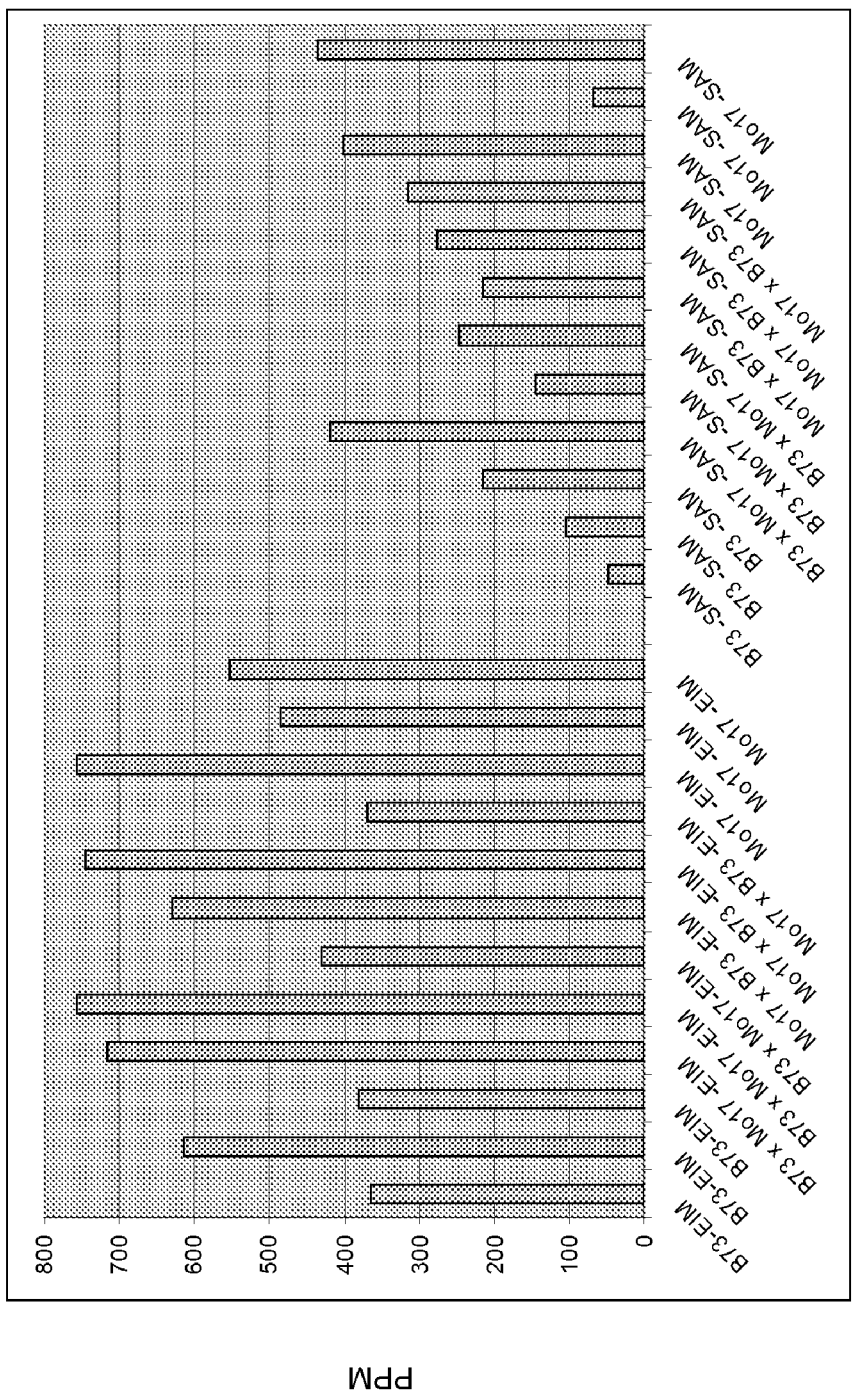
FIG. 1: MPSS expression of the ZmERECTA-A in three stages of the ear inflorescence meristem (EIM) and shoot apical meristem (SAM), of B73, Mo17, B73×Mo17 F1 hybrid, and Mo17×B73 F1 hybrid (MG 6006. 42, 44). The gene is highly expressed in the ear inflorescence meristem, and at slightly lower level in the shoot apical meristem.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation To Human Affairs* John Wiley; *Cell Culture and Somatic Cell Genetics of Plants* (1984) vol. 1, Vasil, ed.; Stanier, et al., (1986) *The Microbial World* 5$^{th}$ ed., Prentice-Hall; Dhringra and Sinclair, (1985) *Basic Plant Pathology Methods*, CRC Press; Maniatis, et al., (1982) *Molecular Cloning: A Laboratory Manual*; DNA Cloning, vols. I and II, (1985) Glover, ed.; *Oligonucleotide Synthesis*, (1985) Gait, ed.; *Nucleic Acid Hybridization*, (1984) Hames and Higgins, eds.; and the series *Methods In Enzymology*, Colowick and Kaplan, eds, Academic Press, Inc., San Diego, Calif.

Units, prefixes, and symbols may be denoted in their Si accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, (1993) Persing et al., eds., American Society for Microbiology, Washington, D.C. The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins*, (1984) W.H. Freeman and Co.

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (Yamao, et al., (1985) *Proc. Natl. Acad. Sci. USA* 82:2306-9), or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "ERECTA nucleic acid" means a nucleic acid comprising a polynucleotide ("ERECTA polynucleotide") encoding a ERECTA polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide To Molecular Cloning Techniques*, from the series *Methods In Enzymology*, vol. 152, Academic Press, Inc., San Diego, Calif. (1987); Sambrook, et al., (1989) *Molecular Cloning: A Laboratory Manual*, 2$^{nd}$ ed., vols. 1-3; and *Current Protocols In Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Dau-*

*cus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

As used herein, "yield" includes reference to bushels per acre of a grain crop at harvest, as adjusted for grain moisture (15% typically). Grain moisture is measured in the grain at harvest. The adjusted test weight of grain is determined to be the weight in pounds per bushel, adjusted for grain moisture level at harvest.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "ERECTA polypeptide" refers to one or more amino acid sequences. The term is also inclusive of fragments, variants, homologs, alleles or precursors (e.g., preproproteins or proproteins) thereof. A "ERECTA protein" comprises a ERECTA polypeptide. Unless otherwise stated, the term "ERECTA nucleic acid" means a nucleic acid comprising a polynucleotide ("ERECTA polynucleotide") encoding a ERECTA polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., (1984) 138:267-84: $T_m=81.5° C.+16.6(\log M)+0.41(\% GC)-0.61(\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques In Biochemistry and Molecular Biology—Hybridization with Nucleic Acid Probes, part I, chapter 2, "Overview of principles of hybridization and the strategy of nucleic acid probe assays," Elsevier, N.Y. (1993); and Current Protocols In Molecular Biology, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG®) programs (Accelrys, Inc., San Diego, Calif.).). The CLUSTAL program is well described by Higgins and Sharp, (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65, and Pearson, et al., (1994) Meth. Mol. Biol. 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The invention discloses ERECTA polynucleotides and polypeptides. The novel nucleotides and proteins of the invention have an expression pattern which indicates that they play an important role in plant development. The polynucleotides are expressed in various plant tissues. The polynucleotides and polypeptides thus provide an opportunity to manipulate plant development to alter seed and vegetative tissue development, timing or composition. This may be used to create a sterile plant, a seedless plant or a plant with altered endosperm composition.

TABLE 1

Sequence identification

| Name | Species | SEQ ID NO: polynucleotide | SEQ ID NO: polypeptide | SEQ ID NO: Open reading frame of polynucleotide |
|---|---|---|---|---|
| AtERECTA | Arabidopsis thaliana | 1 | 2 | 27 |
| AtERECTA-like | Arabidopsis thaliana | 3 | 4 | 28 |
| ZmERECTA A | Zea mays | 5 | 6 | 29 |
| ZmERECTA B | Zea mays | 7 | 8 | 30 |
| OsERECTA A | Oryza sativa | 9 | 10 | 31 |
| OsERECTA B | Oryza sativa | 11 | 12 | 32 |
| SbERECTA A | Sorghum bicolor | 13 | 14 | 33 |
| SbERECTA B | Sorghum bicolor | 15 | 16 | 34 |
| SbERECTA C | Sorghum bicolor | 17 | 18 | 35 |
| GmERECTA A | Glycine max | 19 | 20 | 36 |
| GmERECTA B | Glycine max | 21 | 22 | 37 |
| GmERECTA C | Glycine max | 23 | 24 | 38 |
| GmERECTA D | Glycine max | 25 | 26 | 39 |

Nucleic Acids

The present invention provides, inter alia, isolated nucleic acids of RNA, DNA, and analogs and/or chimeras thereof, comprising a ERECTA polynucleotide.

The present invention also includes polynucleotides optimized for expression in different organisms. For example, for expression of the polynucleotide in a maize plant, the sequence can be altered to account for specific codon preferences and to alter GC content as according to Murray, et al, supra. Maize codon usage for 28 genes from maize plants is listed in Table 4 of Murray, et al., supra.

The ERECTA nucleic acids of the present invention comprise isolated ERECTA polynucleotides which are inclusive of:
  (a) a polynucleotide encoding a ERECTA polypeptide and conservatively modified and polymorphic variants thereof;
  (b) a polynucleotide having at least 70% sequence identity with polynucleotides of (a) or (b);
  (c) complementary sequences of polynucleotides of (a) or (b).

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20): 1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395; or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in WO publication number 97/20078. See also, Zhang, et al. (1997), *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683, 439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30); and maize H3 histone (Lepetit, et al., (1992) *Mol. Gen. Genet.*

231:276-85; and Atanassvoa, et al., (1992) *Plant Journal* 2(3):291-300); ALS promoter, as described in PCT Application Number WO 96/30530; GOS2 (U.S. Pat. No. 6,504,083) and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters (Rab17, RAD29). Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50; and An, et al., (1989) *Plant Cell* 1:115-22); and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell. Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook, Chapter* 116, Freeling and Walbot, eds., Springer, N.Y. (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference), or signal peptides which target proteins to the plastids such as that of rapeseed enoyl-Acp reductase (Verwaert, et al., (1994) *Plant Mol. Biol.* 26:189-202) are useful in the invention. The barley alpha amylase signal sequence fused to the ERECTA polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11, and Berger et al., (1989) *Proc. Natl. Acad. Sci. USA,* 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the gene for ERECTA placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert a ERECTA polynucleotide into a plant host, including biological and physical plant transformation protocols. See, e.g., Miki, et al., "Procedure for Introducing Foreign DNA into Plants," in *Methods In Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch, et al., (1985) *Science* 227:1229-31), electroporation, micro-injection, and biolistic bombardment.

Expression cassettes and vectors and in vitro culture methods for plant cell or tissue transformation and regeneration of plants are known and available. See, e.g., Gruber, et al., "Vectors for Plant Transformation," in *Methods In Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., Direct DNA Transfer into Intact Plant Cells Via Microprojectile Bombardment. pp. 197-213 in *Plant Cell, Tissue and Organ Culture, Fundamental Methods* eds. O. L. Gamborg & G. C. Phillips. Springer-Verlag Berlin Heidelberg N.Y., 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas (1984) *Nature* (London) 311:763-764; Bytebier, et al., (1987) *Proc. Natl. Acad. Sci. USA* 84:5345-5349 (Liliaceae); De Wet, et al., (1985) In *The Experimental Manipulation of Ovule Tissues*, ed. G. P. Chapman, et al., pp. 197-209. Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. patent application Ser. No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application Number 604 662 A1 discloses a method for transforming monocots using *Agrobacterium*. European Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., in *Abstracts of the VIIth Int'l. Congress on Plant Cell and Tissue Culture IAPTC*, A2-38, p. 53 (1990); D'Halluin, et al., (1992) *Plant Cell* 4:1495-505; and Spencer, et al., (1994) *Plant Mol. Biol.* 24:51-61.

Increasing the Activity and/or Level of a ERECTA Polypeptide

Methods are provided to increase the activity and/or level of the ERECTA polypeptide of the invention. An increase in the level and/or activity of the ERECTA polypeptide of the invention can be achieved by providing to the plant an ERECTA polypeptide. The ERECTA polypeptide can be provided by introducing the amino acid sequence encoding the ERECTA polypeptide into the plant, introducing into the plant a nucleotide sequence encoding an ERECTA polypeptide or alternatively by modifying a genomic locus encoding the ERECTA polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having plant growth regulating activity. It is also recognized that the methods of the invention may employ a polynucleotide that is not capable of directing, in the transformed plant, the expression of a protein or an RNA. Thus, the level and/or activity of an ERECTA polypeptide may be increased by altering the gene encoding the ERECTA polypeptide or its promoter. See, e.g., Kmiec, U.S. Pat. No. 5,565,350; Zarling, et al., PCT/US93/03868. Therefore mutagenized plants that carry mutations in ERECTA genes, where the mutations increase expression of the ERECTA gene or increase the plant growth and/or organ development activity of the encoded ERECTA polypeptide are provided.

Reducing the Activity and/or Level of a ERECTA Polypeptide

Methods are provided to reduce or eliminate the activity of an ERECTA polypeptide of the invention by transforming a plant cell with an expression cassette that expresses a polynucleotide that inhibits the expression of the ERECTA polypeptide. The polynucleotide may inhibit the expression of the ERECTA polypeptide directly, by preventing translation of the ERECTA messenger RNA, or indirectly, by encoding a polypeptide that inhibits the transcription or translation of a ERECTA gene encoding a ERECTA polypeptide. Methods for inhibiting or eliminating the expression of a gene in a plant are well known in the art, and any such method may be used in the present invention to inhibit the expression of an ERECTA polypeptide.

In accordance with the present invention, the expression of a ERECTA polypeptide is inhibited if the protein level of the ERECTA polypeptide is less than 70% of the protein level of the same ERECTA polypeptide in a plant that has not been genetically modified or mutagenized to inhibit the expression of that ERECTA polypeptide. In particular embodiments of the invention, the protein level of the ERECTA polypeptide in a modified plant according to the invention is less than 60%, less than 50%, less than 40%, less than 30%, less than 20%, less than 10%, less than 5% or less than 2% of the protein level of the same ERECTA polypeptide in a plant that is not a mutant or that has not been genetically modified to inhibit the expression of that ERECTA polypeptide. The expression level of the ERECTA polypeptide may be measured directly, for example, by assaying for the level of ERECTA polypeptide expressed in the plant cell or plant, or indirectly, for example, by measuring the plant growth and/or organ development activity of the ERECTA polypeptide in the plant cell or plant, or by measuring the biomass in the plant. Methods for performing such assays are described elsewhere herein.

In other embodiments of the invention, the activity of the ERECTA polypeptides is reduced or eliminated by transforming a plant cell with an expression cassette comprising a polynucleotide encoding a polypeptide that inhibits the activity of a ERECTA polypeptide. The plant growth and/or organ development activity of a ERECTA polypeptide is inhibited according to the present invention if the plant growth and/or organ development activity of the ERECTA polypeptide is less than 70% of the plant growth and/or organ development activity of the same ERECTA polypeptide in a plant that has not been modified to inhibit the plant growth and/or organ development activity of that ERECTA polypeptide. In particular embodiments of the invention, the plant growth and/or organ development activity of the ERECTA polypeptide in a modified plant according to the invention is less than 60%, less than 50%, less than 40%, less than 30%, less than 20%, less than 10%, or less than 5% of the plant growth and/or organ development activity of the same ERECTA polypeptide in a plant that that has not been modified to inhibit the expression of that ERECTA polypeptide. The plant growth and/or organ development activity of an ERECTA polypeptide is "eliminated" according to the invention when it is not detectable by the assay methods described elsewhere herein. Methods of determining the plant growth and/or organ development activity of an ERECTA polypeptide are described elsewhere herein.

In other embodiments, the activity of an ERECTA polypeptide may be reduced or eliminated by disrupting the gene encoding the ERECTA polypeptide. The invention encompasses mutagenized plants that carry mutations in ERECTA genes, where the mutations reduce expression of the ERECTA gene or inhibit the plant growth and/or organ development activity of the encoded ERECTA polypeptide.

Thus, many methods may be used to reduce or eliminate the activity of an ERECTA polypeptide. In addition, more than one method may be used to reduce the activity of a single ERECTA polypeptide. Non-limiting examples of methods of reducing or eliminating the expression of ERECTA polypeptides are given below.

1. Polynucleotide-Based Methods:

In some embodiments of the present invention, a plant is transformed with an expression cassette that is capable of expressing a polynucleotide that inhibits the expression of an ERECTA polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one ERECTA polypeptide is an expression cassette capable of producing an RNA molecule that inhibits the transcription and/or translation of at least one ERECTA polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an ERECTA polypeptide are given below.

i. Sense Suppression/Cosuppression

In some embodiments of the invention, inhibition of the expression of a ERECTA polypeptide may be obtained by sense suppression or cosuppression. For cosuppression, an expression cassette is designed to express an RNA molecule corresponding to all or part of a messenger RNA encoding an ERECTA polypeptide in the "sense" orientation. Over expression of the RNA molecule can result in reduced expression of the native gene. Accordingly, multiple plant lines transformed with the cosuppression expression cassette are screened to identify those that show the greatest inhibition of ERECTA polypeptide expression.

The polynucleotide used for cosuppression may correspond to all or part of the sequence encoding the ERECTA polypeptide, all or part of the 5' and/or 3' untranslated region of an ERECTA polypeptide transcript, or all or part of both the coding sequence and the untranslated regions of a transcript encoding an ERECTA polypeptide. In some embodiments where the polynucleotide comprises all or part of the coding region for the ERECTA polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) Plant Cell 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al. (1994) Proc. Natl. Acad. Sci. USA 91:3490-3496; Jorgensen, et al., (1996) Plant Mol. Biol. 31:957-973; Johansen and Carrington (2001) Plant Physiol. 126:930-938; Broin, et al., (2002) Plant Cell 14:1417-1432; Stoutjesdijk, et al., (2002) Plant Physiol. 129:1723-1731; Yu, et al., (2003) Phytochemistry 63:753-763; and U.S. Pat. Nos. 5,034,323, 5,283,184 and 5,942,657; each of which is herein incorporated by reference. The efficiency of cosuppression may be increased by including a poly-dT region in the expression cassette at a position 3' to the sense sequence and 5' of the polyadenylation signal. See, United States Patent Publication Number 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

ii. Antisense Suppression

In some embodiments of the invention, inhibition of the expression of the ERECTA polypeptide may be obtained by antisense suppression. For antisense suppression, the expression cassette is designed to express an RNA molecule complementary to all or part of a messenger RNA encoding the ERECTA polypeptide. Over expression of the antisense RNA molecule can result in reduced expression of the native gene. Accordingly, multiple plant lines transformed with the antisense suppression expression cassette are screened to identify those that show the greatest inhibition of ERECTA polypeptide expression.

The polynucleotide for use in antisense suppression may correspond to all or part of the complement of the sequence encoding the ERECTA polypeptide, all or part of the complement of the 5' and/or 3' untranslated region of the ERECTA transcript, or all or part of the complement of both the coding sequence and the untranslated regions of a transcript encoding the ERECTA polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, United States Patent Publication Number 20020048814, herein incorporated by reference.

iii. Double-Stranded RNA Interference

In some embodiments of the invention, inhibition of the expression of a ERECTA polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of ERECTA polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of one or a ERECTA polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk, et al., (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk, et al., (2002) *Plant Physiol.* 129:1723-1731; Waterhouse and Helliwell (2003) *Nat. Rev. Genet.* 4:29-38; Pandolfini, et al., *BMC Biotechnology* 3:7, and United States Patent Publication Number 20030175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and United States Patent Publication Number 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the ERECTA polypeptide). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805 each of which is herein incorporated by reference.

vi. Ribozymes

In some embodiments, the polynucleotide expressed by the expression cassette of the invention is catalytic RNA or has ribozyme activity specific for the messenger RNA of the ERECTA polypeptide. Thus, the polynucleotide causes the degradation of the endogenous messenger RNA, resulting in reduced expression of the ERECTA polypeptide. This method is described, for example, in U.S. Pat. No. 4,987,071, herein incorporated by reference.

vii. Small Interfering RNA or Micro RNA

In some embodiments of the invention, inhibition of the expression of a ERECTA polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of ERECTA expression, the 22-nucleotide sequence is selected from a ERECTA transcript sequence and contains 22 nucleotides of said ERECTA sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding an ERECTA polypeptide, resulting in reduced expression of the gene. In particular embodiments, the zinc finger protein binds to a regulatory region of an ERECTA gene. In other embodiments, the zinc finger protein binds to a messenger RNA encoding an ERECTA polypeptide and prevents its translation. Methods of selecting sites for targeting by zinc finger proteins have been described, for example, in U.S. Pat. No. 6,453,242 and methods for using zinc finger proteins to inhibit the expression of genes in plants are described, for example, in United States Patent Publication Number 20030037355; each of which is herein incorporated by reference.

3. Polypeptide-Based Inhibition of Protein Activity

In some embodiments of the invention, the polynucleotide encodes an antibody that binds to at least one ERECTA polypeptide, and reduces the plant growth regulating activity of the ERECTA polypeptide. In another embodiment, the binding of the antibody results in increased turnover of the antibody-ERECTA complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

4. Gene Disruption

In some embodiments of the present invention, the activity of an ERECTA polypeptide is reduced or eliminated by disrupting the gene encoding the ERECTA polypeptide. The gene encoding the ERECTA polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced plant growth regulating activity.

i. Transposon Tagging

In one embodiment of the invention, transposon tagging is used to reduce or eliminate the ERECTA activity of one or more ERECTA polypeptide. Transposon tagging comprises inserting a transposon within an endogenous ERECTA gene to reduce or eliminate expression of the ERECTA polypeptide. "ERECTA gene" is intended to mean the gene that encodes an ERECTA polypeptide according to the invention.

In this embodiment, the expression of one or more ERECTA polypeptide is reduced or eliminated by inserting a transposon within a regulatory region or coding region of the gene encoding the ERECTA polypeptide. A transposon that is within an exon, intron, 5' or 3' untranslated sequence, a promoter, or any other regulatory sequence of a ERECTA gene may be used to reduce or eliminate the expression and/or activity of the encoded ERECTA polypeptide.

Methods for the transposon tagging of specific genes in plants are well known in the art. See, for example, Maes, et al., (1999) *Trends Plant Sci.* 4:90-96; Dharmapuri and Sonti (1999) *FEMS Microbiol. Lett.* 179:53-59; Meissner, et al., (2000) *Plant J.* 22:265-274; Phogat, et al., (2000) *J. Biosci.* 25:57-63; Walbot (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima, et al., (1998) *Virology* 243: 472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (plant growth regulating activity) of the encoded protein are well known in the art. Insertional mutations in gene exons usually result in null-mutants. Mutations in conserved residues are particularly effective in inhibiting the plant growth regulating activity of the encoded protein. Conserved residues of plant ERECTA polypeptides suitable for mutagenesis with the goal to eliminate plant growth regulating activity have been described. Such mutants can be isolated according to well-known procedures, and mutations in different ERECTA loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more ERECTA polypeptide. Examples of other methods for altering or mutating a genomic nucleotide sequence in a plant are known in the art and include, but are not limited to, the use of RNA:DNA vectors, RNA:DNA mutational vectors, RNA: DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

iii. Modulating Plant Growth and/or Organ Development Activity

In specific methods, the level and/or activity of specific tissue growth in a plant is increased by increasing the level or activity of the ERECTA polypeptide in the plant. Methods for increasing the level and/or activity of ERECTA polypeptides in a plant are discussed elsewhere herein. Briefly, such methods comprise providing a ERECTA polypeptide of the invention to a plant and thereby increasing the level and/or activity of the ERECTA polypeptide. In other embodiments, an ERECTA nucleotide sequence encoding an ERECTA polypeptide can be provided by introducing into the plant a polynucleotide comprising an ERECTA nucleotide sequence of the invention, expressing the ERECTA sequence, increasing the activity of the ERECTA polypeptide, and thereby increasing the number of tissue cells in the plant or plant part. In other embodiments, the ERECTA nucleotide construct introduced into the plant is stably incorporated into the genome of the plant.

In other methods, the number of cells and biomass of a plant tissue is increased by increasing the level and/or activity of the ERECTA polypeptide in the plant. Such methods are disclosed in detail elsewhere herein. In one such method, an ERECTA nucleotide sequence is introduced into the plant and expression of said ERECTA nucleotide sequence decreases the activity of the ERECTA polypeptide, and thereby increasing the plant growth and/or organ development in the plant or plant part. In other embodiments, the ERECTA nucleotide construct introduced into the plant is stably incorporated into the genome of the plant.

As discussed above, one of skill will recognize the appropriate promoter to use to modulate the level/activity of a plant growth and/or organ development polynucleotide and polypeptide in the plant. Exemplary promoters for this embodiment have been disclosed elsewhere herein.

Accordingly, the present invention further provides plants having a modified plant growth and/or organ development when compared to the plant growth and/or organ development of a control plant tissue. In one embodiment, the plant of the invention has an increased level/activity of the ERECTA polypeptide of the invention and thus has increased plant growth and/or organ development in the plant tissue. In other embodiments, the plant of the invention has a reduced or eliminated level of the ERECTA polypeptide of the invention and thus has decreased plant growth and/or organ development in the plant tissue. In other embodiments, such plants have stably incorporated into their genome a nucleic acid molecule comprising a ERECTA nucleotide sequence of the invention operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

Methods for modulating root development in a plant are provided. The methods comprise modulating the level and/or activity of the ERECTA polypeptide in the plant. In one method, an ERECTA sequence of the invention is provided to the plant. In another method, the ERECTA nucleotide sequence is provided by introducing into the plant a polynucleotide comprising an ERECTA nucleotide sequence of the invention, expressing the ERECTA sequence, and thereby modifying root development. In still other methods, the ERECTA nucleotide construct introduced into the plant is stably incorporated into the genome of the plant.

In other methods, root development is modulated by altering the level or activity of the ERECTA polypeptide in the plant. An increase in ERECTA activity can result in at least one or more of the following alterations to root development, including, but not limited to, larger root meristems, increased in root growth, enhanced radial expansion, an enhanced vasculature system, increased root branching, more adventitious roots, and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, United States Application Number 20030074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by increasing the activity and/or level of the ERECTA polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by increasing the level and/or activity of the ERECTA polypeptide also finds use in promoting in vitro propagation of explants.

Furthermore, higher root biomass production due to an increased level and/or activity of ERECTA activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the ERECTA polypeptide of the invention and has enhanced root growth and/or root biomass. In other embodiments, such plants have stably incorporated into their genome a nucleic acid molecule comprising a ERECTA nucleotide sequence of the invention operably linked to a promoter that drives expression in the plant cell.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and United States Application Number 20030074698, each of which is herein incorporated by reference.

The method for modulating shoot and/or leaf development in a plant comprises modulating the activity and/or level of an ERECTA polypeptide of the invention. In one embodiment, an ERECTA sequence of the invention is provided. In other embodiments, the ERECTA nucleotide sequence can be provided by introducing into the plant a polynucleotide comprising an ERECTA nucleotide sequence of the invention, expressing the ERECTA sequence, and thereby modifying shoot and/or leaf development. In other embodiments, the ERECTA nucleotide construct introduced into the plant is stably incorporated into the genome of the plant.

In specific embodiments, shoot or leaf development is modulated by decreasing the level and/or activity of the ERECTA polypeptide in the plant. An decrease in ERECTA activity can result in at least one or more of the following alterations in shoot and/or leaf development, including, but not limited to, reduced leaf number, reduced leaf surface, reduced vascular, shorter internodes and stunted growth, and retarded leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, and leaf-preferred promoters. Exemplary promoters have been disclosed elsewhere herein.

Decreasing ERECTA activity and/or level in a plant results in shorter internodes and stunted growth. Thus, the methods of the invention find use in producing dwarf plants. In addition, as discussed above, modulation of ERECTA activity in the plant modulates both root and shoot growth. Thus, the present invention further provides methods for altering the root/shoot ratio. Shoot or leaf development can further be modulated by decreasing the level and/or activity of the ERECTA polypeptide in the plant.

Accordingly, the present invention further provides plants having modulated shoot and/or leaf development when compared to a control plant. In some embodiments, the plant of the invention has an increased level/activity of the ERECTA polypeptide of the invention, altering the shoot and/or leaf development. Such alterations include, but are not limited to, increased leaf number, increased leaf surface, increased vascularity, longer internodes and increased plant stature, as well as alterations in leaf senescence, as compared to a control plant. In other embodiments, the plant of the invention has a decreased level/activity of the ERECTA polypeptide of the invention.

vi Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the ERECTA polypeptide has not been modulated. "Modulating floral development" further includes any alteration in the timing of the development of a plant's reproductive tissue (i.e., a delayed or an accelerated timing of floral development) when compared to a control plant in which the activity or level of the ERECTA polypeptide has not been modulated. Macroscopic alterations may include changes in size, shape, number, or location of reproductive organs, the developmental time period that these structures form, or the ability to maintain or proceed through the flowering process in times of environmental stress. Microscopic alterations may include changes to the types or shapes of cells that make up the reproductive organs.

The method for modulating floral development in a plant comprises modulating ERECTA activity in a plant. In one method, an ERECTA sequence of the invention is provided. An ERECTA nucleotide sequence can be provided by introducing into the plant a polynucleotide comprising an ERECTA nucleotide sequence of the invention, expressing the ERECTA sequence, and thereby modifying floral development. In other embodiments, the ERECTA nucleotide construct introduced into the plant is stably incorporated into the genome of the plant.

In specific methods, floral development is modulated by decreasing the level or activity of the ERECTA polypeptide in the plant. A decrease in ERECTA activity can result in at least one or more of the following alterations in floral development, including, but not limited to, retarded flowering, reduced number of flowers, partial male sterility, and reduced seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters, and inflorescence-preferred promoters.

In other methods, floral development is modulated by increasing the level and/or activity of the ERECTA sequence of the invention. Such methods can comprise introducing an ERECTA nucleotide sequence into the plant and increasing the activity of the ERECTA polypeptide. In other methods, the ERECTA nucleotide construct introduced into the plant is stably incorporated into the genome of the plant. Increasing expression of the ERECTA sequence of the invention can modulate floral development during periods of stress. Such methods are described elsewhere herein. Accordingly, the present invention further provides plants having modulated floral development when compared to the floral development of a control plant. Compositions include plants having an increased level/activity of the ERECTA polypeptide of the invention and having an altered floral development. Compositions also include plants having an increased level/activity of the ERECTA polypeptide of the invention wherein the plant maintains or proceeds through the flowering process in times of stress.

Methods are also provided for the use of the ERECTA sequences of the invention to increase seed size and/or weight. The method comprises increasing the activity of the ERECTA sequences in a plant or plant part, such as the seed. An increase in seed size and/or weight comprises an increased size or weight of the seed and/or an increase in the size or weight of one or more seed part including, for example, the embryo, endosperm, seed coat, aleurone, or cotyledon.

As discussed above, one of skill will recognize the appropriate promoter to use to increase seed size and/or seed weight. Exemplary promoters of this embodiment include constitutive promoters, inducible promoters, seed-preferred promoters, embryo-preferred promoters, and endosperm-preferred promoters.

The method for decreasing seed size and/or seed weight in a plant comprises decreasing ERECTA activity in the plant. In one embodiment, the ERECTA nucleotide sequence can be provided by introducing into the plant a polynucleotide comprising a ERECTA nucleotide sequence of the invention, expressing the ERECTA sequence, and thereby decreasing seed weight and/or size. In other embodiments, the ERECTA nucleotide construct introduced into the plant is stably incorporated into the genome of the plant.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can also result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention has an increased level/activity of the ERECTA polypeptide of the invention and has an increased seed weight and/or seed size. In other embodiments, such plants have stably incorporated into their genome a nucleic acid molecule comprising a ERECTA nucleotide sequence of the invention operably linked to a promoter that drives expression in the plant cell.

vii. Method of Use for ERECTA Promoter Polynucleotides

The polynucleotides comprising the ERECTA promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the ERECTA promoter polynucleotides of the invention are provided in expression cassettes along with a polynucleotide sequence of interest for expression in the host cell of interest. As discussed in Example 2 below, the ERECTA promoter sequences of the invention are expressed in a variety of tissues and thus the promoter sequences can find use in regulating the temporal and/or the spatial expression of polynucleotides of interest.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising the ERECTA promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) *Curr. Opin. Plant Biol.* 1:311-315. Alternatively, a synthetic ERECTA promoter sequence may comprise duplications of the upstream promoter elements found within the ERECTA promoter sequences.

It is recognized that the promoter sequence of the invention may be used with its native ERECTA coding sequences. A DNA construct comprising the ERECTA promoter operably linked with its native ERECTA gene may be used to transform any plant of interest to bring about a desired phenotypic change, such as modulating cell number, modulating root, shoot, leaf, floral, and embryo development, stress tolerance, and any other phenotype described elsewhere herein.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232, 529); balanced amino acids (e.g., hordothionins (U.S. Pat. Nos. 5,990,389; 5,885,801; 5,885,802; and 5,703,409); barley high lysine (Williamson, et al., (1987) *Eur. J. Biochem.* 165:99-106; and WO 98/20122); and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. patent application Ser. No. 10/053, 410, filed Nov. 7, 2001); and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593, 881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane H$^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem.* 27:16749-16752, Arredondo-Peter, et al., (1997) *Plant Physiol.* 115: 1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016 and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser, et al., (1986) *Gene* 48:109); and the like.

Genes encoding disease resistance traits include detoxification genes, such as against fumonosin (U.S. Pat. No. 5,792, 931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Isolation of ERECTA Sequences

Figure 4:
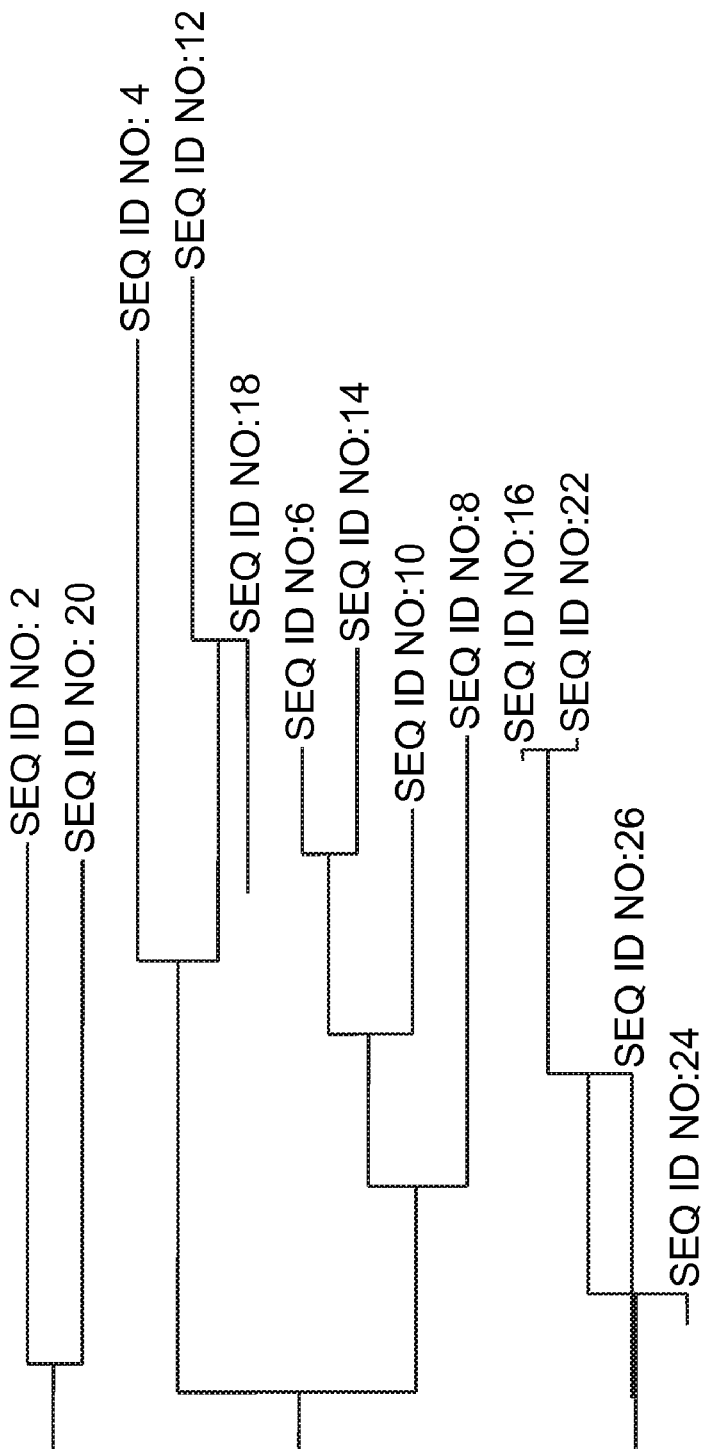
FIG. 4: Dendrogram showing relationship of ERECTA sequences from *Arabidopsis*, maize, soybean, sorghum and rice.

A routine for identifying all members of a gene family was employed to search for the ERECTA genes of interest. A diverse set of all the known members of the gene family as protein sequences was prepared. This data includes sequences from other species. These species are searched against a proprietary maize sequence dataset and a nonredundant set of overlapping hits is identified. Separately, one takes the nucleotide sequences of any genes of interest in hand and searches against the database and a nonredundant set of all overlapping hits are retrieved. The set of protein hits are then compared to the nucleotide hits. If the gene family is complete, all of the protein hits are contained within the nucleotide hits. The ERECTA family of genes consists of 2 *Arabidopsis* genes, 2 rice genes, 2 maize genes, 3 sorghum genes and 4 soybean genes. A dendrogram representation of the interrelationship of the proteins encoded by these genes is provided as FIG. 4.

Example 2

ERECTA Sequence Analysis

The ZmERECTA polypeptides of the current invention have common characteristics with ERECTA genes in a variety of plant species. The relationship between the genes, conserved regions and consensus sequence from the multiple plant species is shown in an alignment, see FIG. 2.

Example 3

Transformation and Regeneration of Transgenic Plants

Immature maize embryos from greenhouse donor plants are bombarded with a plasmid containing the ZmERECTA sequence operably linked to the drought-inducible promoter RAB17 promoter (Vilardell, et al., (1990) *Plant Mol Biol* 14:423-432) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% Clorox® bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA:

A plasmid vector comprising the ERECTA sequence operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment:

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce, et al., (2002) *Journal of Experimental Botany* 53:1-13.

Bombardment and Culture Media:

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6);

and 6 g/l bacto-agar (added after bringing to volume with polished D-I H$_2$O), sterilized and cooled to 60° C.

Example 4

Agrobacterium-Mediated Transformation

For Agrobacterium-mediated transformation of maize with an antisense sequence of the ZmERECTA sequence of the present invention, preferably the method of Zhao is employed (U.S. Pat. No. 5,981,840, and PCT patent publication number WO98/32326; the contents of which are hereby incorporated by reference). Briefly, immature embryos are isolated from maize and the embryos contacted with a suspension of Agrobacterium, where the bacteria are capable of transferring the ERECTA sequence to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Plants are monitored and scored for a modulation in meristem development. For instance, alterations of size and appearance of the shoot and floral meristems and/or increased yields of leaves, flowers, and/or fruits.

Example 5

Over Expression of ZmERECTA Affects Plant Growth Rate, Inflorescence Development, Organ Size, and Drought Tolerance The ZmERECTA gene is expressed in shoot apical meristem and ear specific meristems where cell division is active (FIG. 1). The function of the gene is associated with cell proliferation. We are testing the function of ZmERECTA gene by over expressing it under a constitutive promoter. Transgenic plants and non-transgenic sibs will be produced and compared for the transgene effects. Transgenic plants expressing the transgene will be confirmed by transgene-specific RT-PCR. The ZmERECTA gene is expected to impact plant growth rate. Compared to the transgenic negative siblings, transgenic positive plants are expected to show enhanced growth rate, increased plant and organ size, and increased biomass accumulation.

The ERECTA gene is shown to control flower development in Arabidopsis. The ZmERECTA gene is naturally expressed preferentially in the maize ear inflorescence meristem, and at slightly lower level in the shoot apical meristem as found in FIG. 1. Transgenic plants over expressing the ZmERECTA gene, is expected to show impact on inflorescence development. Comparing to non-transgenic sibs, transgenic plants are expected to show enhanced ear and kernel growth, and a final grain yield increase.

The ERECTA gene regulates transpiration efficiency in Arabidopsis and impact drought tolerance. This function of the ZmERECTA gene is tested in transgenic plants by over expressing it with either a constitutive, or stress inducible promoters. Transgenic plants and their non-transgenic sibs will be given drought stress treatment, to test their tolerance by measuring plant growth, biomass accumulation, and yield under the stressed environments. Transgenic plants are expected to show improved drought tolerance by affecting transpiration efficiency and enhance plant growth and grain yield under stressed or non-stressed growing conditions.

Example 6

Soybean Embryo Transformation

Soybean embryos are bombarded with a plasmid containing an ERECTA sequence operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) Nature (London) 327:70-73; U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188), and the 3' region of the nopaline synthase gene from the T-DNA of the Ti plasmid of Agrobacterium tumefaciens. The expression cassette comprising an ERECTA sense sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Sunflower Meristem Tissue Transformation

Sunflower meristem tissues are transformed with an expression cassette containing an ERECTA sequence operably linked to a ubiquitin promoter as follows (see also, European Patent Number EP 0 486233, herein incorporated by reference, and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox® bleach solution with the addition of two drops of Tween 20 per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:473-497), Shepard's vitamin additions (Shepard (1980) in *Emergent Techniques for the Genetic Improvement of Crops* (University of Minnesota Press, St. Paul, Minn.)), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ERECTA gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by ERECTA activity analysis of leaf extracts while transgenic seeds harvested from NPTII-positive $T_0$ plants are identified by ERECTA activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox® bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive (i.e., a change in ERECTA expression) explants are identified, those shoots that fail to exhibit an alteration in ERECTA activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for altered ERECTA expression are grafted to Pioneer hybrid 6440 in vitro-grown sunflower seedling rootstock. The rootstocks are prepared in the following manner. Seeds are dehulled and surface-sterilized for 20 minutes in a 20% Clorox® bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 8

Protocol for Measuring Maize Vegetative Performance Under Drought Stress

Genes conferring drought tolerance to transgenic maize can be identified in the FAST-corn (see, U.S. patent application Ser. No. 10/367,417) background in a high-throughput mode using the growth conditions, stress treatment and diagnostic methods identified.

Treatment and Materials:
Two treatment groups are used, one well watered (control), one drought stressed.
Plant material consists of transgenic maize seedlings at T1 stage.

Treatment Details:
Stress will be imposed starting at 10 to 14 DAS or 7 days after transplanting, and will be continued through to silking. Pots will be watered by an automated system fitted to timers to provide watering at 25 or 50% of field capacity during the entire period of drought-stress treatment. This stress should allow identification of the impact on vegetative growth as well as on anthesis-silking interval.

Potting mixture: A mixture of ⅓ Turface MVP (Profile Products LLC, IL, USA), ⅓ sand and ⅓ SB300 Universal (Sun Gro Horticulture, WA, USA) is suggested. The SB300 Universal can be replaced with Fafard Superfine Germinating Mix (Conrad Fafard, Inc., MA, USA). Also, the proportion of sand in the mixture can be reduced. Thus, a final potting mixture can be ⅜ (37.5%) turface, ⅜ (37.5%) Fafard and ¼ (25%) sand.

Field Capacity Determination: Determine the weight of the soil mixture (w1) to be used in one S200 pot (minus the pot weight). The soil can be dried at 100° C. to constant weight before determining w1 (I do not do that if all components of the soil mix are already dry). Water the soil in the pot to full saturation and allow all the gravitational water to drain out. Determine the weight of the soil (w2) after all gravitational water has seeped out (minus the pot weight). Field capacity is the weight of the water remaining in the soil obtained as w2−w1. Technically it is written as a percentage of the oven-dry soil weight. For our purposes, w2−w1 would suffice.

Stress Treatment: During the early part of plant growth (10DAS to 21DAS), provide the well-watered control with a daily watering of 75% field capacity and the drought-stress treatment with a daily watering of 25% field capacity, both given as a single daily dose at 10 AM. As the plants grow bigger, increase the daily watering of the well-watered control to full field capacity and the drought stress treatment to 50% field capacity. This increase is based on weight measurements on representative pots to determine the extent of water withdrawal by the plant as it grows bigger.

Nutrient Solution: Use a modified Hoagland's solution at ¹⁄₁₆ dilution with tap water for irrigation. Prepare 20 L of the modified Hoagland's solution with the following recipe:

| | |
|---|---|
| 10× Micronutrient Solution | 16 mL |
| KH2PO4 (MW: 136.02) | 22 g |
| MgSO4 (MW: 120.36) | 77 g |
| KNO3 (MW: 101.2) | 129.5 g |
| Ca(NO3)2•4H20 (MW: 236.15) | 151 g |

-continued

| | |
|---|---|
| NH4NO3 (MW: 80.04) | 25.6 g |
| Sprint 330 (Iron chelate) | 32 g |

Prepare 1 L of the 10× Micronutrient Solution using the following recipe:

| 10× Micronutrient Solution | mg/L |
|---|---|
| H3BO3 - 30 mM | 1854 |
| MnCl2•4H2O - 10 mM | 1980 |
| ZnSO4•7H2O - 10 mM | 2874 |
| CuSO4•5H2O - 1 mM | 250 |
| H2MoO4•H2O - 1 mM | 242 |

Use fertilizer grade KNO3.

Note: it is useful to add half a teaspoon of Osmocote (NPK 15:9:12) to the pot at the time of transplanting or after emergence (The Scotts Miracle-Gro Company, OH, USA).

Border plants: It is critical to have a row of border plants on bench-edges adjacent to the glass walls of the greenhouse or adjacent potential causes of microenvironment variability such as a cooler fan.

Automation: Can be done using PVC pipes with drilled holes to supply water to systematically positioned pots using a siphoning device. Irrigation scheduling can be done using timers.

Statistical analysis: Data will be incorporated into Spotfire (Spotfire, Inc., MA, USA) eventually for ANOVA within each drought transgenic batch, using a factorial randomised block design (with events or construct means and stress treatment as factors).

Replications: 8 to 10 individual plants per treatment per event.

Pot size: S200

Observations:
(1) LemnaTec measurements three times a week throughout growth to capture plant-growth rate. (LemnaTec GmbH, Wurselen, Germany)
(2) Leaf color determinations three times a week throughout the stress period using the Lemnatec.
(3) Chlorophyll fluorescence recorded as PhiPSII twice weekly, starting at 11 am using the Hansatech FMS2 instrument. Start measurements at day 0 of stress treatment until the end of experiment and record measurements on the youngest most fully expanded leaf. (Hansatech Instruments, Norfolk, England).
(4) Record dates of tasseling and silking on individual plants, and compute Anthesis Silking Interval (ASI). ASI computations are made by determining difference between the growing degree days (GDU) to shedding and that to silking. Shedding time is the day when first shedding is observed where first shedding is defined as at least one anther has shed. Silking time is the day when first silking is observed, where first silking is defined as at least one millimeter of one silk emerging.

Example 9

Expression of ERECTA and Association with Drought Tolerance and Agronomic Performance A set of protein kinases have been identified based on (1) published information on orthologs that is indicative of a role in stress perception or tolerance and (2) in-house profiling studies indicative of stress-related gene expression. They included genes of the two-component signaling system, and genes that were identified based on their stress-related expression pattern—including ERECTA-A.

ERECTA-A

Background information: ERECTA is a putative leucine-rich repeat receptor-like kinase (LRR-RLK) which has implications for agriculture, especially in the areas of drought tolerance and agronomic performance. In *Arabidopsis*, this gene is known to contribute to plant transpiration efficiency through mechanisms including stomatal density, epidermal cell expansion, mesophyll cell proliferation and cell-cell contact. The gene has also been known to influence inflorescence development. No kinase activity assays have been reported for the protein.

Figure 3:
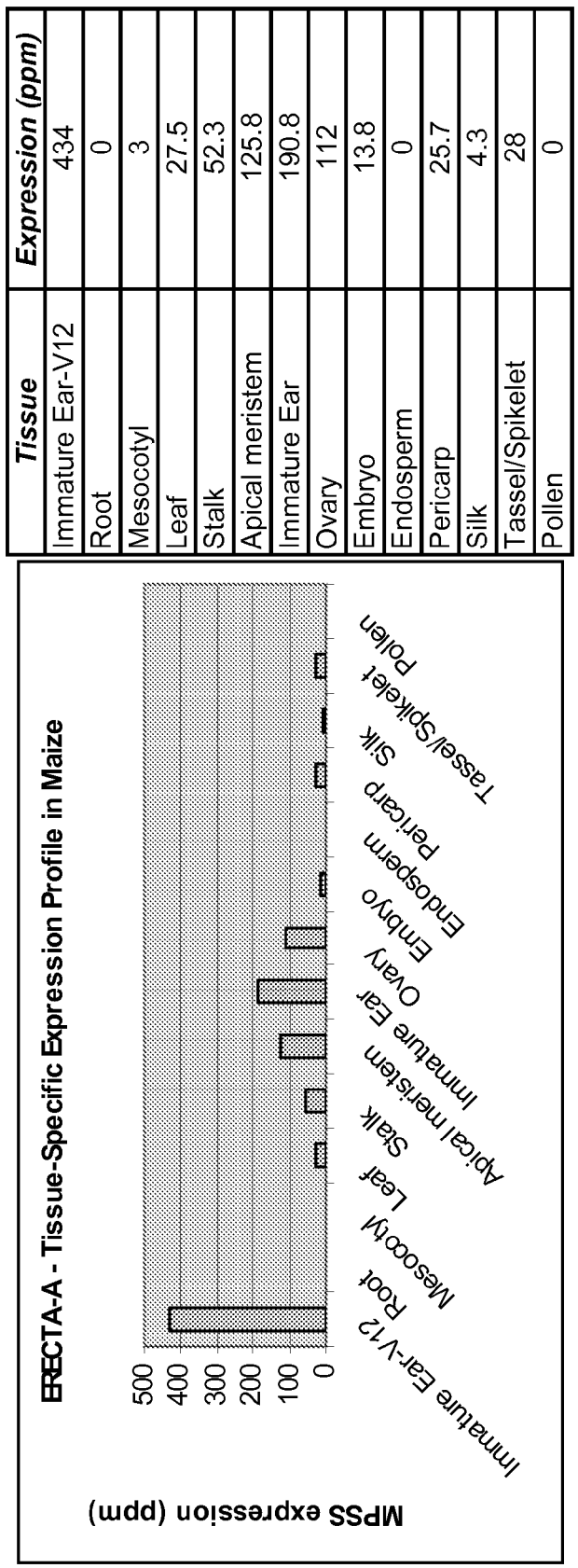
FIG. 3: The expression of the ERECTA A gene (SEQ ID NO: 3) is meristem and immature-ear preferred, with expression in multiple tissues as detailed.

Sequence information: A full-length CDS was cloned. The gene maps to chromosome-bin position 6.04, in the general vicinity of which drought QTLs are known to occur. The expression of the gene is meristem and immature-ear preferred, with expression in multiple tissues as described in FIG. 3.

Example 10

Variants of ERECTA Sequences

A. Variant Nucleotide Sequences of ERECTA that do not Alter the Encoded Amino Acid Sequence The ERECTA nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants are altered, the amino acid sequence encoded by the open reading frames do not change.

B. Variant Amino Acid Sequences of ERECTA Polypeptides

Variant amino acid sequences of the ERECTA polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment set forth in FIG. 2, an appropriate amino acid can be changed. Once the targeted amino acid is identified, the procedure outlined in the following section C is followed. Variants having about 70%, 75%, 80%, 85%, 90%, and 95% nucleic acid sequence identity are generated using this method.

C. Additional Variant Amino Acid Sequences of ERECTA Polypeptides

In this example, artificial protein sequences are created having 80%, 85%, 90% and 95% identity relative to the reference protein sequence. This latter effort requires identifying conserved and variable regions from the alignment set forth in FIG. 2 and then the judicious application of an amino acid substitutions table. These parts will be discussed in more detail below.

Largely, the determination of which amino acid sequences are altered is made based on the conserved regions among ERECTA protein or among the other ERECTA polypeptides. Based on the sequence alignment, the various regions of the ERECTA polypeptide that can likely be altered are represented in lower case letters, while the conserved regions are represented by capital letters. It is recognized that conservative substitutions can be made in the conserved regions below without altering function. In addition, one of skill will understand that functional variants of the ERECTA sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 2.

TABLE 2

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the ERECTA polypeptides are generating having about 80%, 85%, 90%, and 95% amino acid identity to the starting unaltered ORF nucleotide sequence of SEQ ID NOS: 27-39.

Example 11

Transgenic Plants Expressing ZmERECTA A Demonstrate Growth Enhancement

Transgenic plants over expressing the ZmERECTA A gene were evaluated in the field. Transgenic positive events and their null control were characterized for traits related to plant and organ growth. In the early growing season, transgenic positive plants showed enhanced growth, specifically a faster growth rate. Transgenic plants reached the flowering stage approximately two days sooner than the non-transgenic control. Transgenic plants also show enhanced canopy, which is associated with increased leaf size. Both the length and the width of the leaf are increased, contributing to the significantly increased leaf area of the transgenic plants. Leaf area increases of up to 34% were found in comparison to the non transgenic control. The transgene effects of ZmERECTA A on growth rate and organ size is consistent with its predicted role in controlling plant and organ size, and promoting cell proliferation (Shpak, E. D., et al., *Plant Cell* (2003) 15:1095-1110; *Development* (2004) 131:1491-501). These data support the notion that ZmERECTA A may find utility in controlling the size of the whole plant, or specific organs in maize or other crops.

Data was collected measuring the stomata density (stomata counts per $mm^2$). Based on 3 areas per leaf and 2 leaves (plants) per event, it was observed that the stomatal density of the transgenic positive plants decreased in all five events as compared to the negative control. The reduction ranged from 5-22% as compared to the transgenic negative control. The transgene effect on stomatal density is consistent with the role of this gene in *Arabidopsis*, where the gene was shown to reduce stomatal density and improve transpiration efficiency, and therefore, improve drought tolerance (Masle, Gilmore and Farquhar, (2005) *Nature* 436:866). The consistency of the transgene effect in maize stomatal density increases its potential for conferring a drought tolerance in crop species.

The leaf tricome growth was affected in transgenic positive plants, such that the transgenic positives have either more tricomes or more densely populated tricomes. As measured though various events, an increase in tricome growth of up to 28% was found. Tricome growth is thought to be associated with plant drought tolerance and insect resistance by providing hydro-repellency and reflective properties to the leaf and physical and chemical deterrents to insect feeding (Esau, K. (1977) *Anatomy of Seed Plants*, Ed. 2). Such phenotypic effects of transgenic ERECTA could lead to impact drought tolerance and insect resistance.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated polynucleotide selected from the group consisting of:
   a. a polynucleotide having at least 95% sequence identity, as determined by the GAP algorithm under default parameters, to the full length sequence of a polynucleotide of SEQ ID NO: 5; wherein a plant transformed with said polynucleotide exhibits an increase in leaf tissue growth;
   b. a polynucleotide encoding a polypeptide of SEQ ID NO: 6 and
   c. a polynucleotide of SEQ ID NO: 5 and
   d. A polynucleotide which is fully complementary to the polynucleotide of (a), (b) or (c).

2. A recombinant expression cassette, comprising the polynucleotide of claim 1, wherein the polynucleotide is operably linked, in sense orientation, to a promoter.

3. An isolated host cell comprising the expression cassette of claim 2.

4. A transgenic plant comprising the recombinant expression cassette of claim 2.

5. The transgenic plant of claim 4, wherein said plant is a monocot.

6. The transgenic plant of claim 4, wherein said plant is a dicot.

7. The transgenic plant of claim 4, wherein said plant is selected from the group consisting of: maize, soybean, sunflower, sorghum, canola, wheat, alfalfa, cotton, rice, barley, millet, peanut and cocoa.

8. A transgenic seed from the transgenic plant of claim 4 wherein the seed comprises the expression cassette.

9. A method of modulating organ size in plants, comprising:
   a. introducing into a plant cell a recombinant expression cassette comprising the polynucleotide of claim 1 operably linked to a promoter; and
   b. culturing the plant under plant cell growing conditions; wherein the organ size in said plant is modulated.

10. The method of claim 9, wherein the plant cell is from a plant selected from the group consisting of: maize, soybean, sunflower, sorghum, canola, wheat, alfalfa, cotton, rice, barley, millet, peanut and cocoa.

11. A method of increasing the size of a whole plant or organ size of a plant, comprising:
   a. introducing into a plant cell a recombinant expression cassette comprising the polynucleotide of claim 1 operably linked to a promoter;
   b. culturing the plant cell under plant cell growing conditions; and
   c. regenerating a plant from said plant cell; wherein the organ size in said plant is increased.

12. The method of claim 11, wherein the plant is selected from the group consisting of: maize, soybean, sorghum, canola, wheat, alfalfa, cotton, rice, barley, millet, peanut and cocoa.

* * * * *